US008828925B2

(12) United States Patent
Demeule et al.

(10) Patent No.: US 8,828,925 B2
(45) Date of Patent: Sep. 9, 2014

(54) ETOPOSIDE AND DOXORUBICIN CONJUGATES FOR DRUG DELIVERY

(75) Inventors: Michel Demeule, Beaconsfield (CA); Christian Che, Longueuil (CA); Reinhard Gabathuler, Verdun (CA); Gaoqiang Yang, Montréal (CA)

(73) Assignee: Angiochem Inc., Montreal (CA)

( * ) Notice: Subject to any disclaimer, the term of this patent is extended or adjusted under 35 U.S.C. 154(b) by 11 days.

(21) Appl. No.: 13/124,022

(22) PCT Filed: Oct. 15, 2009

(86) PCT No.: PCT/CA2009/001481
§ 371 (c)(1),
(2), (4) Date: Feb. 8, 2012

(87) PCT Pub. No.: WO2010/043049
PCT Pub. Date: Apr. 22, 2010

(65) Prior Publication Data
US 2012/0135914 A1 May 31, 2012

Related U.S. Application Data

(60) Provisional application No. 61/105,654, filed on Oct. 15, 2008, provisional application No. 61/171,010, filed on Apr. 20, 2009.

(51) Int. Cl.
*A61K 38/00* (2006.01)
*A61K 47/48* (2006.01)
*A61K 31/7048* (2006.01)
*A61K 38/10* (2006.01)
*A61K 39/395* (2006.01)

(52) U.S. Cl.
CPC ....... *A61K 47/48246* (2013.01); *A61K 31/7048* (2013.01); *A61K 38/10* (2013.01); *A61K 39/39558* (2013.01); *A61K 47/48238* (2013.01)
USPC ......................................................... 514/1.3

(58) Field of Classification Search
CPC ................ A61K 47/48246; A61K 31/7048; A61K 38/10; A61K 39/39558; A61K 47/48238
See application file for complete search history.

(56) References Cited

U.S. PATENT DOCUMENTS

| | | | |
|---|---|---|---|
| 4,671,958 A | 6/1987 | Rodwell et al. |
| 4,801,575 A | 1/1989 | Pardridge |
| 4,902,505 A | 2/1990 | Pardridge et al. |
| 4,942,184 A | 7/1990 | Haugwitz et al. |
| 5,028,697 A | 7/1991 | Johnson et al. |
| 5,041,424 A | 8/1991 | Saulnier et al. |
| 5,118,668 A | 6/1992 | Auerswald et al. |
| 5,126,249 A | 6/1992 | Becker et al. |
| 5,169,933 A | 12/1992 | Anderson et al. |
| 5,204,354 A | 4/1993 | Chakravarty et al. |
| 5,223,409 A | 6/1993 | Ladner et al. |
| 5,258,499 A | 11/1993 | Konigsberg et al. |
| 5,362,831 A | 11/1994 | Mongelli et al. |
| 5,442,043 A | 8/1995 | Fukuta et al. |
| 5,578,451 A | 11/1996 | Nishimoto |
| 5,627,270 A | 5/1997 | Kahne et al. |
| RE35,524 E | 6/1997 | Saulnier et al. |
| 5,683,694 A | 11/1997 | Bagshawe et al. |
| 5,780,265 A | 7/1998 | Dennis et al. |
| 5,807,980 A | 9/1998 | Lasters et al. |
| 5,869,045 A | 2/1999 | Hellstrom et al. |
| 5,922,754 A | 7/1999 | Burchett et al. |
| 5,948,750 A | 9/1999 | Garsky et al. |
| 5,948,888 A | 9/1999 | de la Monte et al. |
| 5,955,444 A | 9/1999 | Ingram et al. |
| 5,962,266 A | 10/1999 | White et al. |
| 5,981,564 A | 11/1999 | Pagé et al. |
| 6,093,692 A | 7/2000 | Shen et al. |
| 6,126,965 A | 10/2000 | Kasid et al. |
| 6,191,290 B1 | 2/2001 | Safavy |
| 6,245,359 B1 | 6/2001 | Milstein et al. |
| 6,306,993 B1 | 10/2001 | Rothbard et al. |
| 6,310,039 B1 | 10/2001 | Kratz |
| 6,316,024 B1 | 11/2001 | Allen et al. |
| 6,348,207 B1 | 2/2002 | Milstein et al. |
| 6,376,648 B2 | 4/2002 | White et al. |

(Continued)

FOREIGN PATENT DOCUMENTS

| | | |
|---|---|---|
| CA | 2283474 | 9/1998 |
| CA | 2525236 A1 | 1/2005 |

(Continued)

OTHER PUBLICATIONS

Garsky et al., J. Med. Chem. 2001, 44, 4216-4224.*
Anonymous, Blood-Brain Barrier Tackled, ecancermedicalscience, Oct. 22, 2008, retrieved on Dec. 11, 2012 from the Internet: [http://ecancer.org/news/326].*
Nagy et al., Proc. Natl. Acad. Sci. USA, 1997, vol. 94, pp. 652-656.*
Regina et al., British Journal of Pharmacology, 2008, 155, 185-197, published online Jun. 23, 2008.*

(Continued)

*Primary Examiner* — Marcela M Cordero Garcia
*Assistant Examiner* — Kaipeen Yang
(74) *Attorney, Agent, or Firm* — Clark & Elbing LLP; Kristina Bieker-Brady

(57) ABSTRACT

The invention relates to improvements in the field of drug delivery. More particularly, the invention relates to polypeptides having a hydrolyzable covalent bond to a therapeutic agent that includes, etoposide, etoposide 4'-dimethylglycine or doxorubicin. These polypeptide conjugates can be used as vectors to transport the podophyllotoxin derivative across the blood brain barrier (BBB) or into particular cell types such as ovary, liver, lung, or kidney. The invention also relates to pharmaceutical compositions that include the compounds of the invention and to uses thereof in methods of treatment.

7 Claims, 15 Drawing Sheets

(56) References Cited

U.S. PATENT DOCUMENTS

| | | |
|---|---|---|
| 6,391,305 B1 | 5/2002 | Feng et al. |
| 6,469,047 B1 | 10/2002 | Jackson et al. |
| 6,475,481 B2 | 11/2002 | Talmadge |
| 6,475,781 B1 | 11/2002 | Mercola et al. |
| 6,495,513 B1 | 12/2002 | Rueger et al. |
| 6,613,890 B2 | 9/2003 | White et al. |
| 6,660,525 B2 | 12/2003 | Martin et al. |
| 6,689,582 B1 | 2/2004 | Davies et al. |
| 6,713,454 B1 | 3/2004 | Ekwuribe et al. |
| 6,906,033 B2 | 6/2005 | White et al. |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,319,090 B2 | 1/2008 | Katz |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Beliveau et al. |
| 8,530,429 B2 | 9/2013 | Robbins et al. |
| 8,569,323 B2 | 10/2013 | Ren et al. |
| 2003/0129186 A1 | 7/2003 | Beliveau et al. |
| 2003/0170891 A1 | 9/2003 | McSwiggen |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 | 8/2004 | Harris et al. |
| 2004/0220132 A1 | 11/2004 | Kaemmerer |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0107325 A1 | 5/2005 | Manoharan et al. |
| 2005/0178395 A1 | 8/2005 | Hunter et al. |
| 2005/0183731 A1 | 8/2005 | Hunter et al. |
| 2006/0019347 A1 | 1/2006 | Cho et al. |
| 2006/0029609 A1 | 2/2006 | Zankel et al. |
| 2006/0182684 A1 | 8/2006 | Beliveau |
| 2006/0189515 A1 | 8/2006 | Beliveau et al. |
| 2006/0251713 A1 | 11/2006 | Ben-Sasson et al. |
| 2007/0031844 A1 | 2/2007 | Khvorova et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1 | 9/2007 | Bridon et al. |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0021883 A1 | 1/2009 | Delida |
| 2009/0082277 A1 | 3/2009 | Beliveau et al. |
| 2009/0215883 A1 | 8/2009 | Bouzada et al. |
| 2009/0221477 A1 | 9/2009 | Artymiuk et al. |
| 2009/0246211 A1 | 10/2009 | Henri et al. |
| 2010/0209429 A1 | 8/2010 | Erlich et al. |
| 2010/0256055 A1 | 10/2010 | Castaigne et al. |
| 2010/0284921 A1 | 11/2010 | Gordon et al. |
| 2011/0059187 A1 | 3/2011 | Basu et al. |
| 2011/0171128 A1 | 7/2011 | Beliveau et al. |
| 2011/0218152 A1 | 9/2011 | Beliveau et al. |
| 2011/0305750 A1 | 12/2011 | Beliveau et al. |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034572 A1 | 2/2013 | Stanimirovic et al. |
| 2013/0035069 A1 | 2/2013 | Fisher |
| 2013/0045873 A1 | 2/2013 | Hood et al. |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |

FOREIGN PATENT DOCUMENTS

| | | |
|---|---|---|
| CA | 2637893 | 7/2007 |
| CA | 2638034 | 7/2007 |
| CN | 101262890 A | 9/2008 |
| CN | 102406949 A | 4/2012 |
| CN | 102552928 A | 7/2012 |
| CN | 102614105 A | 8/2012 |
| DE | 19953696 | 5/2001 |
| EP | 0393431 | 10/1990 |
| EP | 0495049 B1 | 7/1992 |
| EP | 1982699 A1 | 10/2008 |
| EP | 2333074 A1 | 6/2011 |
| JP | 2007-509977 A | 4/2007 |
| RU | 2172323 C2 | 10/1999 |
| WO | WO 87/05702 | 9/1987 |
| WO | WO 96/31531 | 10/1996 |
| WO | WO 96/35788 | 11/1996 |
| WO | WO-96/39160 A1 | 12/1996 |
| WO | WO 96/39183 | 12/1996 |
| WO | WO 96/40210 | 12/1996 |
| WO | WO 97/33996 | 9/1997 |
| WO | WO 97/40854 | 11/1997 |
| WO | WO 00/01417 | 1/2000 |
| WO | WO 00/71574 | 11/2000 |
| WO | WO 01/30319 | 5/2001 |
| WO | WO-02/13873 A2 | 2/2002 |
| WO | WO 02/33090 | 4/2002 |
| WO | WO-02/43765 A2 | 6/2002 |
| WO | WO-02/085923 A2 | 10/2002 |
| WO | WO 03/009815 | 2/2003 |
| WO | WO-03/102583 A1 | 12/2003 |
| WO | WO 2004/060403 | 7/2004 |
| WO | PCT/JP2004/011668 | 8/2004 |
| WO | WO 2004/091623 | 10/2004 |
| WO | WO-2004/093897 A1 | 11/2004 |
| WO | WO-2004/108071 A2 | 12/2004 |
| WO | WO 2005/002515 | 1/2005 |
| WO | WO-2005/014625 A1 | 2/2005 |
| WO | WO-2005/021579 A2 | 3/2005 |
| WO | WO-2005/042029 A2 | 5/2005 |
| WO | WO 2006/086870 | 8/2006 |
| WO | WO-2006/089290 A1 | 8/2006 |
| WO | WO 2006086870 A1 * | 8/2006 |
| WO | WO-2006/108052 A2 | 10/2006 |
| WO | WO-2006/138343 A2 | 12/2006 |
| WO | WO 2007/009229 | 1/2007 |
| WO | WO 2007/020085 | 2/2007 |
| WO | WO 2007/030619 | 3/2007 |
| WO | WO-2007/035716 A2 | 3/2007 |
| WO | WO-2007/044323 A2 | 4/2007 |
| WO | WO-2007/082978 A1 | 7/2007 |
| WO | WO-2007/082979 A1 | 7/2007 |
| WO | WO 2007/103515 | 9/2007 |
| WO | WO 2007/113172 | 10/2007 |
| WO | WO 2008/012629 | 1/2008 |
| WO | WO-2008/036682 A2 | 3/2008 |
| WO | WO 2008/046228 | 4/2008 |
| WO | WO 2008/069876 | 6/2008 |
| WO | WO-2008/116171 A1 | 9/2008 |
| WO | WO 2008/144919 | 12/2008 |
| WO | WO 2009/039188 | 3/2009 |
| WO | WO 2009/046220 | 4/2009 |
| WO | WO 2009/070597 | 6/2009 |
| WO | WO 2009/079790 | 7/2009 |
| WO | WO 2009/105671 | 8/2009 |
| WO | WO 2009/127072 | 10/2009 |
| WO | WO-2010/006239 A2 | 1/2010 |
| WO | WO 2010/043047 | 4/2010 |
| WO | WO-2010/043049 A1 | 4/2010 |
| WO | WO 2010/063122 | 6/2010 |

(56) References Cited

FOREIGN PATENT DOCUMENTS

| | | |
|---|---|---|
| WO | WO 2010/063123 | 6/2010 |
| WO | WO 2010/063124 | 6/2010 |
| WO | WO 2010/069074 | 6/2010 |
| WO | WO 2010/121379 | 10/2010 |
| WO | WO 2010/142035 | 12/2010 |
| WO | WO 2011/000095 | 1/2011 |
| WO | WO-2011/008823 A2 | 1/2011 |
| WO | WO 2011/041897 | 4/2011 |
| WO | WO-2011/063507 A1 | 6/2011 |
| WO | WO-2011/112635 A1 | 9/2011 |
| WO | WO 2011/153642 | 12/2011 |
| WO | WO 2012/000118 | 1/2012 |
| WO | WO-2012/006239 A1 | 1/2012 |
| WO | WO 2012/037687 | 3/2012 |
| WO | WO-2012/064973 A2 | 5/2012 |
| WO | WO-2012/068531 A2 | 5/2012 |
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/153286 A1 | 11/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013/023184 A1 | 2/2013 |
| WO | WO-2013/032591 A1 | 3/2013 |
| WO | WO-2013/049332 A1 | 4/2013 |
| WO | WO-2013/056096 A1 | 4/2013 |
| WO | WO-2013/063468 A1 | 5/2013 |
| WO | WO-2013/071272 A1 | 5/2013 |
| WO | WO-2013/078562 A2 | 6/2013 |
| WO | WO-2013/078564 A2 | 6/2013 |
| WO | WO-2013/090861 A1 | 6/2013 |
| WO | WO-2013/120107 A1 | 8/2013 |
| WO | WO-2013/131032 A1 | 9/2013 |
| WO | WO-2013/151774 A1 | 10/2013 |
| WO | WO-2013/162757 A1 | 10/2013 |
| WO | WO-2013/185235 A1 | 12/2013 |

OTHER PUBLICATIONS

Comereski et al., Toxicologic Pathology, 1994, vol. 22, No. 5, 473-488.*

Ballabh et al., "The Blood-Brain Barrier: An Overview Structure, Regulation, and Clinical Implications," *Neurobiol Dis.* 16:1-13 (2004).

Bickel et al., "Delivery of Peptides and Proteins Through the Blood-Brain Barrier," *Adv Drug Deliv Rev.* 46:247-279 (2001).

Boado, "Blood-brain Barrier Transport of Non-viral Gene and RNAi Therapeutics," *Pharm Res.* 24:1772-1787 (2007).

Bork, "Powers and Pitfalls in Sequence Analysis: The 70% Hurdle," *Genome Res.* 10:398-400 (2000).

Bork et al., "Go Hunting in Sequence Databases But Watch Out for the Traps," *Trends Genet.* 12:425-427 (1996).

Brenner, "Errors in Genome Annotation," *Trends Genet.* 15:132-133 (1999).

Castex et al., "2-Pyrrolinodoxorubicin and Its Peptide-vectorized Form Bypass Multidrug Resistance," *Anticancer Drugs.* 15:609-617 (2004).

Coon et al., "Solutol HS 15, Nontoxic Polyoxyethylene Esters of 12-hydroxystearic Acid, Reverses Multidrug Resistance," *Cancer Res.* 51:897-902 (1991).

D'Onofrio et al., "Glycomimetics as Decorating Motifs for Oligonucleotides: Solid-phase Synthesis, Stability, and Hybridization Properties of Carbopeptoid-oligonucleotide Conjugates," *Bioconjug Chem.* 16:1299-1309 (2005).

Dagenais et al., "Development of an in Situ Mouse Brain Perfusion Model and Its Application to mdr1a P-glycoprotein-deficient Mice," *J Cereb Blood Flow Metab.* 20:381-386 (2000).

Deane et al., "LRP/Amyloid β-Peptide Interaction Mediates Differential Brain Efflux of Aβ Isoforms," *Neuron.* 43:333-344 (2004).

Dehouck et al., "A New Function for the LDL Receptor: Transcytosis of LDL Across the Blood-Brain Barrier," *J Cell Biol.* 138:877-889 (1997).

Dehouck et al., "An Easier, Reproducible, and Mass-production Method to Study the Blood-brain Barrier in Vitro," *J Neurochem.* 54:1798-1801 (1990).

Dehouck et al., "Drug Transfer Across the Blood-Brain Barrier: Correlation Between in Vitro and in Vivo Models," *J Neurochem.* 58:1790-1797 (1992).

Demeule et al., "High Transcytosis of Melanotransferrin (P97) Across the Blood-Brain Barrier," *J Neurochem.* 83:924-933 (2002).

Demeule et al., "Identification and Design of Peptides As a New Drug Delivery System for the Brain," *J Pharmacol Exp Ther.* 324:1064-1072 (2008).

Demeule et al., "Isolation of Endothelial Cells from Brain, Lung, and Kidney: Expression of the Multidrug Resistance P-Glycoprotein Isoforms," *Biochem Biophys Res Commun.* 281:827-834 (2001).

Doerks et al., "Protein Annotation: Detective Work for Function Prediction," *Trends Genet.* 14:248-250 (1998).

Fillebeen et al., "Receptor-Mediated Transcytosis of Lactoferrin Through the Blood-Brain Barrier," *J Biol Chem.* 274:7011-7017 (1999).

Fromm, "P-glycoprotein: A Defense Mechanism Limiting Oral Bioavailability and CNS Accumulation of Drugs," *Int J Clin Pharmacol Ther.* 38:69-74 (2000).

Gelmon, "The Taxoids: Paclitaxel and Docetaxel," *Lancet.* 344:1267-1272 (1994).

Gewirtz, "A Critical Evaluation of the Mechanisms of Action Proposed for the Antitumor Effects of the Anthracycline Antibiotics Adriamycin and Daunorubicin," *Biochem Pharmacol.* 57:727-741 (1999).

Grabb et al., "Neoplastic and Pharmacological Influence on the Permeability of an in vitro Blood-Brain Barrier," *J Neurosurg.* 82:1053-1058 (1995).

Guillot et al., "Angiotensin Peptide Regulation of Bovine Brain Microvessel Endothelial Cell Monolayer Permeability," *J Cardiovasc Pharmacol.* 18:212-218 (1991).

Gumbleton et al., "Progress and Limitations in the Use of In Vitro Cell Cultures to Serve as a Permeability Screen for the Blood-Brain Barrier," *J Pharm Sci.* 90:1681-1698 (2001).

Hawkins et al., "The Blood-Brain Barrier/Neurovascular Unit in Health and Disease," *Pharmacol Rev.* 57:173-185 (2005).

Hussain et al., "The Mammalian Low-Density Lipoprotein Receptor Family," *Annu Rev Nutr.* 19:141-172 (1999).

Ito et al., "Functional Characterization of the Brain-to-Blood Efflux Clearance of Human Amyloid-β Peptide (1-40) Across the Rat Blood-Brain Barrier," *Neurosci Res.* 56:246-252 (2006).

Ke et al., "Gene Delivery Targeted to the Brain Using an Angiopep-conjugated Polyethyleneglycol-modified Polyamidoamine Dendrimer," *Biomaterials.* 30:6976-6985 (2009).

Kiernan et al., "Fluorescent—Labelled Aprotinin: A New Reagent for the Histochemical Detection of Acid Mucosubstances," *Histochemie.* 34: 77-84 (1973).

Kobayashi et al., "The Protease Inhibitor Bikunin, a Novel Anti-Metastatic Agent," *Biol Chem.* 384:749-754 (2003).

Koo et al., "Differential Expression of Amyloid Precursor Protein mRNAs in Cases of Alzheimer's Disease and in Aged Nonhuman Primates," *Neuron.* 2:97-104 (1990).

Kounnas et al, "LDL Receptor-related Protein, a Multifunctional ApoE Receptor, Binds Secreted Beta-amyloid Precursor Protein and Mediates Its Degradation," *Cell.* 82:331-340 (1995).

Koziara et al., "In Situ Blood-brain Barrier Transport of Nanoparticles," *Pharm Res.* 20:1772-1778 (2003).

Kreuter et al., "Apolipoprotein-Mediated Transport of Nanoparticle-Bound Drugs Across the Blood-Brain Barrier," *J Drug Target.* 10:317-325 (2002).

Kreuter et al., "Direct Evidence that Polysorbate-80-coated Poly(Butylcyanoacrylate) Nanoparticles Deliver Drugs to the CNS Via Specific Mechanisms Requiring Prior Binding of Drug to the Nanoparticles," *Pharm Res.* 20:409-416 (2003).

Kreuter, "Nanoparticulate Carriers for Drug Delivery to the Brain," *Nanoparticles as Drug Carriers*, Torchilin VP, Imperial College Press, London pp. 527-547 (2006).

(56) References Cited

OTHER PUBLICATIONS

Laccabue et al., "A Novel Taxane Active against an Orthotopically Growing Human Glioma Xenograft," *Cancer*. 92:3085-3092 (2001).
Lai et al., "The Critical Component to Establish in vitro BBB Model: Pericyte," *Brain Res Rev*. 50:258-265 (2005).
Larionova et al., "Carbohydrate-Containing Derivatives of the Trypsin-Kallikrein Inhibitor Aprotinin from Bovine Organs II. Inhibitor Coupled to the (Carboxymethyl)dextran Derivatives of D-Galactose," *Biol Chem Hoppe-Seyler*. 366:743-748 (1985).
Larsson, "Megalin, an Endocytotic Receptor With Signalling Potential," *Acta Universitatis Upsaliensis Uppsala* 1-60 (2006).
Ma et al., "Cationic Charge-Dependent Hepatic Delivery of Amidated Serum Albumin," *J Control Release*. 102:583-594 (2005).
Marinò et al., "Megalin-Mediated Transcytosis of Thyroglobulin by Thyroid Cells is a Calmodulin-Dependent Process," *Thyroid*. 10:461-469 (2000).
Marinò et al., "Transcytosis of Retinol-Binding Protein Across Renal Proximal Tubule Cells After Megalin (gp 330)-Mediated Endocytosis," *J Am Soc Nephrol*.12:637-648 (2001).
Martel et al., "Transport of Apolipoproteins E and J at the Blood-Brain Barrier Relevance to Alzheimer's disease," *S.T.P. Pharma Sciences*. 7:28-36 (1997).
Mazel et al., "Doxorubicin-peptide Conjugates Overcome Multidrug Resistance," *Anticancer Drugs*. 12:107-116 (2001).
McCarty, "Cell Biology of the Neurovascular Unit: Implications for Drug Delivery Across the Blood-Brain Barrier," *Assay Drug Dev Technol*. 3:89-95 (2005).
Moestrup et al., "Evidence that Epithelial Glycoprotein 330/Megalin Mediates Uptake of Polybasic Drugs," *J.Clin. Invest*. 96:1404-1413 (1995).
Moore et al., "The Role of Flexible Tethers in Multiple Ligand-receptor Bond Formation Between Curved Surfaces," *Biophys J*. 91:1675-1687 (2006).
Muratovska et al., "Conjugate for Efficient Delivery of Short Interfering RNA (siRNA) Into Mammalian Cells," *FEBS Lett*. 558:63-68 (2004).
Ngo et al., "Computational Complexity; Protein Structure Prediction, and the Levinthal Paradox," *The Protein Folding Problem and Tertiary Structure Prediction* Merz, Jr. and Le Grand, Eds. 491-495 (1994).
Niola et al., "A Plasmid-encoded VEGF siRNA Reduces Glioblastoma Angiogenesis and Its Combination with Interleukin-4 Blocks Tumor Growth in a Xenograft Mouse Model," *Cancer Biol Ther*. 5:174-179 (2006).
Orlando et al., "Identification of the Second Cluster of Ligand-Binding Repeats in Megalin as a Site for Receptor-Ligand Interactions," *Proc Natl Acad Sci*. 94:2368-2373 (1997).
Pan et al., "Efficient Transfer of Receptor-Associated Protein (RAP) Across the Blood-Brain Barrier," *J Cell Sci*. 117:5071-5078 (2004).
Pardridge, "Blood-Brain Barrier Biology and Methodology," *J Neurovirol*. 5:556-569 (1999).
Pardridge, "CNS Drug Design Based on Principles of Blood-Brain Barrier Transport," *J Neurochem*. 70:1781-1792 (1998).
Pardridge, "Drug Targeting to the Brain," *Pharm Res*. 24:1733-1744 (2007).
Peri et al., "D-Glucose as a Regioselectively Addressable Scaffold for Combinatorial Chemistry on Solid Phase," *J Carbohydr Chem*. 22:57-71 (2003).
Prince et al., "Lipoprotein Receptor Binding, Cellular Uptake, and Lysosomal Delivery of Fusions Between the Receptor-Associated protein (RAP) and α-L-Iduronidase or Acid α-Glucosidase," *J Biol Chem*. 279:35037-35046 (2004).
Qu et al., "Carbohydrate-based Micelle Clusters Which Enhance Hydrophobic Drug Bioavailability by Up to 1 Order of Magnitude," *Biomacromolecules*. 7:3452-3459 (2006).
Ramakrishnan, "The Role of P-glycoprotein in the Blood-Brain Barrier," *Einstein Q J Biol Med*. 19:160-165 (2003).
Rawat et al., "Lipid Carriers: A Versatile Delivery Vehicle for Proteins and Peptides," *Yakugaku Zasshi*. 128:269-280 (2008).
Régina et al., "Antitumour Activity of ANG1005, a Conjugate Between Paclitaxel and the New Brain Delivery Vector Angiopep-2," *Br J Pharmacol*. 155:185-197 (2008).
Régina et al., "Differences in Multidrug Resistance Phenotype and Matrix Metalloproteinases Activity Between Endothelial Cells from Normal Brain and Glioma," *J Neurochem*. 84:316-324 (2003).
Scherrmann, "Drug Delivery to Brain Via the Blood-Brain Barrier," *Vascul Pharmacol*. 38:349-354 (2002).
Schinkel, "P-Glycoprotein, A Gatekeeper in the Blood-Brain Barrier," *Adv Drug Deliv Rev*. 36:179-194 (1999).
Seidel et al., "Effects of Trasylol on the Blood-Brain Barrier in Rats," *Naunyn Schmiedebergs Arch Pharmacol*. 284:R73 (1974).
Shibata et al., "Clearance of Alzheimer's Amyloid-$\beta_{1-40}$ Peptide From Brain by LDL Receptor-Related Protein-1 at the Blood-Brain Barrier," *J Clin Invest*. 106:1489-1499 (2000).
Shiiki et al., "Brain Insulin Impairs Amyloid-$\beta$(1-40) Clearance From the Brain," *J Neurosci*. 24:9632-9637 (2004).
Shimura et al., "Transport Mechanism of a New Behaviorally Highly Potent Adrenocorticotropic Hormone (ACTH) Analog, Ebiratide, through the Blood-Brain Barrier," *J Pharmacol Exp Ther*. 258:459-465 (1991).
Skolnick et al., "From Genes to Protein Structure and Function: Novel Applications of Computational Approaches in the Genomic Era," *Trends Biotechnol*. 18:34-39 (2000).
Smith, "Brain Perfusion Systems for Studies of Drug Uptake and Metabolism in the Central Nervous System," *Pharm Biotechnol*. 285-307 (1996).
Smith et al., "The Challenges of Genome Sequence Annotation or 'The Devil is in the Details'," *Nat Biotechnol*. 15:1222-1223 (1997).
Steiniger et al., "Chemotherapy of Glioblastoma in Rats Using Doxorubicin-loaded Nanoparticles," *Int J Cancer*. 109:759-767 (2004).
Tamai et al., "Structure-Internalization Relationship for Adsorptive-Mediated Endocytosis of Basic Peptides at the Blood-Brain Barrier," *J Pharmacol Exp Ther*. 280:410-415 (1997).
Temsamani et al., "Vector-Mediated Drug Delivery to the Brain," *Expert Opin Biol Ther*. 1:773-782 (2001).
Terasaki et al., "New Approaches to in vitro Models of Blood-Brain Barrier Drug Transport," *Drug Discov Today*. 8:944-954 (2003).
Triguero et al., "Capillary Depletion Method for Quantification of Blood-Brain Barrier Transport of Circulating Peptides and Plasma Proteins," *J Neurochem*. 54:1882-1888 (1990).
Turner et al., "RNA Targeting With Peptide Conjugates of Oligonucleotides, siRNA and PNA," *Blood Cells Mol Dis*. 38:1-7 (2007).
Veronese et al., "PEGylation, Successful Approach to Drug Delivery," *Drug Discov Today*. 10:1451-1458 (2005).
Wang et al., "DNA/dendrimer Complexes Mediate Gene Transfer into Murine Cardiac Transplants ex Vivo," *Mol Ther*. 2:602-608 (2000).
Wells, "Additivity of Mutational Effects in Proteins," *Biochemistry*. 29:8509-8517 (1990).
Witt et al., "Peptide Drug Modifications to Enhance Bioavailability and Blood-Brain Barrier Permeability," *Peptides*. 22:2329-2343 (2001).
Xu et al., "In Vitro and in Vivo Evaluation of Actively Targetable Nanoparticles for Paclitaxel Delivery," *Int J Pharm*. 288:361-368 (2005).
Yepes et al., "Tissue-Type Plasminogen Activator Induces Opening of the Blood-Brain Barrier Via the LDL Receptor-Related Protein," *J Clin Invest*. 112:1533-1540 (2003).
Zhang et al., "Intravenous RNA Interference Gene Therapy Targeting the Human Epidermal Growth Factor Receptor Prolongs Survival in Intracranial Brain Cancer," *Clin Cancer Res*. 10:3667-3677 (2004).
Zhang et al., "Silencing the Epidermal Growth Factor Receptor Gene with RNAi may be Developed as a Potential Therapy for Non Small Cell Lung Cancer," *Genet Vaccines Ther*. 3:5 (2005).
Zhang et al., "siRNA-containing Liposomes Modified with Polyarginine Effectively Silence the Targeted Gene," *J Control Release*. 112:229-239 (2006).
Zlokovic et al., "Glycoprotein 330/Megalin: Probable Role in Receptor-mediated Transport of Apolipoprotein J Alone and in a Complex

(56) References Cited

OTHER PUBLICATIONS

With Alzheimer Disease Amyloid β at the Blood-Brain and Blood-Cerebrospinal Fluid Barriers," *Proc Natl Acad Sci U S A*. 93:4229-4234 (1996).
Arpicco et al., "New Coupling Reagents for the Preparation of Disulfide Cross-Linked Conjugates with Increased Stability," *Bioconjugate Chem*. 8:327-337 (1997).
Banks, "Leptin Transport Across the Blood-Brain Barrier: Implications for the Cause and Treatment of Obesity," *Curr. Pharm. Des*. 7:125-133 (2001).
Banks, "The Blood-Brain Barrier as a Cause of Obesity," *Curr. Pharm. Des*. 14:1606-1614 (2008).
Bicamumpaka et al., "In Vitro Cytotoxicity of Paclitaxel-Transferrin Conjugate on H69 Cells," *Oncol. Rep*. 5:1381-1383 (1998).
Demeule et al., "Drug Transport to the Brain: Key Roles for the Efflux Pump P-Glycoprotein in the Blood-Brain Barrier," *Vascul. Pharmacol*. 38:339-348 (2002).
Dooley et al., "An All D-amino Acid Opioid Peptide with Central Analgesic Activity from a Combinatorial Library," *Science* 266:2019-2022 (1994).
Eigenbrot et al., "X-Ray Structure of Glial Cell-Derived Neurotrophic Factor at 1.9 Å Resolution and Implications for Receptor Binding," *Nat. Struct. Biol*. 4:435-438 (1997).
Gabius et al., "Targeting of Neoglycoprotein-Drug Conjugates to Cultured Human Embryonal Carcinoma Cells,"*J. Cancer Res. Clin. Oncol*. 113:126-130 (1987).
Gottschalk et al., "Protein Self-Association in Solution: The Bovine Pancreatic Trypsin Inhibitor Decamer," *Biophys. J*. 84: 3941-3958 (2003).
U.S. Appl. No. 12/601,803, filed Nov. 24, 2009, Beliveau et al.
U.S. Appl. No. 12/632,557, filed Dec. 7, 2009, Castaigne et al.
Akhtar et al., "Nonviral Delivery of Synthetic siRNAs in Vivo," *J. Clin. Invest*. 117: 3623-3632 (2007).
Anonymous, "Blood-Brain Barrier Tackled," <http:www.ecancermedicalscience.com/news-insider-news.asp?itemId=326> Oct. 22, 2008.
Bertrand et al., "Transport Characteristics of a Novel Peptide Platform for CNS Therapeutics," *J. Cell Mol. Med*. published online Oct. 10, 2009.
Boules et al., "Bioactive Analogs of Neurotensin: Focus on CNS Effects," *Peptides* 27: 2523-2533 (2006).
Chari, "Targeted Cancer Therapy: Conferring Specificity to Cytotoxic Drugs," *Acc. Chem. Res*. 41:98-107 (2008).
Ché et al., "New Angiopep-Modified Doxorubicin (ANG1007) and Etoposide (ANG1009) Chemotherapeutics with Increased Brain Penetration," *J. Med. Chem*. 53: 2814-2824 (2010).
Demeule et al., "Involvement of the Low-Density Lipoprotein Receptor-Related Protein in the Transcytosis of the Brain Delivery Vector Angiopep-2," *J. Neurochem*. 106: 1534-1544 (2008).
Garsky et al., "The Synthesis of a Prodrug of Doxorubicin Designed to Provide Reduced Systemic Toxicity and Greater Target Efficacy," *J. Med. Chem*. 44: 4216-4224 (2001).
Huang et al., "Targeting Delivery of Paclitaxel into Tumor Cells via Somatostatin Receptor Endocytosis," *Chem. Biol*. 7: 453-461 (2000).
Harkavyi et al., "Glucagon-Like Peptide 1 Receptor Stimulation Reverses Key Deficits in Distinct Rodent Models of Parkinson's Disease," *J. Neuroinflammation*. 5:19 (2008) (pp. 1-9).
Kalra, "Central Leptin Insufficiency Syndrome: An Interactive Etiology for Obesity, Metabolic and Neural Diseases and for Designing New Therapeutic Interventions," *Peptides* 29:127-138 (2008).
Karyekar et al., "*Zonula Occludens* Toxin Increases the Permeability of Molecular Weight Markers and Chemotherapeutic Agents Across the Bovine Brain Microvessel Endothelial Cells," *J. Pharm. Sci*. 92:414-423 (2003).
Kirsch et al., "Anti-Angiogenic Treatment Strategies for Malignant Brain Tumors," *J. Neurooncol*. 50:149-163 (2000).
Lewis et al., "Maleimidocysteineamido-DOTA Derivatives: New Reagents for Radiometal Chelate Conjugation to Antibody Sulfhydryl Groups Undergo pH-Dependent Cleavage Reactions," *Bioconjugate Chem*. 9:72-86 (1998).
Saito et al., "Drug Delivery Strategy Utilizing Conjugation Via Reversible Disulfide Linkages: Role and Site of Cellular Reducing Activities," *Adv. Drug. Deliv. Rev*. 55:199-215 (2003).
Samson et al., "Gene Therapy for Diabetes: Metabolic Effects of Helper-Dependent Adenoviral Exendin 4 Expression in a Diet-Induced Obesity Mouse Model," *Mol. Ther*. 16:1805-1812 (2008) (pp. 1-18).
Uekita et al., "Cytoplasmic Tail-Dependent Internalization of Membrane-Type 1 Matrix Metalloproteinase is Important for its Invasion-Promoting Activity," *J. Cell. Biol*. 155:1345-1356 (2001).
Uekita et al., "Membrane-Type 1 Matrix Metalloproteinase Cytoplasmic Tail-Binding Protein-1 is a New Member of the Cupin Superfamily. A Possible Multifunctional Protein Acting as an Invasion Suppressor Down-Regulated in Tumors," *J. Biol. Chem*. 279:12734-12743 (2004).
Kilic et al., "Intravenous TAT-GDNF is Protective after Focal Cerebral Ischemia in Mice," *Stroke* 34: 1304-1310 (2003).
Kumar et al., "Transvascular Delivery of Small Interfering RNA to the Central Nervous System," *Nature* 448: 39-43 (2007).
Rouselle et al., "New Advances in the Transport of Doxorubicin through the Blood-Brain Barrier by a Peptide Vector-Mediated Strategy," *Mol. Pharmacol*. 57: 679-686 (2000).
Takei et al., "A Small Interfering RNA Targeting Vascular Endothelial Growth Factor as Cancer Therapeutics," *Cancer Res*. 64: 3365-3370 (2004).
Trail et al., "Cure of Xenografted Human Carcinomas by BR96-Doxorubicin Immunoconjugates," *Science* 261:212-215 (1993).
U.S. Appl. No. 61/546,851, filed Oct. 13, 2011, Demeule et al.
Grimm et al., "Ten Year Biochemical Outcomes Following 125-Iodine Monotherapy for Early Stage Prostate Cancer." *Int. J. Rad. Oncol. Biol. Phys*. 48:146-147 (2000).
Kurzrock et al., "ANGI005: Results of a Phase I study in patients with advanced solid tumors and metastatic brain cancer" Poster B168, ACCR/NCI/EORTC Annual Meeting, 2009.
Mathupala, "Delivery of Small-interfering RNA (siRNA) to the Brain," *Exp. Opin. Ther. Pat*. 19: 137-140, (2009).
Nyalendo et al., "Impaired Tyrosine Phosphorylation of Membrane type 1-Matrix Metalloproteinase Reduces Tumor Cell Proliferation in Three-Dimensional Matrices and Abrogates Tumor Growth in Mice," *Carcinogenesis* 29:1655-1664, (2008).
Sadeghi-aliabadi et al., "Solvent optimization on Taxol extraction from *Taxus baccata* L., using HPLC and LC-MS," *DARU* 17:192-198, (2009).
Schiff and Horwitz, "Taxol Stabilizes Microtubules in Mouse Fibroblast Cells," *Proc Natl Acad Sci USA* 77:1561-1565, (1980).
Tilstra et al., "Protein Transduction: Identification, Characterization and Optimization," *Biochem. Soc. Trans*. 35:811-815, (2007).
Zhang et al., "Tat-modified Leptin is more Accessible to Hypothalamus Through Brain-blood Barrier with a Significant Inhibition of Body-weight Gain in High-fat-diet Fed Mice," *Exp. Clin. Endocrin. Diabet*. 118:31-37 (2010).
International Search Report and Written Opinion of the International Searching Authority for Application No. PCT/CA2009/001481, dated Jan. 5, 2010.
Brady et al., "Reflections on a peptide," *Nature* 368:692-693 (1994).
Carell et al., "A novel procedure for the synthesis of libraries containing small organic molecules," *Angew Chem Int Ed Engl*. 33(20):2059-2061 (1994).
Carell et al., "A solution-phase screening procedure for the isolation of active compounds from a library of molecules," *Angew Chem Int Ed Engl*. 33(20):2061-2064 (1994).
Chen et al., "Synthesis of doxorubicin conjugates through hydrazone bonds to melanotransferrin P97," *Synth Commun*. 33(14):2377-2390 (2003).
Cho et al., "An unnatural biopolymer," *Science* 261:1303-1305 (1993).
Cull et al., "Screening for receptor ligands using large libraries of peptides linked to the C terminus of the *lac* repressor," *Proc Natl Acad Sci USA* 89:1865-1869 (1992).
DeWitt et al., ""Diversomers": an approach to nonpeptide, nonoligomeric chemical diversity," *Proc Natl Acad Sci USA* 90:6909-6913 (1993).

(56) References Cited

OTHER PUBLICATIONS

Evans et al., "Design of nonpeptidal ligands for a peptide receptor: Cholecystokinin antagonists," *J Med Chem.* 30(7):1229-1239 (1987).
Erb et al., "Recursive deconvolution of combinatorial chemical libraries," *Proc Natl Acad Sci USA* 91:11422-11426 (1994).
Fauchere et al., "Association with HeLa cells of *Campylobacter jejuni* and *Campylobacter coli* isolated from human feces," *Infect Immun.* 54(2):283-287 (1986).
Fioretti et al "Aprotinin-like isoinhibitors in bovine organs," *Biol Chem Hoppe-Seyler* 369(Suppl):37-42 (1988).
Fodor et al., "Multiplexed biochemical assays with biological chips," *Nature* 364:555-556 (1993).
Furuta et al., "Structure-antinociceptive activity studies with neurotensin," *Br J Pharmacol.* 83:43-48 (1984).
Gallop et al., "Applications of combinatorial technologies to drug discovery. 1. Background and peptide combinatorial libraries,"*J Med Chem.* 37(9):1233-1251 (1994).
Halab et al., "Design, synthesis, and conformational analysis of azacycloalkane amino acids as conformationally constrained probes for mimicry of peptide secondary structures," *Biopolymers* 55:101-122 (2000).
Hanessian et al., "Synthesis of (4S)-hydroxymethyl-(2R)-(2-propyl)-butyrolactone: a quest for a practical route to an important hydroxyethylene isostere chiron," *Tetrahedron* 53(18):6281-6294 (1997).
Pardridge et al., "Selective transport of an anti-transferrin receptor antibody through the blood-brain barrier in vivo," *J Pharmacol Exp Ther.* 259(1):66-70 (1991).
Pardridge, "Vector-mediated drug delivery to the brain," *Adv Drug Deliv Rev.* 36:299-321 (1999).
Pardridge et al., "Combined use of carboxyl-directed protein pegylation and vector-mediated blood-brain barrier drug delivery system optimizes brain uptake of brain-derived neurotrophic factor following intravenous administration," *Pharm Res.* 15(4):576-582 (1998).
Powell et al., "Peptide stability in drug development. II. Effect of single amino acid substitution and glycosylation on peptide reactivity in human serum," *Pharm Res.* 10(9):1268-1273 (1993).
Rizo et al., "Constrained peptides: models of bioactive peptides and protein substructures," *Annu Rev Biochem.* 61:387-418 (1992).
Scott et al., "Searching for peptide ligands with an epitope library," *Science* 249:386-390 (1990).
Spatola et al., "Structure-activity relationships of enkephalins containing serially replaced thiomethylene amide bond surrogates," *Life Sci.* 38(14):1243-1249 (1986).
Tilstra et al., "Protein transduction: identification, characterization and optimization," *Biochem Soc Trans.* 35(4):811-815 (2007).
Wang et al., "Polyamidoamine dendrimers with a modified Pentaerythritol core having high efficiency and low cytotoxicity as gene carriers," *Biomacromolecules* 10(3):617-622 (2009).
Wang at al., "Synthesis and antinociceptive effects of endomorphin-1 analogs with C-terminal linked by oligoarginine," *Peptides* 32:293-299 (2011).
Williamson et al., "Expression and purification of recombinant neurotensin in *Escherichia coli*," *Protein Expr Purif.* 19:271-275 (2000).
Yano et al., "Simultaneous activation of two different receptor systems by enkephalin/neurotensin conjugates having spacer chains of various lengths," *Eur J Pharm Sci.* 7:41-48 (1998).
Author manuscript of Howes et al., "Rapid induction of therapeutic hypothermia using convective-immersion surface cooling: Safety, efficacy and outcomes," published in final edited form as: *Resuscitation* 81:388-392 (2010).
Langer, "New methods of drug delivery," *Science* 249:1527-1533 (1990).
Rudikoff et al., "Single amino acid substitution altering antigen-binding specificity," *Proc Natl Acad Sci USA* 79:1979-1983 (1982).
Author manuscript of Hein et al:, "Click chemistry, a powerful tool for pharmaceutical sciences," published in final edited form as: *Pharm Res* 25(10):2216-2230 (2008).

Huang et al., "Production of bioactive human beta-defensin 5 and 6 in *Escherichia coli* by soluble fusion expression," *Protein Expr Purif.* 61:168-174 (2008).
Hudson et al., "Methionine enkephaline and isosteric analogues. I. Synthesis on a phenolic resin support," *Int J Pept Protein Res.* 14:177-185 (1979).
Jameson et al., "A rationally designed CD4 analogue inhibits experimental allergic encephalomyelitis," *Nature* 368:744-746 (1994).
Park et al., "Recombinant expression of biologically active rat leptin in *Escherichia coli*," *Protein Expr Purif.* 22:60-69 (2001).
Kurzrock et al., "ANG1005, an Angiopep-2/paclitaxel conjugate: The first clinical trial in patients with advanced cancer and brain metastases: Preliminary safety and tolerability data," 20th EORTC-NCI-AACR Symposium on "Molecular Targets and Cancer Therapeutics", *European Journal of Cancer including EJC Supplements* 6 12 :133, Abstract 424 (2008).
Lam, "Application of combinatorial library methods in cancer research and drug discovery," *Anticancer Drug Des.* 12:145-167 (1997).
Lam et al., "A new type of synthetic peptide library for identifying ligand-binding activity," *Nature* 354:82-84 (1991).
Markman et al., "Phase II trial of weekly single-agent paclitaxel in platinum/paclitaxel-refractory ovarian cancer," *J Clin Oncol.* 20:2365-2369 (2002).
Michaud et al., "Risks and benefits of taxanes in breast and ovarian cancer," *Drug Saf.* 23(5):401-428 (2000).
Rose et al., "Metastatic patterns in histologic variants of ovarian cancer. An autopsy study," *Cancer* 64:1508-1513 (1989).
Boado et al., "GDNF fusion protein for targeted-drug delivery across the human blood-brain barrier," *Biotechnol Bioeng.* 100(2):387-396 (2008).
Seiden et al., "A phase II study of the MDR inhibitor biricodar (INCEL, VX-710) and paclitaxel in women with advanced ovarian cancer refractory to paclitaxel therapy," *Gynecol Oncol.* 86:302-310 (2002).
Pathan et al., "CNS drug delivery systems: novel approaches," *Recent Pat Drug Deliv Formul.* 3:71-89 (2009).
Zhang et al., "In vitro gene delivery using polyamidoamine dendrimers with a trimesyl core," *Biomacromolecules* 6:341-350 (2005).
U.S. Appl. No. 61/138,375, Beliveau et al.
Belkin et al., "Matrix-dependent proteolysis of surface transglutaminase by membrane-type metalloproteinase regulates cancer cell adhesion and locomotion," J Biol Chem. 276(21):18415-18422 (2001).
Buvanendran et al., "Recent advances in nonopioid analgesics for acute pain management," Tech Reg Anesth Pain Man. 11(1):19-26 (2007).
Chu et al., "Detection of soluble P-glycoprotein in culture media and extracellular fluids," Biochem Biophys Res Commun. 203(1):506-512 (1994).
Cui et al., "PAMAM-drug complex for delivering anticancer drug across blood-brain barrier in-vitro and in-vivo," Afr J Pharm Pharmocol. 3(5):227-233 (2009).
D'Ortho et al., "Membrane-type matrix metalloproteinases 1 and 2 exhibit broad-spectrum proteolytic capacities comparable to many matrix metalloproteinases," Eur J Biochem. 250(3): 751-757 (1997).
Declaration of Michel Demeule in European Patent Application No. 11010125 dated Sep. 24, 2012 (4 pages).
Demeule et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
Gabathuler, "Approaches to transport therapeutic drugs across the blood-brain barrier to treat brain diseases," Neurobiol Dis. 37(1):48-57 (2010).
Hijova, Matrix metalloproteinases: their biological functions and clinical implications, Bratisl Lek Listy. 106(3):127-132 (2005).
Hiraoka et al., "Matrix metalloproteinases regulate neovascularization by acting as pericellular fibrinolysins," Cell. 95(3):365-377 (1998).
Hong et al., "Coexpression of cyclooxygenase-2 and matrix metalloproteinases in human aortic atherosclerotic lesions,"Yonsei Med J. 41(1):82-88 (2000).

(56) References Cited

OTHER PUBLICATIONS

Hotary et al., "Membrane type I matrix metalloproteinase usurps tumor growth control imposed by the three-dimensional extracellular matrix," Cell. 114(1):33-45 (2003).
Imai et al., "Expression of membrane-type 1 matrix metalloproteinase and activation of progelatinase A in human osteoarthritic cartilage," Am J Pathol. 151(1):245-256 (1997).
Itoh et al., "MT1-MMP: a potent modifier of pericellular microenvironment," J Cell Physiol. 206(1):1-8 (2006).
Kajita et al., "Membrane-type 1 matrix metalloproteinase cleaves CD44 and promotes cell migration" J Cell Biol. 153(5):893-904 (2001).
Kamps et al., "Uptake of long-circulating immunoliposomes, directed against colon adenocarcinoma cells, by liver metastases of colon cancer," J Drug Target. 8(4):235-245 (2000).
Kesari et al., "Phase II study of temozolomide, thalidomide, and celecoxib for newly diagnosed glioblastoma in adults," Neuro Oncol. 10(3):300-308 (2008).
Kirpotin et al., "Sterically stabilized anti-HER2 immunoliposomes: design and targeting to human breast cancer cells in vitro," Biochemistry. 36(1):66-75 (1997).
Konttinen et al., "Analysis of 16 different matrix metalloproteinases (MMP-1 to MMP-20) in the synovial membrane: different profiles in trauma and rheumatoid arthritis" Ann Rheum Dis. 58(11):691-7 (1999).
Lachowicz et al., "Analgesic properties of a novel brain-penetrant Angiopep-2-neurotensin derivative (ANG2002) for treating chronic pain," Program No. 173.28/AA9 2012 Neuroscience Meeting Planner, New Orleans, LA: Society for Neuroscience (2012).
Mamot et al., "Epidermal growth factor receptor (EGFR)-targeted immunoliposomes mediate specific and efficient drug delivery to EGFR- and EGFRvIII-overexpressing tumor cells," Cancer Res. 63(12):3154-61 (2003).
Martinez-Fong et al., "Neurotensin-SPDP-poly-L-lysine conjugate: a nonviral vector for targeted gene delivery to neural cells," Molecular Brain Research 69:249-262 (1999).
Moase et al., "Anti-MUC-1 immunoliposomal doxorubicin in the treatment of murine models of metastatic breast cancer," Biochim Biophys Acta. 1510(1-2):43-55 (2001).
Nakada et al., "Expression and tissue localization of membrane-type 1, 2, and 3 matrix metalloproteinases in human astrocytic tumors," Am J Pathol. 154(2):417-28 (1999).
Nam et al., "Sterically stabilized anti-G(M3), anti-Le(x) immunoliposomes: targeting to B16BL6, HRT-18 cancer cells," Oncol Res. 11(1):9-16 (1999).
Nyalendo et al., "Src-dependent phosphorylation of membrane type I matrix metalloproteinase on cytoplasmic tyrosine 573: role in endothelial and tumor cell migration," J Biol Chem. 282(21):15690-9 (2007).
Office Action and its English Translation for Russian Patent Application No. 2011118055, dated Jun. 1, 2013 (6 pages).
Office Action for Chinese Application No. 200980150439.X, mailed Mar. 21, 2013 (22 pages).
Park et al., "Development of anti-p185HER2 immunoliposomes for cancer therapy," Proc Natl Acad Sci U S A. 92(5):1327-31 (1995).
Pei et al., "Transmembrane-deletion mutants of the membrane-type matrix metalloproteinase-1 process progelatinase A and express intrinsic matrix-degrading activity," J Biol Chem. 271(15):9135-9140 (1996).
Rajavashisth et al., "Membrane type 1 matrix metalloproteinase expression in human atherosclerotic plaques: evidence for activation by proinflammatory mediators," Circulation. 99(24):3103-9 (1999).
Sabeh et al. "Tumor cell traffic through the extracellular matrix is controlled by the membrane-anchored collagenase MT1-MMP," J Cell Biol. 167(4):769-81 (2004).
Sahm et al. "Receptor binding affinities and biological activities of linear and cyclic melanocortins in B16 murine melanoma cells expressing the native MC1 receptor," J Pharm Pharmacol. 48(2):197-200 (1996).
Shao et al., "Angiopep-2 modified PE-PEG based polymeric micelles for amphotericin B delivery targeted to the brain," J Control Release. 147(1):118-26 (2010).
Svenson et al., "Dendrimers in biomedical applications—reflections on the field," Adv Drug Deliv Rev. 57(15):2106-2129 (2005).
UniProt Consortium, "P08183 (MDR1_HUMAN)," <http://www.uniprot.org/uniprot/P08183>, retrieved on Sep. 18, 2013 (16 pages).
Vincent, "Neurotensin receptors: binding properties, transduction pathways, and structure," Cell Mol Neurobiol. 15(5):501-512 (1995).
Zhai et al. "Expression of membrane type 1 matrix metalloproteinase is associated with cervical carcinoma progression and invasion," Cancer Res. 65(15):6543-6550 (2005).
Castaigne et al., "425 Poster ANG1005: Preliminary clinical safety and tolerability in patients with recurrent malignant glioma," Eur J Cancer. 6(12):133-134 (2008).
Extended European Search Report for European Patent Application No. 09820163.5, dated May 26, 2014 (13 pages).
Gabathuler et al., "117 Poster ANG1005, Paclitaxel conjugated to the angiopep brain transport vector for the treatment of brain cancer: preclinical studies," Eur J Cancer. 6(12):38-9 (2008).
Gabathuler et al., "147 Poster a new Taxol delivery system for the treatment of brain primary or metastatic tumors," Eur J Cancer. 4(12):47-8 (2006).
Gaillard et al., "Targeted delivery across the blood-brain barrier," Expert Opin Drug Deliv. 2(2):299-309 (2005).
Kurzrock et al., "424 Poster ANG1005, an Angiopep-2/paclitaxel conjugate: the first clinical trial in patients with advanced cancer and brain metastases: Preliminary safety and tolerability data," Eur J Cancer. 6(12):133 (2008).
Mazza et al., "Cancer and the blood-brain barrier: 'Trojan horses' for courses?" Br J Pharmacol. 155(2):149-51 (2008).
Nagy et al., "Targeting of cytotoxic luteinizing hormone-releasing hormone analogs to breast, ovarian, endometrial, and prostate cancers," Biol Reprod. 73(5):851-9 (2005).

* cited by examiner

Mice (n=5 per group) were treated once a week for 3 weeks

|  | $K_{in}$ (ml/100g/min) |
|---|---|
| Etoposide-Angiopep-2: | 8.26 |
| Etoposide: | 0.54 |
| $K_{in}$ ratio : | 15.3 |

——— Etoposide-Angiopep-2(3:1)

——— Etoposide (unconjugated)

(4A)

(4B)

Estimated bioavailability after i.p. administration $(AUC_{i.p.}/AUC_{i.v.}) \times 100 = (5.1/11) \times 100 = 46\%$

SEQUENCE LISTING

<160> NUMBER OF SEQ ID NOS: 116

<210> SEQ ID NO 1
<211> LENGTH: 19
<212> TYPE: PRT
<213> ORGANISM: Artificial sequence
<220> FEATURE:
<223> OTHER INFORMATION: polypeptide

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial sequence

```
<220> FEATURE:
<223> OTHER INFORMATION: polypeptide

<400> SEQUENCE: 2

Thr Phe Gln Tyr Gly Gly Cys Met Gly Asn Gly Asn Phe Val Thr
1               5                   10                  15

Glu Lys Glu

<210> SEQ ID NO 3
<211> LENGTH: 19
<212> TYPE: PRT
<213> ORGANISM: Artificial sequence
<220> FEATURE:
<223> OTHER INFORMATION: polypeptide

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial sequence
<220> FEATURE:
<223> OTHER INFORMATION: polypeptide

<400> SEQUENCE: 4

Ser Phe Tyr Tyr Gly Gly Cys Leu Gly Asn Lys Asn Asn Tyr Leu Arg
1               5                   10                  15

Glu Glu Glu

<210> SEQ ID NO 5
<211> LENGTH: 19
<212> TYPE: PRT
<213> ORGANISM: Artificial sequence
<220> FEATURE:
<223> OTHER INFORMATION: polypeptide
<220> FEATURE:
<221> NAME/KEY: MISC_FEATURE
<223> OTHER INFORMATION: may be amidated

<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial sequence
<220> FEATURE:
<223> OTHER INFORMATION: polypeptide

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
<213> ORGANISM: Artificial sequence
<220> FEATURE:
```

<223> OTHER INFORMATION: polypeptide

<400> SEQUENCE: 7

Thr Phe Phe Tyr Gly Gly Cys Arg Ala Lys Lys Asn Asn Tyr Lys Arg
1               5                   10                  15

Ala Lys Tyr

<210> SEQ ID NO 8
<211> LENGTH: 19
<212> TYPE: PRT
<213> ORGANISM: Artificial sequence
<220> FEATURE:
<223> OTHER INFORMATION: polypeptide

<400> SEQUENCE: 8

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial sequence
<220> FEATURE:
<223> OTHER INFORMATION: polypeptide

<400> SEQUENCE: 9

Thr Phe Gln Tyr Gly Gly Cys Arg Ala Lys Arg Asn Asn Phe Lys Arg
1               5                   10                  15

Ala Lys Tyr

<210> SEQ ID NO 10
<211> LENGTH: 19
<212> TYPE: PRT
<213> ORGANISM: Artificial sequence
<220> FEATURE:
<223> OTHER INFORMATION: polypeptide

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19
<212> TYPE: PRT
<213> ORGANISM: Artificial sequence
<220> FEATURE:
<223> OTHER INFORMATION: polypeptide

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial sequence
<220> FEATURE:
<223> OTHER INFORMATION: polypeptide

```
<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial sequence
<220> FEATURE:
<223> OTHER INFORMATION: polypeptide

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial sequence
<220> FEATURE:
<223> OTHER INFORMATION: polypeptide

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial sequence
<220> FEATURE:
<223> OTHER INFORMATION: polypeptide

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial sequence
<220> FEATURE:
<223> OTHER INFORMATION: polypeptide

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial sequence
<220> FEATURE:
<223> OTHER INFORMATION: polypeptide
```

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial sequence
<220> FEATURE:
<223> OTHER INFORMATION: polypeptide

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
<213> ORGANISM: Artificial sequence
<220> FEATURE:
<223> OTHER INFORMATION: polypeptide

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial sequence
<220> FEATURE:
<223> OTHER INFORMATION: polypeptide

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial sequence
<220> FEATURE:
<223> OTHER INFORMATION: polypeptide

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
<213> ORGANISM: Artificial sequence
<220> FEATURE:
<223> OTHER INFORMATION: polypeptide

```
<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial sequence
<220> FEATURE:
<223> OTHER INFORMATION: polypeptide

<400> SEQUENCE: 23

Thr Phe Phe Tyr Gly Gly Cys Arg Gly Asn Arg Asn Phe Leu Arg
1               5                   10                  15

Ala Lys Tyr

<210> SEQ ID NO 24
<211> LENGTH: 19
<212> TYPE: PRT
<213> ORGANISM: Artificial sequence
<220> FEATURE:
<223> OTHER INFORMATION: polypeptide

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial sequence
<220> FEATURE:
<223> OTHER INFORMATION: polypeptide

<400> SEQUENCE: 25

Thr Phe Phe Tyr Gly Gly Ser Arg Gly Asn Arg Asn Asn Phe Lys Thr
1               5                   10                  15

Ala Lys Tyr

<210> SEQ ID NO 26
<211> LENGTH: 19
<212> TYPE: PRT
<213> ORGANISM: Artificial sequence
<220> FEATURE:
<223> OTHER INFORMATION: polypeptide

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19
<212> TYPE: PRT
<213> ORGANISM: Artificial sequence
<220> FEATURE:
<223> OTHER INFORMATION: polypeptide
```

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial sequence
<220> FEATURE:
<223> OTHER INFORMATION: polypeptide

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
<211> LENGTH: 19
<212> TYPE: PRT
<213> ORGANISM: Artificial sequence
<220> FEATURE:
<223> OTHER INFORMATION: polypeptide

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial sequence
<220> FEATURE:
<223> OTHER INFORMATION: polypeptide

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial sequence
<220> FEATURE:
<223> OTHER INFORMATION: polypeptide

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial sequence
<220> FEATURE:
<223> OTHER INFORMATION: polypeptide -continued

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial sequence
<220> FEATURE:
<223> OTHER INFORMATION: polypeptide

<400> SEQUENCE: 33

Thr Phe Phe Tyr Gly Gly Ser Arg Gly Lys Gly Asn Asn Phe Asp Arg
1               5                   10                  15

Ala Lys Tyr

<210> SEQ ID NO 34
<211> LENGTH: 19
<212> TYPE: PRT
<213> ORGANISM: Artificial sequence
<220> FEATURE:
<223> OTHER INFORMATION: polypeptide

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
<212> TYPE: PRT
<213> ORGANISM: Artificial sequence
<220> FEATURE:
<223> OTHER INFORMATION: polypeptide

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial sequence
<220> FEATURE:
<223> OTHER INFORMATION: polypeptide

<400> SEQUENCE: 36

Thr Phe Phe Tyr Gly Gly Cys Leu Gly Lys Gly Asn Asn Phe Leu Thr
1               5                   10                  15

Ala Lys Tyr

<210> SEQ ID NO 37
<211> LENGTH: 19
<212> TYPE: PRT
<213> ORGANISM: Artificial sequence
<220> FEATURE:
<223> OTHER INFORMATION: polypeptide

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial sequence
<220> FEATURE:
<223> OTHER INFORMATION: polypeptide

<400> SEQUENCE: 38

Thr Phe Phe Tyr Gly Gly Cys Gly Gly Asn Lys Asn Asn Phe Val Arg
1               5                   10                  15

Glu Lys Tyr

<210> SEQ ID NO 39
<211> LENGTH: 19
<212> TYPE: PRT
<213> ORGANISM: Artificial sequence
<220> FEATURE:
<223> OTHER INFORMATION: polypeptide

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
<211> LENGTH: 19
<212> TYPE: PRT
<213> ORGANISM: Artificial sequence
<220> FEATURE:
<223> OTHER INFORMATION: polypeptide

<400> SEQUENCE: 40

Thr Phe Phe Tyr Gly Gly Ser Met Gly Asn Lys Asn Asn Phe Val Arg
1               5                   10                  15

Glu Lys Tyr

<210> SEQ ID NO 41
<211> LENGTH: 19
<212> TYPE: PRT
<213> ORGANISM: Artificial sequence
<220> FEATURE:
<223> OTHER INFORMATION: polypeptide

<400> SEQUENCE: 41

Pro Phe Phe Tyr Gly Gly Cys Leu Gly Asn Arg Asn Asn Tyr Val Arg
1               5                   10                  15

Glu Lys Tyr

<210> SEQ ID NO 42
<211> LENGTH: 19
<212> TYPE: PRT
<213> ORGANISM: Artificial sequence
<220> FEATURE:
<223> OTHER INFORMATION: polypeptide

<400> SEQUENCE: 42

Thr Phe Phe Tyr Gly Gly Cys Leu Gly Asn Arg Asn Phe Val Arg
1               5                   10                  15

Glu Lys Tyr

<210> SEQ ID NO 43
<211> LENGTH: 19
<212> TYPE: PRT
<213> ORGANISM: Artificial sequence
<220> FEATURE:
<223> OTHER INFORMATION: polypeptide

<400> SEQUENCE: 43

Thr Phe Phe Tyr Gly Gly Cys Leu Gly Asn Lys Asn Tyr Val Arg
1               5                   10                  15

Glu Lys Tyr

<210> SEQ ID NO 44
<211> LENGTH: 19
<212> TYPE: PRT
<213> ORGANISM: Artificial sequence
<220> FEATURE:
<223> OTHER INFORMATION: polypeptide

<400> SEQUENCE: 44

Thr Phe Phe Tyr Gly Gly Cys Gly Gly Asn Gly Asn Asn Phe Leu Thr
1               5                   10                  15

Ala Lys Tyr

<210> SEQ ID NO 45
<211> LENGTH: 19
<212> TYPE: PRT
<213> ORGANISM: Artificial sequence
<220> FEATURE:
<223> OTHER INFORMATION: polypeptide

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial sequence
<220> FEATURE:
<223> OTHER INFORMATION: polypeptide

<400> SEQUENCE: 46

Thr Phe Phe Tyr Gly Gly Cys Arg Gly Asn Gly Asn Asn Phe Lys Ser
1               5                   10                  15

Ala Glu Tyr

<210> SEQ ID NO 47
<211> LENGTH: 19
<212> TYPE: PRT
<213> ORGANISM: Artificial sequence
<220> FEATURE:
<223> OTHER INFORMATION: polypeptide

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial sequence
<220> FEATURE:
<223> OTHER INFORMATION: polypeptide

<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial sequence
<220> FEATURE:
<223> OTHER INFORMATION: polypeptide

<400> SEQUENCE: 49

Thr Phe Phe Tyr Gly Gly Cys Arg Gly Lys Arg Asn Asn Phe Lys Thr
1               5                   10                  15

Glu Glu Asp

<210> SEQ ID NO 50
<211> LENGTH: 19
<212> TYPE: PRT
<213> ORGANISM: Artificial sequence
<220> FEATURE:
<223> OTHER INFORMATION: polypeptide

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial sequence
<220> FEATURE:
<223> OTHER INFORMATION: polypeptide

<400> SEQUENCE: 51

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19
<212> TYPE: PRT
<213> ORGANISM: Artificial sequence
<220> FEATURE:
<223> OTHER INFORMATION: polypeptide

<400> SEQUENCE: 52

Pro Phe Phe Tyr Gly Gly Cys Gly Asn Gly Asn Asn Phe Leu Arg
1               5                   10                  15

Glu Lys Tyr

<210> SEQ ID NO 53
<211> LENGTH: 19
<212> TYPE: PRT
<213> ORGANISM: Artificial sequence
<220> FEATURE:
<223> OTHER INFORMATION: polypeptide

<400> SEQUENCE: 53

Thr Phe Phe Tyr Gly Gly Cys Leu Gly Asn Gly Asn Asn Phe Val Arg
1               5                   10                  15

Glu Lys Tyr

<210> SEQ ID NO 54
<211> LENGTH: 19
<212> TYPE: PRT
<213> ORGANISM: Artificial sequence
<220> FEATURE:
<223> OTHER INFORMATION: polypeptide

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
<212> TYPE: PRT
<213> ORGANISM: Artificial sequence
<220> FEATURE:
<223> OTHER INFORMATION: polypeptide

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial sequence
<220> FEATURE:
<223> OTHER INFORMATION: polypeptide

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial sequence
<220> FEATURE:
<223> OTHER INFORMATION: polypeptide

```
<400> SEQUENCE: 57

Thr Phe Phe Tyr Gly Gly Cys Leu Gly Lys Gly Asn Asn Phe Val Ser
1               5                   10                  15

Ala Glu Tyr

<210> SEQ ID NO 58
<211> LENGTH: 19
<212> TYPE: PRT
<213> ORGANISM: Artificial sequence
<220> FEATURE:
<223> OTHER INFORMATION: polypeptide

<400> SEQUENCE: 58

Thr Phe Phe Tyr Gly Gly Cys Leu Gly Asn Arg Asn Asn Phe Asp Arg
1               5                   10                  15

Ala Glu Tyr

<210> SEQ ID NO 59
<211> LENGTH: 19
<212> TYPE: PRT
<213> ORGANISM: Artificial sequence
<220> FEATURE:
<223> OTHER INFORMATION: polypeptide

<400> SEQUENCE: 59

Thr Phe Phe Tyr Gly Gly Cys Leu Gly Asn Arg Asn Asn Phe Leu Arg
1               5                   10                  15

Glu Glu Tyr

<210> SEQ ID NO 60
<211> LENGTH: 19
<212> TYPE: PRT
<213> ORGANISM: Artificial sequence
<220> FEATURE:
<223> OTHER INFORMATION: polypeptide

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial sequence
<220> FEATURE:
<223> OTHER INFORMATION: polypeptide

<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial sequence
<220> FEATURE:
<223> OTHER INFORMATION: polypeptide
```

<400> SEQUENCE: 62

Pro Phe Phe Tyr Gly Gly Ser Gly Gly Asn Arg Asn Asn Tyr Leu Arg
1               5                   10                  15

Glu Glu Tyr

<210> SEQ ID NO 63
<211> LENGTH: 19
<212> TYPE: PRT
<213> ORGANISM: Artificial sequence
<220> FEATURE:
<223> OTHER INFORMATION: polypeptide

<400> SEQUENCE: 63

Met Arg Pro Asp Phe Cys Leu Glu Pro Pro Tyr Thr Gly Pro Cys Val
1               5                   10                  15

Ala Arg Ile

<210> SEQ ID NO 64
<211> LENGTH: 21
<212> TYPE: PRT
<213> ORGANISM: Artificial sequence
<220> FEATURE:
<223> OTHER INFORMATION: polypeptide

<400> SEQUENCE: 64

Ala Arg Ile Ile Arg Tyr Phe Tyr Asn Ala Lys Ala Gly Leu Cys Gln
1               5                   10                  15

Thr Phe Val Tyr Gly
            20

<210> SEQ ID NO 65
<211> LENGTH: 22
<212> TYPE: PRT
<213> ORGANISM: Artificial sequence
<220> FEATURE:
<223> OTHER INFORMATION: polypeptide

<400> SEQUENCE: 65

Tyr Gly Gly Cys Arg Ala Lys Arg Asn Asn Tyr Lys Ser Ala Glu Asp
1               5                   10                  15

Cys Met Arg Thr Cys Gly
            20

<210> SEQ ID NO 66
<211> LENGTH: 22
<212> TYPE: PRT
<213> ORGANISM: Artificial sequence
<220> FEATURE:
<223> OTHER INFORMATION: polypeptide

<400> SEQUENCE: 66

Pro Asp Phe Cys Leu Glu Pro Pro Tyr Thr Gly Pro Cys Val Ala Arg
1               5                   10                  15

Ile Ile Arg Tyr Phe Tyr
            20

<210> SEQ ID NO 67
<211> LENGTH: 19
<212> TYPE: PRT
<213> ORGANISM: Artificial sequence
<220> FEATURE:
<223> OTHER INFORMATION: polypeptide
<220> FEATURE:
<221> NAME/KEY: MISC_FEATURE
<223> OTHER INFORMATION: may be amidated

<400> SEQUENCE: 67

Thr Phe Phe Tyr Gly Gly Cys Arg Gly Lys Arg Asn Asn Phe Lys Thr
1               5                   10                  15

Glu Glu Tyr

<210> SEQ ID NO 68
<211> LENGTH: 19
<212> TYPE: PRT
<213> ORGANISM: Artificial sequence
<220> FEATURE:
<223> OTHER INFORMATION: polypeptide

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial sequence
<220> FEATURE:
<223> OTHER INFORMATION: polypeptide

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial sequence
<220> FEATURE:
<223> OTHER INFORMATION: polypeptide

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
<213> ORGANISM: Artificial sequence
<220> FEATURE:
<223> OTHER INFORMATION: polypeptide

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial sequence
<220> FEATURE:
<223> OTHER INFORMATION: polypeptide

```
<400> SEQUENCE: 72

Thr Phe Phe Tyr Gly Gly Cys Arg Gly Lys Arg Asn Asn Phe Lys Thr
1               5                   10                  15
Glu Glu Tyr Cys
            20

<210> SEQ ID NO 73
<211> LENGTH: 20
<212> TYPE: PRT
<213> ORGANISM: Artificial sequence
<220> FEATURE:
<223> OTHER INFORMATION: polypeptide

<400> SEQUENCE: 73

Cys Thr Phe Phe Tyr Gly Ser Cys Arg Gly Lys Arg Asn Asn Phe Lys
1               5                   10                  15
Thr Glu Glu Tyr
            20

<210> SEQ ID NO 74
<211> LENGTH: 20
<212> TYPE: PRT
<213> ORGANISM: Artificial sequence
<220> FEATURE:
<223> OTHER INFORMATION: polypeptide

<400> SEQUENCE: 74

Thr Phe Phe Tyr Gly Gly Ser Arg Gly Lys Arg Asn Asn Phe Lys Thr
1               5                   10                  15
Glu Glu Tyr Cys
            20

<210> SEQ ID NO 75
<211> LENGTH: 19
<212> TYPE: PRT
<213> ORGANISM: Artificial sequence
<220> FEATURE:
<223> OTHER INFORMATION: polypeptide

<400> SEQUENCE: 75

Pro Phe Phe Tyr Gly Gly Cys Arg Gly Lys Arg Asn Asn Phe Lys Thr
1               5                   10                  15
Glu Glu Tyr

<210> SEQ ID NO 76
<211> LENGTH: 19
<212> TYPE: PRT
<213> ORGANISM: Artificial sequence
<220> FEATURE:
<223> OTHER INFORMATION: polypeptide
<220> FEATURE:
<221> NAME/KEY: MISC_FEATURE
<223> OTHER INFORMATION: may be amidated

<400> SEQUENCE: 76

Thr Phe Phe Tyr Gly Gly Cys Arg Gly Lys Arg Asn Asn Phe Lys Thr
1               5                   10                  15
Lys Glu Tyr

<210> SEQ ID NO 77
<211> LENGTH: 19
<212> TYPE: PRT
<213> ORGANISM: Artificial sequence
<220> FEATURE:
```

<223> OTHER INFORMATION: polypeptide

<400> SEQUENCE: 77

Thr Phe Phe Tyr Gly Gly Lys Arg Gly Lys Arg Asn Asn Phe Lys Thr
1               5                   10                  15

Glu Glu Tyr

<210> SEQ ID NO 78
<211> LENGTH: 19
<212> TYPE: PRT
<213> ORGANISM: Artificial sequence
<220> FEATURE:
<223> OTHER INFORMATION: polypeptide

<400> SEQUENCE: 78

Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial sequence
<220> FEATURE:
<223> OTHER INFORMATION: polypeptide

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial sequence
<220> FEATURE:
<223> OTHER INFORMATION: polypeptide

<400> SEQUENCE: 80

Thr Phe Phe Tyr Gly Gly Lys Arg Gly Lys Arg Asn Asn Phe Lys Thr
1               5                   10                  15

Ala Gly Tyr

<210> SEQ ID NO 81
<211> LENGTH: 19
<212> TYPE: PRT
<213> ORGANISM: Artificial sequence
<220> FEATURE:
<223> OTHER INFORMATION: polypeptide

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial sequence
<220> FEATURE:
<223> OTHER INFORMATION: polypeptide

```
<400> SEQUENCE: 82

Thr Phe Phe Tyr Gly Gly Lys Arg Gly Lys Arg Asn Asn Phe Lys Arg
1               5                   10                  15

Ala Lys Tyr

<210> SEQ ID NO 83
<211> LENGTH: 19
<212> TYPE: PRT
<213> ORGANISM: Artificial sequence
<220> FEATURE:
<223> OTHER INFORMATION: polypeptide

<400> SEQUENCE: 83

Thr Phe Phe Tyr Gly Gly Cys Leu Gly Asn Arg Asn Asn Phe Lys Thr
1               5                   10                  15

Glu Glu Tyr

<210> SEQ ID NO 84
<211> LENGTH: 19
<212> TYPE: PRT
<213> ORGANISM: Artificial sequence
<220> FEATURE:
<223> OTHER INFORMATION: polypeptide

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial sequence
<220> FEATURE:
<223> OTHER INFORMATION: polypeptide

<400> SEQUENCE: 85

Thr Phe Phe Tyr Gly Gly Arg Cys Gly Lys Arg Asn Asn Phe Lys Thr
1               5                   10                  15

Glu Glu Tyr

<210> SEQ ID NO 86
<211> LENGTH: 19
<212> TYPE: PRT
<213> ORGANISM: Artificial sequence
<220> FEATURE:
<223> OTHER INFORMATION: polypeptide

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
<213> ORGANISM: Artificial sequence
<220> FEATURE:
<223> OTHER INFORMATION: polypeptide
```

<400> SEQUENCE: 87

Thr Phe Gln Tyr Gly Gly Cys Arg Gly Lys Arg Asn Asn Phe Lys Thr
1               5                   10                  15

Glu Glu Tyr

<210> SEQ ID NO 88
<211> LENGTH: 19
<212> TYPE: PRT
<213> ORGANISM: Artificial sequence
<220> FEATURE:
<223> OTHER INFORMATION: polypeptide

<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial sequence
<220> FEATURE:
<223> OTHER INFORMATION: polypeptide

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial sequence
<220> FEATURE:
<223> OTHER INFORMATION: polypeptide

<400> SEQUENCE: 90

Arg Phe Lys Tyr Gly Gly Cys Leu Gly Asn Lys Asn Asn Phe Leu Arg
1               5                   10                  15

Leu Lys Tyr

<210> SEQ ID NO 91
<211> LENGTH: 19
<212> TYPE: PRT
<213> ORGANISM: Artificial sequence
<220> FEATURE:
<223> OTHER INFORMATION: polypeptide
<220> FEATURE:
<221> NAME/KEY: MISC_FEATURE
<223> OTHER INFORMATION: may be amidated

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial sequence
<220> FEATURE:
<223> OTHER INFORMATION: polypeptide

```
<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20

<210> SEQ ID NO 93
<211> LENGTH: 15
<212> TYPE: PRT
<213> ORGANISM: Artificial sequence
<220> FEATURE:
<223> OTHER INFORMATION: polypeptide

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial sequence
<220> FEATURE:
<223> OTHER INFORMATION: polypeptide

<400> SEQUENCE: 94

Arg Gly Gly Arg Leu Ser Tyr Ser Arg Phe Ser Thr Ser Thr Gly
1               5                   10                  15

Arg

<210> SEQ ID NO 95
<211> LENGTH: 10
<212> TYPE: PRT
<213> ORGANISM: Artificial sequence
<220> FEATURE:
<223> OTHER INFORMATION: polypeptide

<400> SEQUENCE: 95

Arg Arg Leu Ser Tyr Ser Arg Arg Arg Phe
1               5                   10

<210> SEQ ID NO 96
<211> LENGTH: 16
<212> TYPE: PRT
<213> ORGANISM: Artificial sequence
<220> FEATURE:
<223> OTHER INFORMATION: polypeptide

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial sequence
<220> FEATURE:
<223> OTHER INFORMATION: polypeptide

<400> SEQUENCE: 97

Thr Phe Phe Tyr Gly Gly Ser Arg Gly Lys Arg Asn Asn Phe Lys Thr
1               5                   10                  15

Glu Glu Tyr
```

<210> SEQ ID NO 98
<211> LENGTH: 59
<212> TYPE: PRT
<213> ORGANISM: Artificial sequence
<220> FEATURE:
<223> OTHER INFORMATION: polypeptide

<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
    50                  55

<210> SEQ ID NO 99
<211> LENGTH: 19
<212> TYPE: PRT
<213> ORGANISM: Artificial sequence
<220> FEATURE:
<223> OTHER INFORMATION: polypeptide

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial sequence
<220> FEATURE:
<223> OTHER INFORMATION: polypeptide

<400> SEQUENCE: 100

Arg Phe Lys Tyr Gly Gly Cys Leu Gly Asn Lys Asn Asn Tyr Leu Arg
1               5                   10                  15

Leu Lys Tyr

<210> SEQ ID NO 101
<211> LENGTH: 19
<212> TYPE: PRT
<213> ORGANISM: Artificial sequence
<220> FEATURE:
<223> OTHER INFORMATION: polypeptide

<400> SEQUENCE: 101

Thr Phe Phe Tyr Gly Gly Cys Arg Ala Lys Arg Asn Asn Phe Lys Arg
1               5                   10                  15

Ala Lys Tyr

<210> SEQ ID NO 102
<211> LENGTH: 35
<212> TYPE: PRT
<213> ORGANISM: Artificial sequence
<220> FEATURE:
<223> OTHER INFORMATION: polypeptide -continued

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
            20                  25                  30

Gly Gly Ala
        35

<210> SEQ ID NO 103
<211> LENGTH: 24
<212> TYPE: PRT
<213> ORGANISM: Artificial sequence
<220> FEATURE:
<223> OTHER INFORMATION: polypeptide
<300> PUBLICATION INFORMATION:
<310> PATENT DOCUMENT NUMBER: US 5,780,265
<311> PATENT FILING DATE: 1995-07-05
<312> PUBLICATION DATE: 1998-07-14

<400> SEQUENCE: 103

Tyr Gly Gly Cys Arg Ala Lys Arg Asn Asn Phe Lys Ser Ala Glu Asp
1               5                   10                  15

Cys Met Arg Thr Cys Gly Gly Ala
            20

<210> SEQ ID NO 104
<211> LENGTH: 22
<212> TYPE: PRT
<213> ORGANISM: Artificial sequence
<220> FEATURE:
<223> OTHER INFORMATION: polypeptide

<400> SEQUENCE: 104

Gly Leu Cys Gln Thr Phe Val Tyr Gly Gly Cys Arg Ala Lys Arg Asn
1               5                   10                  15

Asn Phe Lys Ser Ala Glu
            20

<210> SEQ ID NO 105
<211> LENGTH: 20
<212> TYPE: PRT
<213> ORGANISM: Artificial sequence
<220> FEATURE:
<223> OTHER INFORMATION: polypeptide

<400> SEQUENCE: 105

Leu Cys Gln Thr Phe Val Tyr Gly Gly Cys Glu Ala Lys Arg Asn Asn
1               5                   10                  15

Phe Lys Ser Ala
        20

<210> SEQ ID NO 106
<211> LENGTH: 180
<212> TYPE: DNA
<213> ORGANISM: Artificial sequence
<220> FEATURE:
<223> OTHER INFORMATION: synthetic construct

<400> SEQUENCE: 106
atgagaccag atttctgcct cgagccgccg tacactgggc cctgcaaagc tcgtatcatc      60
cgttacttct acaatgcaaa ggcaggcctg tgtcagacct tcgtatacgg cggctgcaga     120
gctaagcgta acaacttcaa atccgcggaa gactgcatgc gtacttgcgg tggtgcttag     180

```
<210> SEQ ID NO 107
<211> LENGTH: 19
<212> TYPE: PRT
<213> ORGANISM: Artificial sequence
<220> FEATURE:
<223> OTHER INFORMATION: polypeptide
<220> FEATURE:
<221> NAME/KEY: MISC_FEATURE
<223> OTHER INFORMATION: may be acetylated

<400> SEQUENCE: 107

Thr Phe Phe Tyr Gly Gly Ser Arg Gly Lys Arg Asn Asn Phe Lys Thr
1               5                   10                  15

Glu Glu Tyr

<210> SEQ ID NO 108
<211> LENGTH: 19
<212> TYPE: PRT
<213> ORGANISM: Artificial sequence
<220> FEATURE:
<223> OTHER INFORMATION: polypeptide

<400> SEQUENCE: 108

Arg Phe Phe Tyr Gly Gly Ser Arg Gly Lys Arg Asn Asn Phe Lys Thr
1               5                   10                  15

Glu Glu Tyr

<210> SEQ ID NO 109
<211> LENGTH: 19
<212> TYPE: PRT
<213> ORGANISM: Artificial sequence
<220> FEATURE:
<223> OTHER INFORMATION: polypeptide
<220> FEATURE:
<221> NAME/KEY: MISC_FEATURE
<223> OTHER INFORMATION: may be acetylated

<400> SEQUENCE: 109

Arg Phe Phe Tyr Gly Gly Ser Arg Gly Lys Arg Asn Asn Phe Lys Thr
1               5                   10                  15

Glu Glu Tyr

<210> SEQ ID NO 110
<211> LENGTH: 19
<212> TYPE: PRT
<213> ORGANISM: Artificial sequence
<220> FEATURE:
<223> OTHER INFORMATION: polypeptide
<220> FEATURE:
<221> NAME/KEY: MISC_FEATURE
<223> OTHER INFORMATION: may be acetylated

<400> SEQUENCE: 110

Arg Phe Phe Tyr Gly Gly Ser Arg Gly Lys Arg Asn Asn Phe Arg Thr
1               5                   10                  15

Glu Glu Tyr

<210> SEQ ID NO 111
<211> LENGTH: 19
<212> TYPE: PRT
<213> ORGANISM: Artificial sequence
<220> FEATURE:
<223> OTHER INFORMATION: polypeptide
```

```
<400> SEQUENCE: 111

Thr Phe Phe Tyr Gly Gly Ser Arg Gly Lys Arg Asn Asn Phe Arg Thr
1               5                   10                  15

Glu Glu Tyr

<210> SEQ ID NO 112
<211> LENGTH: 19
<212> TYPE: PRT
<213> ORGANISM: Artificial sequence
<220> FEATURE:
<223> OTHER INFORMATION: polypeptide

<400> SEQUENCE: 112

Thr Phe Phe Tyr Gly Gly Ser Arg Gly Arg Arg Asn Asn Phe Arg Thr
1               5                   10                  15

Glu Glu Tyr

<210> SEQ ID NO 113
<211> LENGTH: 20
<212> TYPE: PRT
<213> ORGANISM: Artificial sequence
<220> FEATURE:
<223> OTHER INFORMATION: polypeptide

<400> SEQUENCE: 113

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 114
<211> LENGTH: 20
<212> TYPE: PRT
<213> ORGANISM: Artificial sequence
<220> FEATURE:
<223> OTHER INFORMATION: polypeptide

<400> SEQUENCE: 114

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 115
<211> LENGTH: 20
<212> TYPE: PRT
<213> ORGANISM: Artificial sequence
<220> FEATURE:
<223> OTHER INFORMATION: polypeptide

<400> SEQUENCE: 115

Cys Thr Phe Phe Tyr Gly Gly Ser Arg Gly Arg Arg Asn Asn Phe Arg
1               5                   10                  15

Thr Glu Glu Tyr
            20

<210> SEQ ID NO 116
<211> LENGTH: 20
<212> TYPE: PRT
<213> ORGANISM: Artificial sequence
<220> FEATURE:
<223> OTHER INFORMATION: polypeptide
```

```
<400> SEQUENCE: 116

Thr Phe Phe Tyr Gly Gly Ser Arg Gly Arg Arg Asn Asn Phe Arg Thr
1               5                   10                  15

Glu Glu Tyr Cys
            20
```

ETOPOSIDE AND DOXORUBICIN CONJUGATES FOR DRUG DELIVERY

CROSS-REFERENCE TO RELATED APPLICATIONS

This application is the U.S. national stage filing under 35 U.S.C. §371 of international application PCT/CA2009/001481, filed Oct. 15, 2009, which claims benefit of the filing date of U.S. Provisional Application No. 61/171,010, filed Apr. 20, 2009, and U.S. Provisional Application No. 61/105,654, filed Oct. 15, 2008, each of which is incorporated by reference.

FIELD OF THE INVENTION

The invention relates to improvements in the field of drug delivery. More particularly, the invention relates to polypeptides having a hydrolyzable covalent bond to a therapeutic agent such as a podophyllotoxin derivative (e.g., etoposide or an etoposide derivative such as etoposide 4'-dimethylglycine) or to doxorubicin or a doxorubicin derivative. These polypeptide conjugates can be used as vectors to transport the therapeutic agent across the blood brain barrier (BBB) or into particular cell types such as ovary, liver, lung, or kidney. These conjugates can show improved physicochemical (e.g., increased solubility) and pharmaceutical properties (e.g., enhanced targeting that allows for subtherapeutic doses or reduced toxicity that allows for supertherapeutic doses) relative to the unconjugated therapeutic agent. The invention also relates to pharmaceutical compositions that include the compounds of the invention and to uses thereof in methods of treatment.

BACKGROUND OF THE INVENTION

Many therapeutic agents for such diseases have undesirable side effects (e.g., chemotherapeutic agents) or, for reasons such as in vivo stability, transport, or other pharmacokinetic properties, are difficult to provide at a sufficiently high concentration in the target tissue or for a sufficiently long duration to allow maximal therapeutic effect in the target tissue. Accordingly, there is a need for methods and compositions that increase concentrations of therapeutic and diagnostic agents in target organs or tissues such as the brain, ovary, liver, or lung.

SUMMARY OF THE INVENTION

We have developed peptide-therapeutic conjugates, and pharmaceutically acceptable salts thereof, where etoposide is covalently attached to the Angiopep-2 polypeptide (SEQ ID NO:97) at the 2" hydroxyl via a hydrolyzable glutaric acid linker (e.g., Compound (1) shown in Scheme 1). A related peptide-therapeutic conjugate has also been prepared in which etoposide 4'-dimethylglycine is used instead of etoposide, and improved properties (e.g., solubility) are observed.

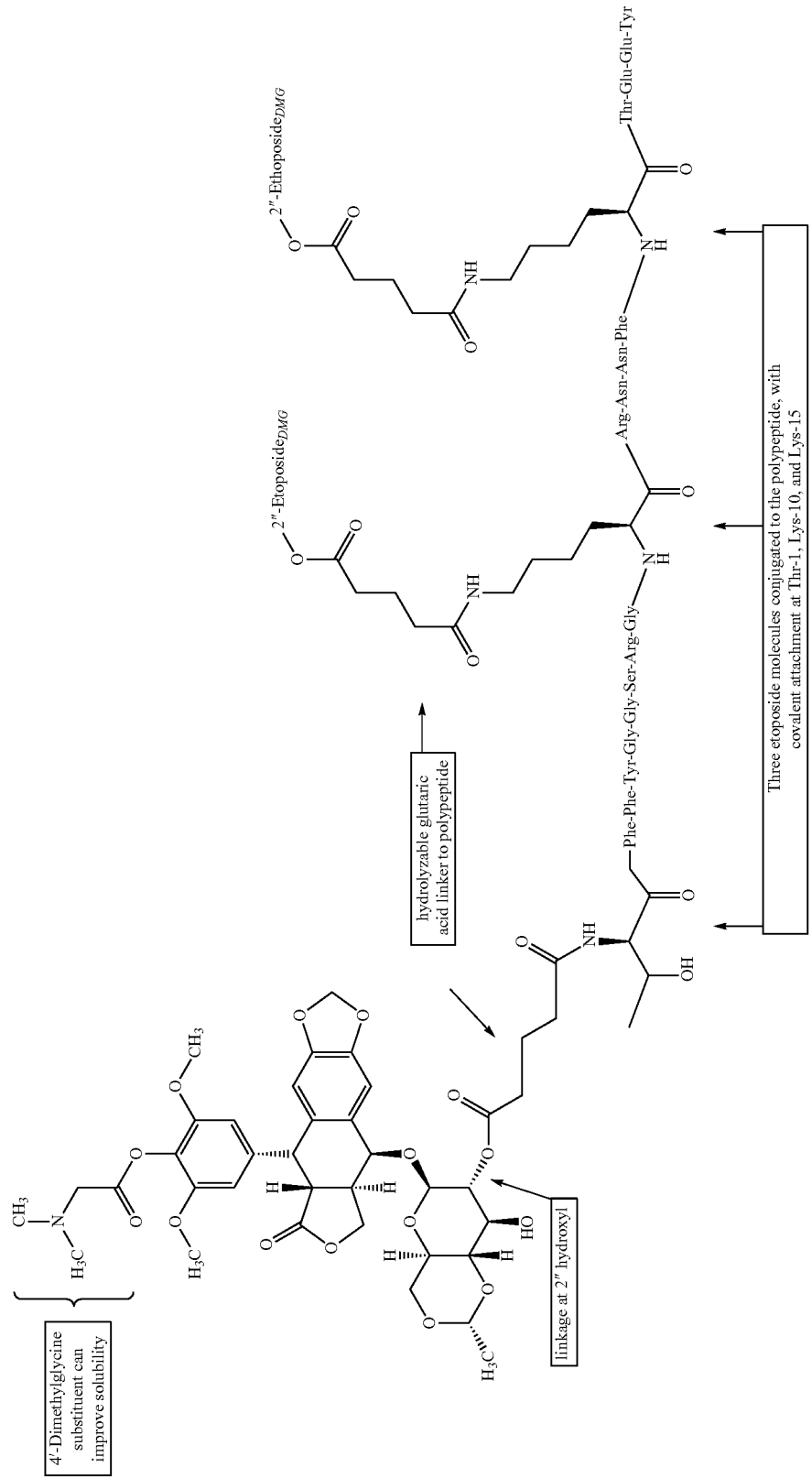
Scheme 1

Doxorubicin has also been covalently attached at the 14-hydroxyl to the Angiopep-2 polypeptide using a succinic acid linker (e.g., the trihydrochloride salt of Compound (2) shown in Scheme 2). Covalent attachment of the doxorubicin hydrochloride salt can also afford improved properties (e.g., solubility).

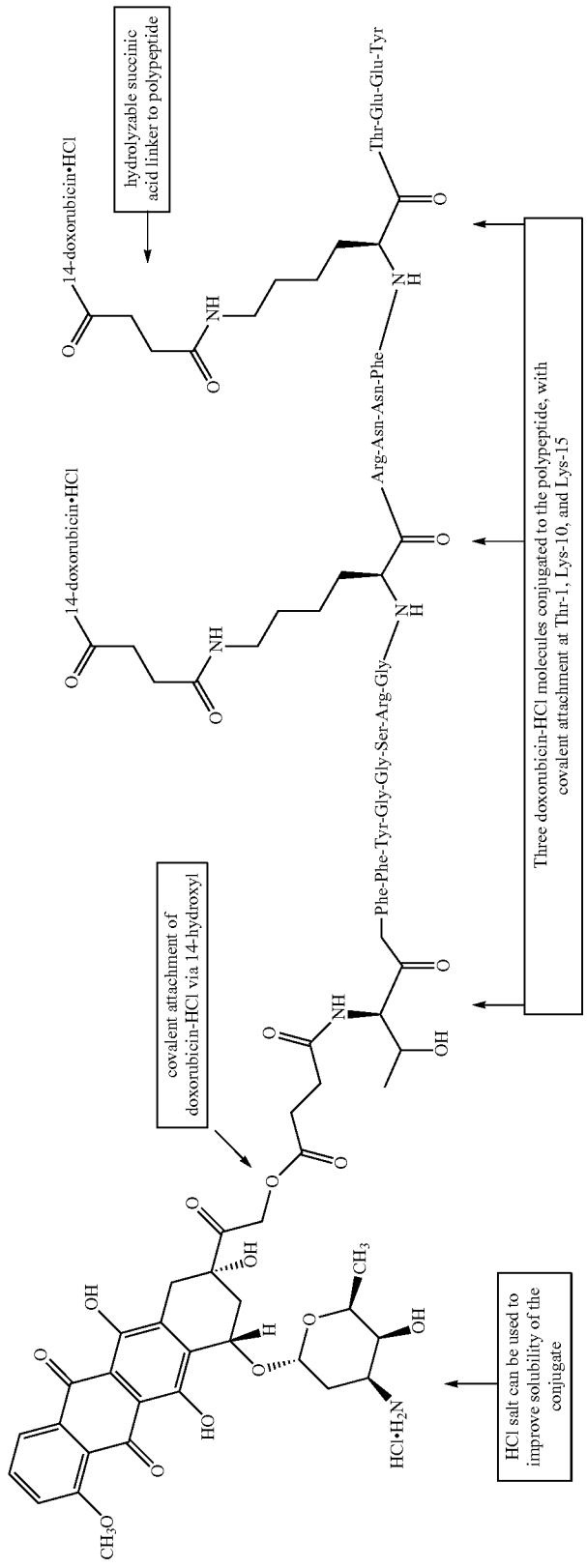
Scheme 2

These conjugates can show improved properties relative to the corresponding unconjugated therapeutic agent such as improved physicochemical (e.g., increased solubility) and pharmaceutical (e.g., enhanced targeting that allows for sub-therapeutic doses or reduced toxicity that allows for super-therapeutic doses) properties. The solubility of the etoposide$_{DMG}$ and the doxorubicin hydrochloride conjugates can also be useful in adjusting dosing regimens. The invention therefore features these compounds, as well as related compounds. Methods of making and using these compounds are also provided.

Accordingly, in one aspect, the invention features a compound, or a pharmaceutically acceptable salt thereof, that includes an amino acid sequence substantially identical to an amino acid sequence selected from the group consisting of SEQ ID NOS:1-105 and 107-116, or a functional derivative thereof, where the amino acid sequence includes a covalent bond from an amino acid of the amino acid sequence to a podophyllotoxin derivative. In some embodiments, the podophyllotoxin derivative is a compound having a structure according to Formula (I):

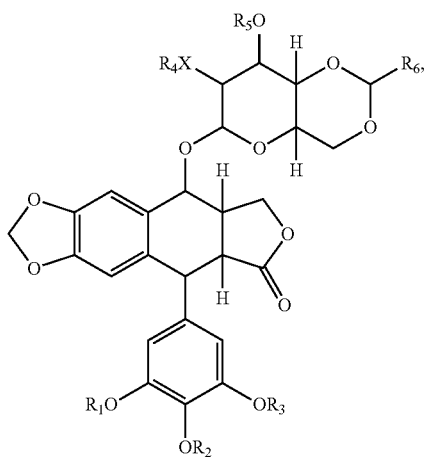

or a stereoisomer or pharmaceutically acceptable salt thereof, where each $R_1$, $R_2$, and $R_3$ is selected, independently, from H, optionally substituted $C_{1-6}$ alkyl, $C(O)R_8$, $P(O)(OR_9)(OR_{10})$, $S(O)_2(OR_9)$, or a hydrolyzable linker Y that comprises a covalent bond to an amino acid of the polypeptide;

X is O or $NR_7$;

each $R_4$, $R_5$, and $R_7$ is selected, independently, from H, optionally substituted $C_{1-6}$ alkyl, $C(O)R_8$, or a hydrolyzable linker Y that comprises a covalent bond to an amino acid of the polypeptide;

$R_6$ is H, optionally substituted $C_{1-6}$ alkyl, optionally substituted aryl, optionally substituted heteroaryl, $R_8$ is selected from optionally substituted $C_{1-6}$ alkyl or optionally substituted aryl;

each $R_9$ and $R_{10}$ is selected, independently, from H, optionally substituted $C_{1-6}$ alkyl, or optionally substituted aryl; and n is 1, 2, 3, 4, 5, 6, 7, or 8;

where one of $R_1$, $R_2$, $R_3$, $R_4$, $R_5$, and $R_7$ is Y and no more than one of $R_1$, $R_2$, $R_3$, $R_4$, $R_5$, and $R_7$ is Y.

In some embodiments, Y is —C(O)(CH$_2$)—C(O)— and n is 2, 3, or 4. In certain embodiments, n is 3.

In some embodiments, the pharmaceutically acceptable salt of the compound is the mono-, di-, or tri-acid addition salt (e.g., the mono-, di-, or trihydrochloride salt).

In some embodiments, each compound of Formula (I) is selected, independently, from:

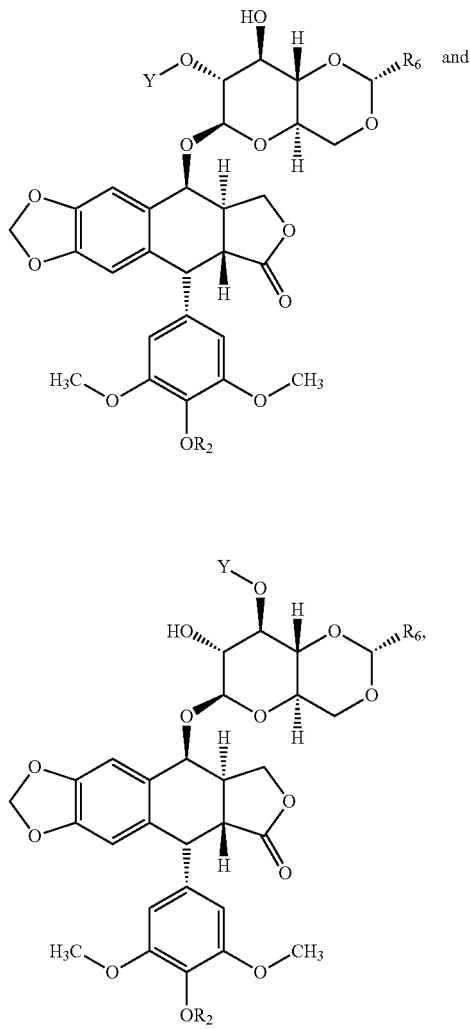

where each $R_2$ is, independently, H, P(O)(OH)$_2$, or C(O)CH$_2$N(CH$_3$)$_2$; each $R_6$ is, independently, CH$_3$ or 2-thiophene; each Y is selected from —C(O)(CH$_2$)—C(O)—; —[C(O){OCH$_2$CH$_2$}$_n$OC(O)]—; —S(O)$_2$(CH$_2$)$_n$S(O)$_2$—; —[S(O)$_2${OCH$_2$CH$_2$}$_n$OS(O)$_2$]—; —[{P(O)(OR$_9$)}(CH$_2$)$_n${P(O)(OR$_9$)}]—; and —[{P(O)(OR$_9$)}(OCH$_2$CH$_2$)$_n$—O{P(O)(OR$_9$)}]—; each n is, independently, 1, 2, 3, 4, 5, or 6; and where each Y is covalently bound to an amino acid. In some embodiments, each Y is —C(O)(CH$_2$)$_n$C(O)— or —[C(O){OCH$_2$CH$_2$}$_n$OC(O)]— and n is 2, 3, or 4. In some embodiments, each $R_2$ is C(O)CH$_2$N(CH$_3$)$_2$. In some embodiments, each compound of Formula (I) is:

```
     polypeptide—N—Y                    R6  or
                    O
                   H polypeptide—N—Y
                    O                   R6.
```

In some embodiments, the compound of the invention has the following structure

```
           TFFYGGSRGKRNNFKTEEY
           |         |   |
       Formula (I)   |  Formula (I),
              Formula (I)
``` where each (—(Formula (I)) group represents an optional covalent bond between the indicated amino acid and a compound of Formula (I), and where there is at least one covalent bond between an amino acid of the polypeptide and said compound of Formula (I). In some embodiments, two compounds of Formula (I) are attached to the amino acid sequence. In other embodiments, the threonine at position 1 and the lysines at positions 10 and 15 of the polypeptide each include a covalent bond to a compound having a structure according to Formula (I).

In some embodiments, $R_2$ is H or —C(O)CH$_2$N(CH$_3$)$_2$ (i.e., C-linked N,N-dimethylglycine). In other embodiments, each $R_2$ is H. In still other embodiments, each $R_2$ is —C(O)CH$_2$N(CH$_3$)$_2$.

In some embodiments, the optionally substituted $C_{1-6}$ alkyl is selected, independently, from methyl, ethyl, n-propyl, iso-propyl, n-butyl, iso-butyl, sec-butyl, sec-pentyl, iso-pentyl, tert-butyl, n-pentyl, neopentyl, n-hexyl, or sec-hexyl. In some embodiments, the $C_{1-6}$ alkyl is substituted with at least one optionally substituted amino group (e.g., NH$_2$ or N(CH$_3$)$_2$) at any carbon.

In some embodiments, the optionally substituted $C_{3-10}$ cycloalkyl is selected, independently, from cyclopropyl, cyclobutyl, cyclopentyl, cyclohexyl, and cycloheptyl.

In some embodiments, the optionally substituted aryl group is selected, independently, from phenyl, naphthyl, tetrahydronaphthyl, indanyl, or indenyl.

In some embodiments, the optionally substituted heterocyclyl group is selected, independently, from azacyclopropanyl, azacyclobutanyl, 1,3-diazatidinyl, pyrrolidinyl, piperidinyl, piperazinyl, thiranyl, thietanyl, tetrahydrothiophenyl, dithiolanyl, tetrahydrothiopyranyl, oxiranyl, oxetanyl, tetrahydrofuranyl, tetrahydropyranyl, dioxanyl, oxathiolanyl, morpholinyl, thiomorpholinyl, thioxanyl, and quinuclidinyl.

In some embodiments, the optionally substituted heterocyclyl group is selected from pyrrolyl, pyrazolyl, imadazolyl, pyridinyl, pyrimidinyl, pyrazinyl, pyridazinyl, triazinyl, tetrazinyl, pryyrolizinyl, indolyl, quinolinyl, isoquinolynyl, benzimidazolyl, indazolyl, quinolizinyl, cinnolinyl, quinazolinyl, phthalazinyl, napthyridinyl, quinoxalinyl, thiophenyl, thiepinyl, furanyl, benzofuranyl, thiazolyl, isothiazolyl, thiadiazolyl, oxazolyl, isoxazolyl, and oxadiazolyl.

In some embodiments, a substituted alkyl, cycloalkyl, aryl, heterocyclyl, or heteroaryl is substituted with 1, 2, 3, 4, 5, or 6 substituents selected from: $C_{1-6}$ alkyl; halogen; azido(—N$_3$), nitro (—NO$_2$), cyano (—CN), acyloxy, acyl (—C(O)R), (—OC(O)R), alkoxy (—OR), amido (—NRC(O)R' or —C(O)NRR'), amino (—NRR'), aryl, carboxylic acid (—CO$_2$H), carboxylic ester (—CO$_2$R), carbamoyl (—OC(O)NRR' or —NRC(O)OR'), cycloalkyl, heterocyclyl, hydroxy (—OH), isocyano (—NC), phosphate (—P(O)(OR)(OR')), sulfonate (—SO$_2$OR), or sulfonyl (—SO$_2$R), where each R or R' is selected, independently, from H, $C_{1-6}$ alkyl, cycloalkyl, heterocyclyl, aryl, or heteroaryl, as defined herein. In some embodiments, these substituents are not further substituted. In other embodiments, the substituents may themselves be further substituted with 1, 2, 3, 4, 5, or 6 substituent groups.

In some embodiments, $R_4$ is Y. In other embodiments, $R_5$ is Y.

In other embodiments, the amino acid sequence is covalently bonded to additional podophyllotoxin derivatives through a second, third, fourth, or fifth amino acid of said amino acid sequence. In some embodiments, the podophyllotoxin derivative is a compound of Formula (I).

In certain embodiments, the compound of Formula I has the structure:

where Y is —C(O)(CH$_2$)$_n$C(O)— or —[C(O){OCH$_2$CH$_2$}$_n$OC(O)]— and n is 2, 3, or 4.

In other embodiments, the compound of Formula (I) has the following structure:

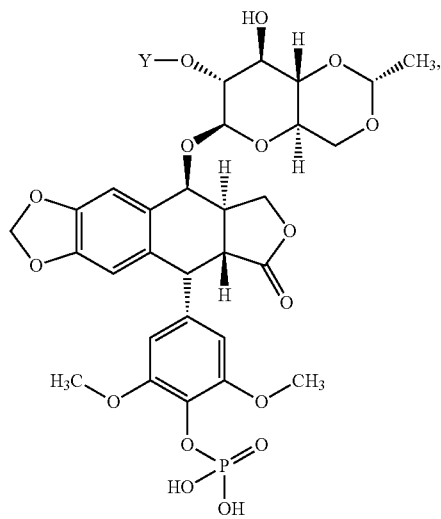

where Y is —C(O)(CH$_2$)$_n$C(O)— or —[C(O){OCH$_2$CH$_2$}$_n$OC(O)]— and n is 2, 3, or 4.

In still other embodiments, the compound of Formula (I) has the following structure:

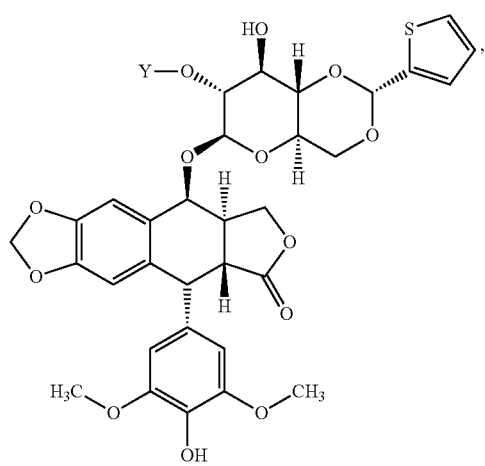

where Y is —C(O)(CH$_2$)$_n$C(O)— or —[C(O){OCH$_2$CH$_2$}$_n$OC(O)]— and n is 2, 3, or 4.

In other embodiments, each compound of Formula (I) is selected, independently, from:

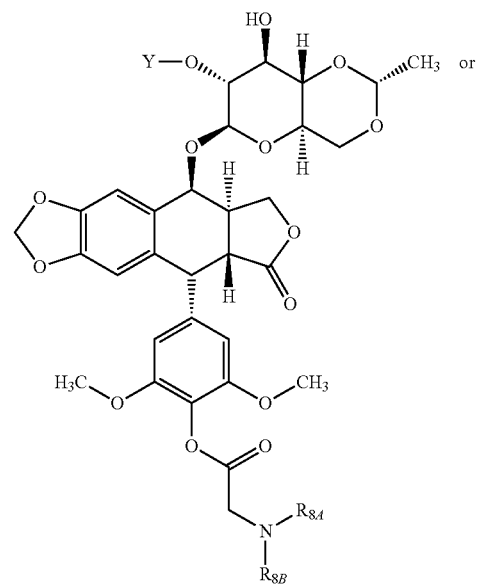

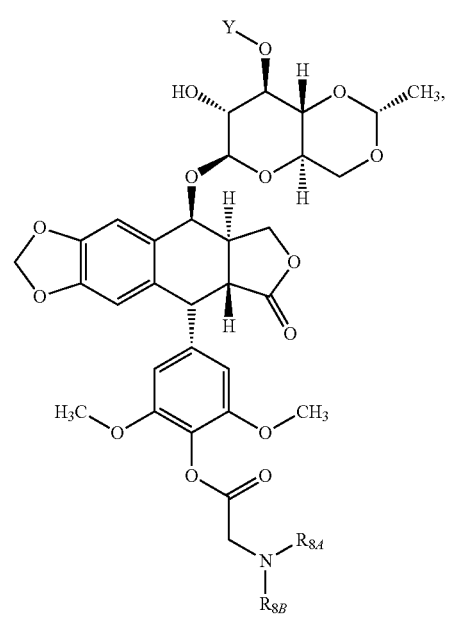

where each $R_{8A}$ and $R_{8B}$ is, independently, H or optionally substituted C$_{1-6}$ alkyl, or $R_{8A}$ and $R_{8B}$ combine to form an optionally substituted 3-7 membered ring. In some embodiments, each $R_{8A}$ and $R_{8B}$ is optionally substituted C$_{1-6}$ alkyl. In other embodiments, each compound of Formula (I) has the following structure:

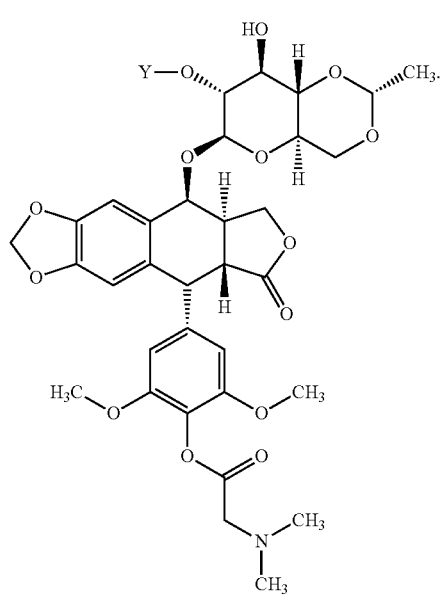
In further embodiments, the compound the following structure:
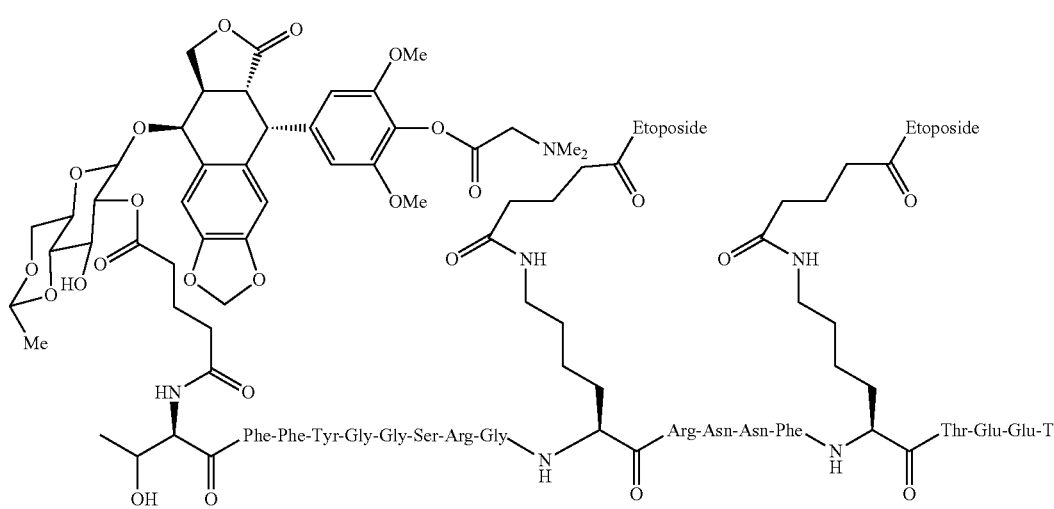
In particular embodiments, the compound has the structure:
(1)

or a pharmaceutically acceptable salt thereof (e.g., the trihydrochloride salt), where in Compound (1), etoposide refers to etoposide 4'-dimethylglycine.

In certain embodiments, each amino acid that is covalently bonded to the hydrolyzable linker Y is attached via an amino-, a guanidino-, a hydroxyl-, a phenol-, or a thiol functional group of said amino acid. In some embodiments, the amino acid that is covalently bonded to the hydrolyzable linker Y is lysine, tyrosine, serine, threonine, or arginine.

In a second aspect, the invention features a compound, or a pharmaceutically acceptable salt thereof, that includes an amino acid sequence substantially identical to an amino acid sequence selected from the group consisting of SEQ ID NOS: 1-105 and 107-116, or a functional derivative thereof, wherein said amino acid sequence includes a covalent bond from an amino acid of said amino acid sequence to a doxorubicin derivative, and wherein said doxorubicin derivative is a compound having a structure according to Formula (II):

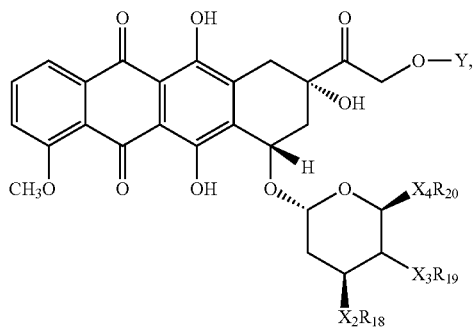

where $X_2R_{18}$ is H or $NH_2$; $X_3R_{19}$ is H or OH; $X_4R_{20}$ is H or optionally substituted $C_{1-3}$ alkyl; and Y is a hydrolyzable linker as described herein. In further embodiments, the compound of Formula (II) has the following structure:

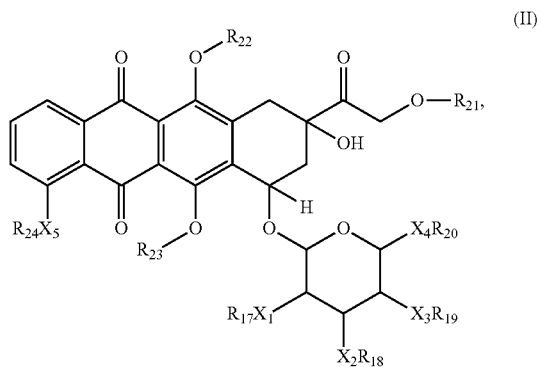

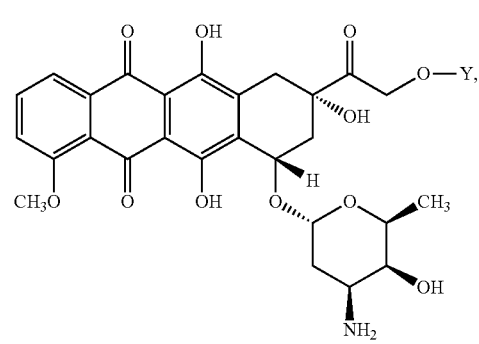

or a pharmaceutically acceptable salt thereof.

In further embodiments, the compound of Formula (II) has the following structure:

or a stereoisomer or a pharmaceutically acceptable salt thereof, wherein each $X_1$, $X_2$, $X_3$, $X_4$, and $X_5$ is selected, independently, from a covalent bond, O, or $NR_{25}$;

each $R_{17}$, $R_{18}$, $R_{19}$, $R_{20}$, $R_{21}$, $R_{22}$, $R_{23}$, $R_{24}$, and $R_{25}$ is selected, independently, from H, optionally substituted $C_{1-6}$ alkyl, optionally substituted $C_{2-6}$ alkenyl, optionally substituted $C_{2-6}$ alkynyl, optionally substituted cycloalkyl, optionally substituted heterocyclyl, or is a hydrolyzable linker Y; and wherein one and only one of $R_{17}$, $R_{18}$, $R_{19}$, $R_{20}$, $R_{20}$, $R_{21}$, $R_{22}$, $R_{23}$, $R_{24}$, and $R_{25}$ is Y.

In some embodiments, the pharmaceutically acceptable salt of the compound is the mono-, di-, or tri-acid addition salt (e.g., the mono-, di-, or trihydrochloride salt).

In certain embodiments, the compound of Formula (II) has the following structure:

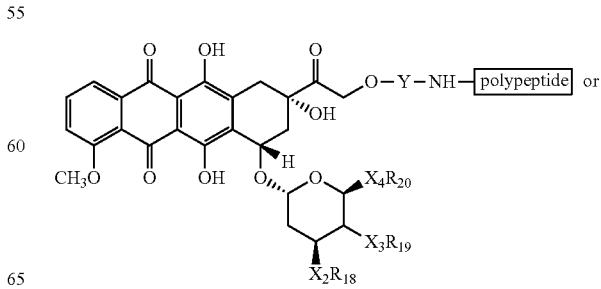

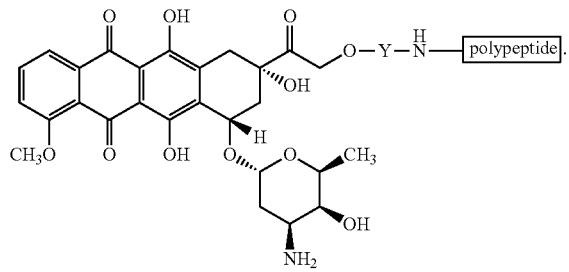

In certain embodiments, the compound has the following structure:

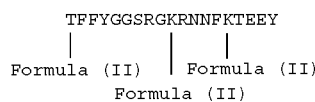

wherein each (—(Formula (II)) represents an optional covalent bond between the indicated amino acid and a compound of Formula (II), and wherein there is at least one covalent bond between an amino acid of the polypeptide and said compound of Formula (II). In some embodiments, the threonine at position 1 and the lysines at positions 10 and 15 of the polypeptide each comprise a covalent bond to a compound having a structure according to Formula (II).

In some embodiments, Y is —C(O)(CH$_2$)$_n$C(O)—, and n is 2, 3, or 4. In certain embodiments, n is 2. In other embodiments, the amino acid sequence is covalently bonded to a compound having a structure according to Formula (II) through a second, third, fourth, or fifth amino acid of the amino acid sequence. In another embodiment, each amino acid covalently bonded to said hydrolyzable linker Y is attached via an amino-, a guanidino-, a hydroxyl-, a phenol-, or a thiol functional group of said amino acid. In certain embodiments, the amino acid is lysine or threonine.

In some embodiments, the compound of Formula (II) has the following structure:

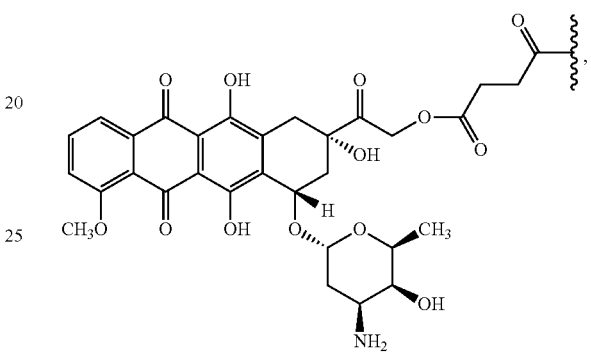

or a pharmaceutically acceptable salt thereof.

In particular embodiments, the compound has the structure:

(2)

or a pharmaceutically acceptable salt thereof (e.g., the trihydrochloride salt).

In another aspect, the invention features the following compound,

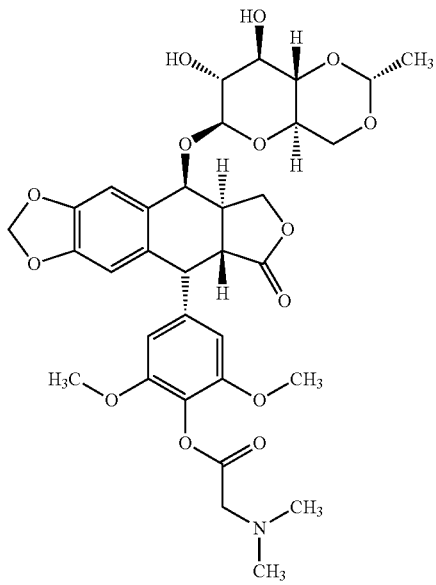

("etoposide 4'-dimethylglycine" or "etoposide$_{DMG}$"), or any stereoisomer, or any pharmaceutically acceptable salt or solvent thereof.

In any of the above aspects, the amino acid sequence may be substantially identical to any of the sequences set forth in Table 1, or a fragment thereof or a pharmaceutically acceptable salt thereof. In certain embodiments, the amino acid sequence has a sequence of Angiopep-1 (SEQ ID NO:67), Angiopep-2 (SEQ ID NO:97), Angiopep-3 (SEQ ID NO:107), Angiopep-4a (SEQ ID NO:108), Angiopep-4b (SEQ ID NO:109), Angiopep-5 (SEQ ID NO:110), Angiopep-6 (SEQ ID NO:111), or Angiopep-7 (SEQ ID NO:112)). The amino acid sequence or the compounds of the invention may be efficiently transported into a particular cell type (e.g., any one, two, three, four, or five of liver, ovary, lung, kidney, spleen, and muscle) or may cross the mammalian BBB efficiently (e.g., Angiopep-1, -2, -3, -4a, -4b, -5, and -6). In some embodiments, the cells are ovary cells. In another embodiment, the conjugate is able to enter a particular cell type (e.g., any one, two, three, four, or five of liver, ovary, lung, kidney, spleen, and muscle) but does not cross the BBB efficiently (e.g., a conjugate including Angiopep-7). In some embodiments, the cells are ovary cells. The polypeptide may be of any length, for example, at least 6, 7, 8, 9, 10, 11, 12, 13, 14, 15, 16, 17, 18, 19, 20, 21, 25, 35, 50, 75, 100, 200, or 500 amino acids. In certain embodiments, the polypeptide is 10 to 50 amino acids in length. The conjugate may be substantially pure. The polypeptide may be produced by recombinant genetic technology or chemical synthesis. The conjugate can be formulated with a pharmaceutically acceptable carrier.

TABLE 1

Exemplary Polypeptides

| SEQ ID NO: | | | | | | | | | | | | | | | |
|---|---|---|---|---|---|---|---|---|---|---|---|---|---|---|---|
| 1 | T | F | V | Y | G | G | C | R | A | K | R | N | N | F | K | S | A | E | D |
| 2 | T | F | Q | Y | G | G | C | M | G | N | G | N | N | F | V | T | E | K | E |
| 3 | P | F | F | Y | G | G | C | G | G | N | R | N | N | F | D | T | E | E | Y |
| 4 | S | F | Y | Y | G | G | C | L | G | N | K | N | N | Y | L | R | E | E | E |
| 5 | T | F | F | Y | G | G | C | R | A | K | R | N | N | F | K | R | A | K | Y |
| 6 | T | F | F | Y | G | G | C | R | G | K | R | N | N | F | K | R | A | K | Y |
| 7 | T | F | F | Y | G | G | C | R | A | K | K | N | N | Y | K | R | A | K | Y |
| 8 | T | F | F | Y | G | G | C | R | G | K | K | N | N | F | K | R | A | K | Y |
| 9 | T | F | Q | Y | G | G | C | R | A | K | R | N | N | F | K | R | A | K | Y |
| 10 | T | F | Q | Y | G | G | C | R | G | K | K | N | N | F | K | R | A | K | Y |
| 11 | T | F | F | Y | G | G | C | L | G | K | R | N | N | F | K | R | A | K | Y |
| 12 | T | F | F | Y | G | G | S | L | G | K | R | N | N | F | K | R | A | K | Y |
| 13 | P | F | F | Y | G | G | C | G | G | K | K | N | N | F | K | R | A | K | Y |
| 14 | T | F | F | Y | G | G | C | R | G | K | G | N | N | Y | K | R | A | K | Y |
| 15 | P | F | F | Y | G | G | C | R | G | K | R | N | N | F | L | R | A | K | Y |
| 16 | T | F | F | Y | G | G | C | R | G | K | R | N | N | F | K | R | E | K | Y |
| 17 | P | F | F | Y | G | G | C | R | A | K | K | N | N | F | K | R | A | K | E |
| 18 | T | F | F | Y | G | G | C | R | G | K | R | N | N | F | K | R | A | K | D |
| 19 | T | F | F | Y | G | G | C | R | A | K | R | N | N | F | D | R | A | K | Y |
| 20 | T | F | F | Y | G | G | C | R | G | K | K | N | N | F | K | R | A | E | Y |
| 21 | P | F | F | Y | G | G | C | G | A | N | R | N | N | F | K | R | A | K | Y |
| 22 | T | F | F | Y | G | G | C | G | G | K | K | N | N | F | K | T | A | K | Y |
| 23 | T | F | F | Y | G | G | C | R | G | N | R | N | N | F | L | R | A | K | Y |
| 24 | T | F | F | Y | G | G | C | R | G | N | R | N | N | F | K | T | A | K | Y |
| 25 | T | F | F | Y | G | G | S | R | G | N | R | N | N | F | K | T | A | K | Y |
| 26 | T | F | F | Y | G | G | C | L | G | N | G | N | N | F | K | R | A | K | Y |
| 27 | T | F | F | Y | G | G | C | L | G | N | R | N | N | F | L | R | A | K | Y |
| 28 | T | F | F | Y | G | G | C | L | G | N | R | N | N | F | K | T | A | K | Y |
| 29 | T | F | F | Y | G | G | C | R | G | N | G | N | N | F | K | S | A | K | Y |
| 30 | T | F | F | Y | G | G | C | R | G | K | K | N | N | F | D | R | E | K | Y |
| 31 | T | F | F | Y | G | G | C | R | G | K | R | N | N | F | L | R | E | K | E |
| 32 | T | F | F | Y | G | G | C | R | G | K | G | N | N | F | D | R | A | K | Y |
| 33 | T | F | F | Y | G | G | S | R | G | K | Q | N | N | F | D | R | A | K | Y |
| 34 | T | F | F | Y | G | G | C | R | G | N | G | N | N | F | V | T | A | K | Y |
| 35 | P | F | F | Y | G | G | C | G | G | K | G | N | N | Y | V | T | A | K | Y |
| 36 | T | F | F | Y | G | G | C | L | G | K | G | N | N | F | L | T | A | K | Y |
| 37 | S | F | F | Y | G | G | C | L | G | N | K | N | N | F | L | T | A | K | Y |

TABLE 1-continued

Exemplary Polypeptides

| SEQ ID NO: | Sequence |
|---|---|
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G N R N N F K T E E Y |
| 49 | T F F Y G G C R G K R N N F K T E E D |
| 50 | P F F Y G G C G G N G N N F V R E K Y |
| 51 | S F F Y G G C M G N G N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |
| 68 | K F F Y G G C R G K R N N F K T E E Y |
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | T F F Y G G C R G K R N N F K T E E Y C |
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |
| 77 | T F F Y G G K R G K R N N F K T E E Y |
| 78 | T F F Y G G C R G K R N N F K T K R Y |
| 79 | T F F Y G G K R G K R N N F K T A E Y |
| 80 | T F F Y G G K R G K R N N F K T A G Y |
| 81 | T F F Y G G K R G K R N N F K R E K Y |
| 82 | T F F Y G G K R G K R N N F K R A K Y |
| 83 | T F F Y G G C L G N R N N F K T E E Y |
| 84 | T F F Y G C G R G K R N N F K T E E Y |
| 85 | T F F Y G G R C G K R N N F K T E E Y |
| 86 | T F F Y G G C L G N G N N F D T E E E |
| 87 | T F Q Y G G C R G K R N N F K T E E Y |
| 88 | Y N K E F G T F N T K G C E R G Y R F |
| 89 | R F K Y G G C L G N M N N F E T L E E |
| 90 | R F K Y G G C L G N K N N F L R L K Y |
| 91 | R F K Y G G C L G N K N N Y L R L K Y |
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R R F |
| 96 | R Q I K I W F Q N R R M K W K K |
| 97 | T F F Y G G S R G K R N N F K T E E Y |
| 98 | M R P D F C L E P P Y T G P C V A R I I R Y F Y N A K A G L C Q T F V Y G G C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F E S A E D C M R T C G G A |
| 103 | Y G G C R A K R N N F K S A E D C M R T C G G A |
| 104 | G L C Q T F V Y G G C R A K R N N F K S A E |
| 105 | L C Q T F V Y G G C E A K R N N F K S A |
| 107 | T F F Y G G S R G K R N N F K T E E Y |
| 108 | R F F Y G G S R G K R N N F K T E E Y |
| 109 | R F F Y G G S R G K R N N F K T E E Y |
| 110 | R F F Y G G S R G K R N N F R T E E Y |

TABLE 1-continued

Exemplary Polypeptides

| SEQ ID NO: | |
|---|---|
| 111 | T F F Y G G S R G K R N N F R T E E Y |
| 112 | T F F Y G G S R G R R N N F R T E E Y |
| 113 | C T F F Y G G S R G K R N N F K T E E Y |
| 114 | T F F Y G G S R G K R N N F K T E E Y C |
| 115 | C T F F Y G G S R G R R N N F R T E E Y |
| 116 | T F F Y G G S R G R R N N F R T E E Y C |

Polypeptides Nos. 5, 67, 76, and 91, include the sequences of SEQ ID NOS: 5, 67, 76, and 91, respectively, and are amidated at the C-terminus.
Polypeptides Nos. 107, 109, and 110 include the sequences of SEQ ID NOS: 97, 109, and 110, respectively, and are acetylated at the N-terminus.

In any of the above aspects, the polypeptide may include an amino acid sequence having the formula:

X1-X2-X3-X4-X5-X6-X7-X8-X9-X10-X11-X12-X13-X14-X15-X16-X17-X18-X19 where each of X1-X19 (e.g., X1-X6, X8, X9, X11-X14, and X16-X19) is, independently, any amino acid (e.g., a naturally occurring amino acid such as Ala, Arg, Asn, Asp, Cys, Gln, Glu, Gly, His, Ile, Leu, Lys, Met, Phe, Pro, Ser, Thr, Trp, Tyr, and Val) or absent and at least one (e.g., 2 or 3) of X1, X10, and X15 is arginine. In some embodiments, X7 is Ser or Cys; or X10 and X15 each are independently Arg or Lys. In some embodiments, the residues from X1 through X19, inclusive, are substantially identical to any of the amino acid sequences of any one of SEQ ID NOS:1-105 and 107-116 (e.g., Angiopep-1, Angiopep-2, Angiopep-3, Angiopep-4a, Angiopep-4b, Angiopep-5, Angiopep-6, and Angiopep-7). In some embodiments, at least one (e.g., 2, 3, 4, or 5) of the amino acids X1-X19 is Arg. In some embodiments, the polypeptide has one or more additional cysteine residues at the N-terminal of the polypeptide, the C-terminal of the polypeptide, or both.

In certain embodiments of any of the above aspects, the polypeptide is modified (e.g., as described herein). The polypeptide may be amidated, acetylated, or both. Such modifications to polypeptides may be at the amino or carboxy terminus of the polypeptide. The conjugates of the invention may also include peptidomimetics (e.g., those described herein) of any of the polypeptides described herein. The polypeptide may be in a multimeric form, for example, dimeric form (e.g., formed by disulfide bonding through cysteine residues).

In certain embodiments, the polypeptide has an amino acid sequence described herein with at least one amino acid substitution (e.g., 2, 3, 4, 5, 6, 7, 8, 9, 10, 11, or 12 substitutions). The polypeptide may contain, for example, 1 to 12, 1 to 10, 1 to 5, or 1 to 3 amino acid substitutions, for example, 1 to 10 (e.g., to 9, 8, 7, 6, 5, 4, 3, 2) amino acid substitutions. The amino acid substitution(s) may be conservative or non-conservative. For example, the polypeptide may gave an arginine at one, two, or three of the positions corresponding to positions 1, 10, and 15 of the amino acid sequence of any of SEQ ID NO:1, Angiopep-1, Angiopep-2, Angiopep-3, Angiopep-4a, Angiopep-4b, Angiopep-5, Angiopep-6, and Angiopep-7.

In any of the above aspects, the conjugate may specifically exclude a polypeptide including or consisting of any of SEQ ID NOS:1-105 and 107-116 (e.g., Angiopep-1, Angiopep-2, Angiopep-3, Angiopep-4a, Angiopep-4b, Angiopep-5, Angiopep-6, and Angiopep-7). In some embodiments, the polypeptides and conjugates of the invention exclude the polypeptides of SEQ ID NOs:102, 103, 104, and 105.

In some embodiments, the amino acid sequence has at least 35%, 40%, 50%, 60%, 65%, 70%, 75%, 80%, 85%, 90%, or 95% identity to an amino acid sequence selected from the group consisting of SEQ ID NOS:1-105 and 107-116, or a functional derivative thereof. In certain embodiments, the amino acid sequence has at least 35%, 40%, 50%, 60%, 65%, 70%, 75%, 80%, 85%, 90%, or 95% identity to an amino acid sequence selected from the group consisting of Angiopep-2 (SEQ ID NO:97), Angiopep-4b, Angiopep-5, Angiopep-6, and Angiopep-7 (SEQ ID NOS:109-112). In still other embodiments, the amino acid sequence has at least 35%, 40%, 50%, 60%, 65%, 70%, 75%, 80%, 85%, 90%, or 95% identity to an amino acid sequence of Angiopep-2 (SEQ ID NO:97).

In some embodiments, the amino acid sequence comprises the amino acid sequence selected from the group consisting of SEQ ID NOS:1-105 and 107-116, or a functional derivative thereof. In certain embodiments, the amino acid sequence is that of Angiopep-2 (SEQ ID NO:97), Angiopep-4b, Angiopep-5, Angiopep-6, or Angiopep-7 (SEQ ID NOS:109-112).

In still other embodiments, the amino acid sequence consists of the amino acid sequence selected from the group consisting of SEQ ID NOS:1-105 and 107-116, or a functional derivative thereof. In certain embodiments, the amino acid sequence is that of Angiopep-2 (SEQ ID NO:97), Angiopep-4b, Angiopep-5, Angiopep-6, or Angiopep-7 (SEQ ID NOS:109-112).

In some embodiments, the compounds of the invention can alter the accumulation of a biologically active agent (e.g., podophyllotoxin derivatives such as the compounds of Formula (I) or doxorubicin derivatives such as the compounds of Formula (II)) in a target cell type or tissue relative to the corresponding unconjugated biologically active agent. In still other embodiments, the compound of the invention promotes accumulation of the biologically active agent in a target cell type or tissue. In certain embodiments, the concentration of the biologically active agent increases by 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1,000%, 2,000%, 3,000%, 4,000%, 5,000%, 6,000%, 7,000%, 8,000%, 9,000%, 10,000%, 12500%, 15,000%, 17,500%, or 20,000% relative to that observed with the unconjugated biologically active agent. In some embodiments, the target cell type or tissue is the brain, ovary, liver, lung, kidney, spleen, or muscle. In some embodiments, the target cell type is the brain or the ovary. In certain embodiments, the biologically active agent is selected from etoposide, etoposide phosphate, etoposide$_{DMG}$, teniposide, doxorubicin, or epirubicin. In other embodiments, the compound of the invention includes the amino acid sequence of Angiopep-2 (SEQ ID NO:97), Angiopep-4b, Angiopep-5, Angiopep-6, or Angiopep-7 (SEQ ID NOS:109-112), or a functional derivative thereof.

In a third aspect, the invention features a pharmaceutical composition that includes any compound of the invention as described herein (e.g., a compound that includes an amino acid sequence substantially identical to an amino acid sequence selected from the group consisting of SEQ ID NOS: 1-105 and 107-116, or a functional derivative or pharmaceutically acceptable salt thereof, where the amino acid sequence includes a covalent bond from an amino acid of the amino acid sequence to a compound of Formulas (I) or (II) (e.g., Compound (1) or (2)) and a pharmaceutically acceptable carrier. In a fourth aspect, the invention features a method of treating or treating prophylactically a cancer, where the method includes administering to a patient a therapeutically effective amount of any compound of the invention as described herein (e.g., a compound that includes an amino acid sequence substantially identical to an amino acid sequence selected from the group consisting of SEQ ID NOS: 1-105 and 107-116, or a functional derivative thereof, where the amino acid sequence includes a covalent bond from an amino acid of the amino acid sequence to a compound of Formulas (I) or (II)). In some embodiments, the compound is Compound (1) or (2). In some embodiments, the podophyllotoxin derivative is selected from

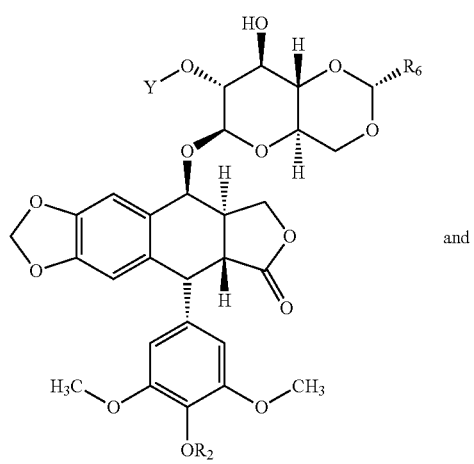

and

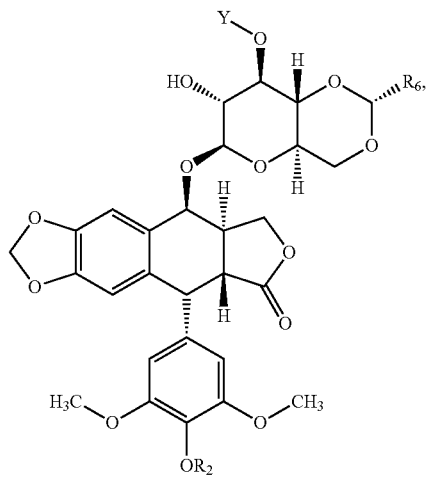

where

Y is H; each $R_2$ is, independently, H or P(O)(OH)$_2$, or —C(O)$R_8$; each $R_6$ is, independently, $CH_3$ or 2-thiophene; each Y is —C(O)(CH$_2$)$_n$C(O)—; each $R_8$ is, independently, optionally substituted $C_{1-6}$ alkyl; and each n is, independently, 2, 3, or 4. In some embodiments, n is 3. In some embodiments, each $R_2$ is —C(O)$R_8$. In some embodiments, $R_8$ is a $C_{1-6}$ alkyl that includes an least one optionally substituted amino group (e.g., NH$_2$ or N(CH$_3$)$_2$). In certain embodiments —C(O)$R_8$ is a C-linked amino acid. In some embodiments, the podophyllotoxin derivative is etoposide, etoposide phosphate, etoposide dimethylglycine (etoposide$_{DMG}$), or teniposide. In still other embodiments, the compound is doxorubicin or any of the doxorubicin derivatives (e.g., a compound of Formula (II)) described herein.

In some embodiments, the method also includes the administration of a second agent. In still other embodiments, the agent is a therapeutic agent. In certain embodiments, the second therapeutic agent is also covalently bonded to the compound of the invention. In still other embodiments, the second therapeutic agent is not covalently bonded to the compounds of the invention. In some embodiments, the therapeutic agent is drug, a medicine, an agent emitting radiation, a cellular toxin, a biologically active fragment thereof, or a mixture thereof to treat a disease. In other embodiments, the administering is concurrent with another therapeutic regime. In some embodiments, the therapeutic regime is radiation therapy, chemotherapy, stem cell transplantation, bone marrow transplant, surgery, or hyperthermia treatment. In some embodiments, the second therapeutic agent is a polypeptide that includes or that consists of the sequence of Angiopep-2 (SEQ ID NO:97), preferably where the Angiopep-2 is conjugated to an anticancer agent (e.g., paclitaxel), e.g., ANG1005, which has the following structure:

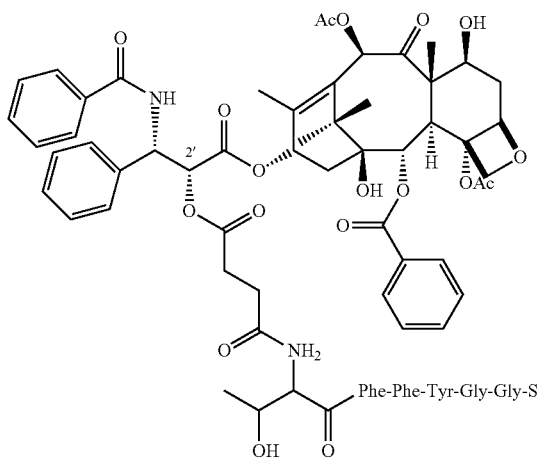 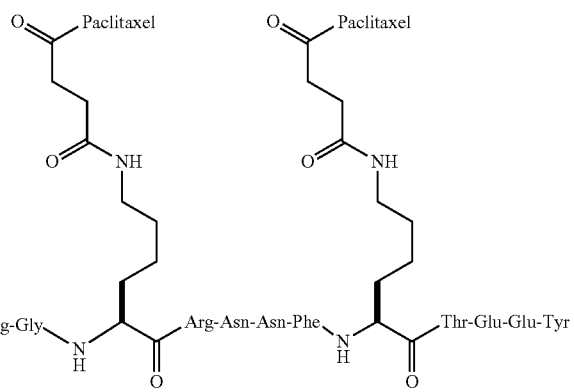

ANG1005:
TxlAn2 (3:1 conjugate)

Still other exemplary second therapeutic agents are described in U.S. Pat. No. 7,557,182, herein incorporated by reference.

In some embodiments, the cancer is cancer of the brain. In other embodiments, the cancer of the brain is glioblastoma, a glioma, an acoustic neuroma, an adenoma, an astrocytoma, a choroid plexus papilloma, CNS lymphoma, ependymoma, a gangliocytoma, a ganglioglioma, a medulloblastoma (mdl), an anaplastic (malignant) meningioma, or neurofibromatosis. In still other embodiments, the cancer is acute lymphocytic leukemia, acute myeloblastic leukemia, adrenocortical cancer, intravenous and intravesical bladder cancer, bone sarcoma, breast cancer, carcinoid syndrome (small bowel), endometrial cancer, Ewing's sarcoma, gynecological sarcoma, head and neck cancer (squamous cell), hepatic cancer, Hodgkin's disease, islet cell cancer, leukemia, lung cancer, malignant lymphoma, multiple myeloma, neuroblastoma, non-Hodgkin's lymphoma, pancreatic cancer, prostate cancer, osteogenic sarcoma, ovarian cancer, retinoblastoma, rhabdomyosarcoma, stomach cancer, testicular cancer, thyroid cancer, transitional cell bladder carcinoma, soft tissue sarcoma, or Wilms' tumor.

In any of therapeutic methods described herein, the compound of the invention (e.g., Compound (1) or (2)), or a pharmaceutically acceptable salt thereof, can be administered to a patient as a subtherapeutic dose or a supertherapeutic dose relative to the unconjugated therapeutic agent (e.g., etoposide, etoposide phosphate, etoposide 4-dimethylglycine, or doxorubicin).

In another aspect, the invention features a method of making any of the compounds of the invention described herein, where the method includes the step of covalently binding a podophyllotoxin derivative to any amino acid sequence described herein, or functional derivative thereof, using a difunctional hydrolyzable linking group. In some embodiments, the amino acid sequence is selected from SEQ ID NOS:1-105 and 107-116, or a functional derivative thereof. In other embodiments, the amino acid sequence includes the amino acid sequence of Angiopep-2 (SEQ ID NO:97), Angiopep-4b, Angiopep-5, Angiopep-6, or Angiopep-7 (SEQ ID NOS:109-112).

In some embodiments, the method of making any of the compounds of the invention includes the steps of
(a) combining said compound of Formula (I) with said difunctional hydrolyzable linking group to form a covalent adduct; and (b) combining the adduct of (a) with said amino acid sequence; and
where the adduct of (a) may be optionally purified prior to use in (b).

In some embodiments, 1.0-10.0 equivalents of the difunctional hydrolyzable linking group is used relative to the compound of Formula (I).

For example, 1.1, 1.2, 1.3, 1.4, 1.5, 1.6, 1.7, 1.8, 1.9, 2.0. 2.1, 2.2., 2.3, 2.4, 2.5, 2.6, 2.7, 2.8, 2.9, or 3.0 equivalents can be used. In other embodiments, 3.5, 4.0, 4.5, 5.0, 5.5, 6.0, 6.5, 7.0. 7.5, 8.0, 8.5, 9.0, 9.5, or 10.0 equivalents the difunctional hydrolyzable linking group is used. In certain embodiments, the method includes the use of a peptide coupling agent. In some embodiments, peptide coupling agent is N,N,N',N'-Tetramethyl-O-(benzotriazol-1-yl)uronium tetrafluoroborate (TBTU).

In some embodiments, the hydrolyzable difunctional linking group is selected from dicarboxylic acids, dicarbonates, carboxylic anhydrides, diisocyanates, or diphosphonic acids. In certain embodiments, the hydrolyzable difunctional linking group is selected from succinic acid, glutaric acid, glutaric anhydride, or butaric acid.

In some embodiments, the podophyllotoxin derivative is selected from:

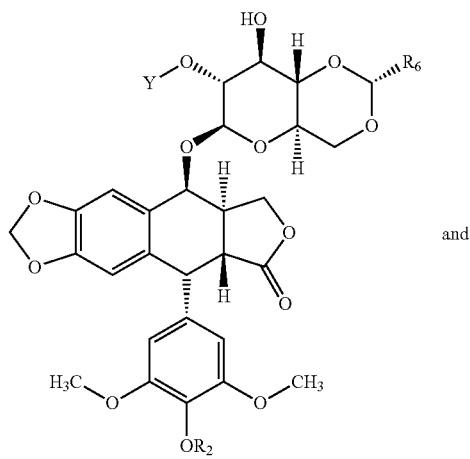

and

-continued

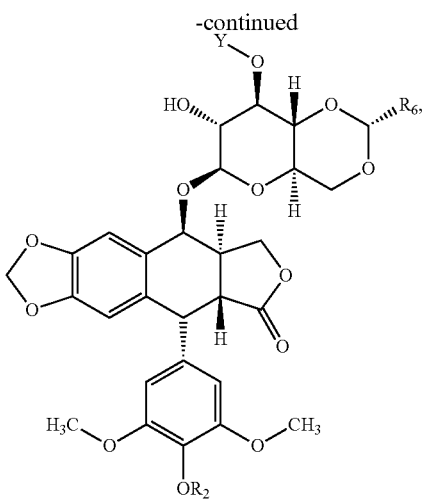

where

Y is H; each $R_2$ is, independently, H or $P(O)(OH)_2$, or —$C(O)R_8$; each $R_6$ is, independently, $CH_3$ or 2-thiophene; each Y is —$C(O)(CH_2)_nC(O)$—; each $R_8$ is, independently, optionally substituted $C_{1-6}$ alkyl; and each n is, independently, 2, 3, or 4. In some embodiments, n is 3. In some embodiments, each $R_2$ is —$C(O)R_8$. In some embodiments, $R_5$ is a $C_{h6}$ alkyl that includes an least one optionally substituted amino group (e.g., $NH_2$ or $N(CH_3)_2$). In certain embodiments —$C(O)R_8$ is a C-linked amino acid. In some embodiments, the podophyllotoxin derivative is etoposide, etoposide phosphate, etoposide$_{DMG}$, or teniposide.

In any of the methods or compositions described herein, the pharmaceutically acceptable salt of the compound can be the mono-, di-, tri-, or tetra acid addition salt (e.g., the trihydrochloride salt). In any of the embodiments described herein, any of the compounds of Formula (I) or (II) (e.g., etoposide, etoposide$_{DMG}$, or doxorubicin) that is covalently bonded to the polypeptide is the site of protonation. For example, in Compound (1), 1, 2, or 3 of the etoposide$_{DMG}$ moieties is protonated, or in Compound (2), 1, 2, or 3 of the doxorubicin moieties, is protonated to form the acid addition salt (e.g., the mono-, di-, or trihydrochloride salt).

The term "$C_{1-6}$ alkyl" or "alkyl" as used herein refers to an optionally substituted $C_{1-6}$ saturated hydrocarbon group. An alkyl group may be linear or branched. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. For example, substituted alkyl groups may have 1, 2, 3, 4, 5, or 6 substituents.

The term "aryl" as used herein refers to an optionally substituted mono- or polycyclic, aromatic all-carbon moiety having 5-14 carbon atoms. In certain embodiments of the present invention, "aryl" refers to a substituted or unsubstituted monocyclic or bicyclic group. Exemplary aryl groups include, but are not limited to, phenyl, naphthyl, tetrahydronaphthyl, indanyl, indenyl, and the like, which may bear one or more substituents. Aryls also include heteroaryls.

The term "C-linked amino acid" as used herein refers to an amino acid that is covalently attached to another compound (e.g., any of the podophyllotoxin derivatives described herein) by the C-terminus of the amino acid.

The term "$C_{3-10}$ cycloalkyl" or "cycloalkyl" as used herein refers to an optionally substituted saturated 3- to 10-membered monocyclic or bicyclic hydrocarbon ring system. Exemplary cycloalkyls include cyclopropyl, cyclobutyl, cyclopentyl, cyclohexyl, and cycloheptyl. A substituted cycloalkyl can have, for example, 1, 2, 3, 4, 5, 6, or 7 substituents.

The term "heteroaryl" as used herein refers to a substituted or unsubstituted mono- or polycyclic, aromatic moiety having 5-14 ring atoms of which one, two, three, or four ring atoms may be selected from S, O, and N and the remaining ring atoms are carbon. Exemplary heteroaryl groups include, but are not limited to, pyrrolyl, pyrazolyl, imadazolyl, pyridinyl, pyrimidinyl, pyrazinyl, pyridazinyl, triazinyl, tetrazinyl, pryyrolizinyl, indolyl, quinolinyl, isoquinolynyl, benzimidazolyl, indazolyl, quinolizinyl, cinnolinyl, quinazolinyl, phthalazinyl, napthyridinyl, quinoxalinyl, thiophenyl, thiepinyl, furanyl, benzofuranyl, thiazolyl, isothiazolyl, thiadiazolyl, oxazolyl, isoxazolyl, oxadiazolyl, and the like, which may bear one or more substituents.

The term "heterocyclic," or "heterocyclyl," as used herein, refers to an optionally substituted non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized or substituted. In certain embodiments, the term heterocyclic refers to a non-aromatic 5-, 6-, or 7-membered monocyclic ring wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Exemplary heterocyclics include, but are not limited to, azacyclopropanyl, azacyclobutanyl, 1,3-diazatidinyl, pyrrolidinyl, piperidinyl, piperazinyl, thiranyl, thietanyl, tetrahydrothiophenyl, dithiolanyl, tetrahydrothiopyranyl, oxiranyl, oxetanyl, tetrahydrofuranyl, tetrahydropyranyl, dioxanyl, oxathiolanyl, morpholinyl, thiomorpholinyl, thioxanyl, quinuclidinyl, and the like, which may bear one or more substituents.

The term "pharmaceutically acceptable salt," as use herein, represents those acid addition salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting a compound having one or basic groups (e.g., 1, 2, 3, 4, 5, 6, 7, 8, 9, or 10) with the desired equivalents of a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, trifluoromethylsulfonate, undecanoate, and valerate salts, and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like. Desirably, the "pharmaceutically acceptable acid addition salt" is the mono-, bis-, tri-, or tetra acid addition salt of any of the compounds described herein (e.g., a mono-, bis-, tris-, or tetrahydrochloride salt of any of the compounds described herein).

The term "phosphate" as used herein refers to a pentavalent phosphorous group having the formula —OP(=O)(OR')(OR''), where each R' and R'' is selected, independently, from hydrogen, $C_{1-6}$ alkyl, $C_{2-6}$ alkenyl, $C_{2-6}$ alkynyl, $C_{3-10}$ cycloalkyl, heterocyclyl, aryl, or heteroaryl.

Where a group is described as "optionally substituted," the optional substituents may be selected, independently, from groups that include, but are not limited to: $C_{1-6}$ alkyl; halogen; azido(—$N_3$), nitro (—$NO_2$), cyano (—CN), acyloxy, acyl (—C(O)R), (—OC(O)R), alkoxy (—OR), amido (—NRC(O)R' or —C(O)NRR'), amino (—NRR'), aryl, carboxylic acid (—$CO_2H$), carboxylic ester (—$CO_2R$), carbamoyl (—OC(O)NRR' or —NRC(O)OR'), cycloalkyl, heterocyclyl, hydroxy (—OH), isocyano (—NC), phosphate (—P(O)(OR)(OR')), sulfonate (—$SO_2OR$), or sulfonyl (—$SO_2R$), where each R or R' is selected, independently, from H, $C_{1-6}$ alkyl, cycloalkyl, heterocyclyl, aryl, or heteroaryl. A substituted group may have, for example, 1, 2, 3, 4, 5, 6, 7, 8, or 9 substituents. In some embodiments, a substituent group may itself be further substituted by replacing a hydrogen with a substituent group such as those described herein.

By "vector" is meant a compound or molecule such as a polypeptide that is able to be transported into a particular cell type (e.g., liver, ovary, lungs, kidney, spleen, or muscle) or across the BBB. The vector may be attached to (covalently or not) or conjugated to an agent and thereby may be able to transport the agent into a particular cell type or across the BBB. In certain embodiments, the vector may bind to receptors present on cancer cells or brain endothelial cells and thereby be transported into the cancer cell or across the BBB by transcytosis. The vector may be a molecule for which high levels of transendothelial transport may be obtained, without affecting the cell or BBB integrity. The vector may be a polypeptide or a peptidomimetic and may be naturally occurring or produced by chemical synthesis or recombinant genetic technology.

By "conjugate" is meant a vector linked to an agent. The conjugation may be chemical in nature, such as via a linker, or genetic in nature for example by recombinant genetic technology, such as in a fusion protein with for example a reporter molecule (e.g., green fluorescent protein, β-galactosidase, Histag, etc.).

By a vector which is "efficiently transported across the BBB" is meant a vector that is able to cross the BBB at least as efficiently as AngioPep-6 (i.e., greater than 38.5% that of AngioPep-1 (250 nM) in the in situ brain perfusion assay described herein). Accordingly, a vector or conjugate which is "not efficiently transported across the BBB" is transported to the brain at lower levels (e.g., transported less efficiently than AngioPep-6).

By a vector or conjugate which is "efficiently transported to a particular cell type" is meant a vector or conjugate that is able to accumulate (e.g., either due to increased transport into the cell, decreased efflux from the cell, or a combination thereof) in that cell type at least 10% (e.g., 25%, 50%, 100%, 200%, 500%, 1,000%, 5,000%, or 10,000%) greater extent than either a control substance, or, in the case of a conjugate, as compared to the unconjugated agent.

By "substantially pure" or "isolated" is meant a compound (e.g., a polypeptide or conjugate) that has been separated from other chemical components. Typically, the compound is substantially pure when it is at least 30%, by weight, free from other components. In certain embodiments, the preparation is at least 50%, 60%, 75%, 85%, 90%, 95%, 96%, 97%, 98%, or 99% by weight, free from other components. A purified polypeptide may be obtained, for example, by expression of a recombinant polynucleotide encoding such a polypeptide or by chemically synthesizing the polypeptide. Purity can be measured by any appropriate method, for example, column chromatography, polyacrylamide gel electrophoresis, or by HPLC analysis.

By "analogue" is meant a polypeptide originating from an original sequence or from a portion of an original sequence and which may include one or more modification; for example, one or more modification in the amino acid sequence (e.g., an amino acid addition, deletion, insertion, or substitution), one or more modification in the backbone or side-chain of one or more amino acid, or an addition of a group or another molecule to one or more amino acids (side-chains or backbone). An analogue may have one or more amino acid insertions, at either or at both of the ends of the polypeptide or inside the amino acid sequence of the polypeptide. An analogue may have sequence similarity and/or sequence identity (e.g., may be substantially identical) with that of an original sequence or a portion of an original sequence. Analogues may include a modification of its structure, e.g., as described herein. The degree of similarity between two sequences is base upon the percentage of identities (identical amino acids) and of conservative substitution. An analogue may have at least 35%, 50%, 60%, 70%, 80%, 90%, or 95% (e.g., 96%, 97%, 98%, 99%, and 100%) sequence similarity to an original sequence with a combination of one or more modifications in a backbone or side-chain of an amino acid, or an addition of a group or another molecule. Exemplary amino acids which are intended to be similar (a conservative amino acid) to others are known in the art and include, for example, those listed in Table 3.

By "substantially identical" is meant a polypeptide or nucleic acid exhibiting at least 35%, 40%, 50%, 55%, 60%, 65%, 70%, 75%, 85%, 90%, 95%, or even 99% identity to a reference amino acid or nucleic acid sequence. For polypeptides, the length of comparison sequences will generally be at least 4 (e.g., at least 5, 6, 7, 8, 9, 10, 11, 12, 13, 14, 15, 16, 17, 18, 19, 20, 25, 50, or 100) amino acids. For nucleic acids, the length of comparison sequences will generally be at least 60 nucleotides, preferably at least 90 nucleotides, and more preferably at least 120 nucleotides, or full length. It is to be understood herein that gaps may be found between the amino acids of an analogs which are identical or similar to amino acids of the original polypeptide. The gaps may include no amino acids, one or more amino acids which are not identical or similar to the original polypeptide. Biologically active analogs of the vectors (polypeptides) of the invention are encompassed herewith. Percent identity may be determined, for example, with n algorithm GAP, BESTFIT, or FASTA in the Wisconsin Genetics Software Package Release 7.0, using default gap weights.

By "functional derivative" is meant a "chemical derivative," "fragment," or "variant" biologically active sequence or portion of a vector or agent or conjugate and a salt thereof of the invention. A vector functional derivative may be able to be attached to or conjugated to an agent and enter a particular cell type, thereby transporting the agent into that cell.

By "chemical derivative" is meant a vector, an agent, or a conjugate of the invention, which contains additional chemical moieties not a part of the vector, agent or vector-agent conjugate, including covalent modifications. A chemical derivative may be prepared by direct chemical synthesis using methods known in the art. Such modifications may be introduced into a protein or peptide vector, agent, or vector-agent conjugate by reacting targeted amino acid residues with an organic derivatizing agent capable of reacting with selected side chains or terminal residues. A vector chemical derivative may be able to cross the BBB or to enter or accumulate in a particular cell type (e.g., those described herein such as the ovary). In a preferred embodiment, very high levels of transendothelial transport across the BBB are obtained without effecting BBB integrity.

By "fragment" is meant a polypeptide originating from a portion of an original or parent sequence or from an analogue of said parent sequence. Fragments encompass polypeptides having truncations of one or more amino acids, wherein the truncation may originate from the amino terminus (N-terminus), carboxy terminus (C-terminus), or from the interior of the protein. A fragment may include the same sequence as the corresponding portion of the original sequence. Functional fragments of the vector (polypeptide) described herein are encompassed by the invention. Fragments may be at least 5 (e.g., at least 5, 6, 7, 8, 9, 10, 11, 12, 13, 14, 15, 16, 17, 18, 19, 20, 21, 22, 23, 25, 28, 30, 35, 40, 45, 50, 60, 75, 100, or 150) amino acids. Fragments of the invention may include, for example, a polypeptide of 7, 8, 9 or 10 amino acids to 18 amino acids. Fragments may contain any of the modifications described herein (e.g., acetylation, amidation, amino acid substitutions)

A "non-naturally occurring amino acid" is an amino acid which is not naturally produced or found in a mammal.

By "agent" is meant, any compound, for example, an antibody, or a therapeutic agent, a marker, a tracer, or an imaging compound.

By "therapeutic agent" is meant an agent having a biological activity. In some cases, the therapeutic agent is used to treat the symptoms of a disease, a physical or mental condition, an injury, or an infection and includes anti-cancer agents, antibiotics, anti-angiogenic agents, and molecules active at the level of the central nervous system.

By "small molecule drug" is meant a drug having a molecular weight of 1000 g/mol or less (e.g., less than 800, 600, 500, 400, or 200 g/mol).

By "subject" is meant a human or non-human animal (e.g., a mammal).

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence of (e.g., preventing) a disease, disorder or condition by administering a therapeutic agent to the subject.

By "cancer" is meant any cellular proliferation whose unique trait is the loss of normal controls which can result in unregulated growth, lack of differentiation, or ability to invade tissues and metastasize. Cancer can develop in any tissue or in any organ. Cancer is intended to include, without limitation, cancer of the brain, ovary, liver, lungs, kidney, or spleen. Additional cancers are described herein.

By "providing" is meant, in the context of a vector or conjugate of the invention, to bring the vector or conjugate into contact with a target cell or tissue either in vivo or in vitro. A vector or conjugate may be provided by administering the vector or conjugate to a subject.

By "administering" and "administration" is meant a mode of delivery including, without limitation, intra-arterially, intra-nasally, intraperitoneally, intravenously, intramuscularly, subcutaneously, transdermally or per os. A daily dosage can be divided into one, two or more doses in a suitable form to be administered at one, two or more times throughout a time period.

By "therapeutically effective" or "effective amount" is meant an amount of a therapeutic agent sufficient to improve, decrease, prevent, delay, suppress, or arrest any symptom of the disease or condition being treated. A therapeutically effective amount of an agent need not cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual. A "subtherapeutic dose" is a dose less than the minimum effective amount of a therapeutic agent that has been approved for clinical use by a patient. A "supertherapeutic dose" is a dose greater than the maximum effective amount of a therapeutic agent that has been approved for clinical use by a patient. The amount of a subtherapeutic dose or a supertherapeutic dose may vary according to the patient demographics (e.g., adult, pediatric, or geriatric) or when used in conjunction with the administration of additional therapeutic agents (e.g., when administered concurrently with other therapeutic agents or treatment regimes such as, for example, in cancer chemotherapy).

By "condition" is meant any situation causing pain, discomfort, sickness, disease or disability (mental or physical) to or in an individual, including neurological disease, injury, infection, or chronic or acute pain. Neurological diseases include brain tumors, brain metastases, schizophrenia, epilepsy, Alzheimer's disease, Parkinson's disease, Huntington's disease, and stroke.

By "pharmaceutical composition" is meant a therapeutically effective amount of an agent together with a pharmaceutically acceptable diluents, preservative, solubilizer, emulsifier, or adjuvant, for example, any of those described herein.

By "therapeutic dose" is meant the dosage of a agent such as a drug (without the vector) acceptable for use clinically with respect to its toxicity or efficacy. By conjugation of an agent to a vector of the invention, it may be possible to administer the agent at a dosage either lower or higher dosage than the therapeutic dose.

If a "range" or "group of substances" is mentioned with respect to a particular characteristic (e.g., temperature, concentration, time and the like), the invention relates to and explicitly incorporates herein each and every specific member and combination of sub-ranges or sub-groups therein. Thus, for example, with respect to a length of from 9 to 18 amino acids, is to be understood as specifically incorporating herein each and every individual length, e.g., a length of 18, 17, 15, 10, 9, and any number there between. Therefore, unless specifically mentioned, every range mentioned herein is to be understood as being inclusive. For example, in the expression from 5 to 19 amino acids long is to be as including 5 and 19. This similarly applies with respect to other parameters such as sequences, length, concentrations, elements, and the like.

The sequences, regions, portions defined herein each include each and every individual sequence, region, and portion described thereby as well as each and every possible sub-sequence, sub-region, and sub-portion whether such sub-sequences, sub-regions, and sub-portions are defined as positively including particular possibilities, as excluding particular possibilities or a combination thereof. For example, an exclusionary definition for a region may read as follows: "provided that said polypeptide is no shorter than 4, 5, 6, 7, 8 or 9 amino acids. A further example of a negative limitation is the following; a sequence including SEQ ID NO:X with the exclusion of a polypeptide of SEQ ID NO:Y; etc. An additional example of a negative limitation is the following; provided that said polypeptide is not (does not include or consist of) SEQ ID NO:Z.

Other features and advantages of the invention will be apparent from the following Detailed Description, the drawings, and the claims.

BRIEF DESCRIPTION OF THE DRAWINGS

FIG. 13A shows the results obtained in the first trial (Trial 1). FIG. 13B shows the results obtained in the second trial (Trial 2) showing that the administration of Compound (2) results in a statistically significant extension of mean survival time.

DETAILED DESCRIPTION OF THE INVENTION

Figure 1:
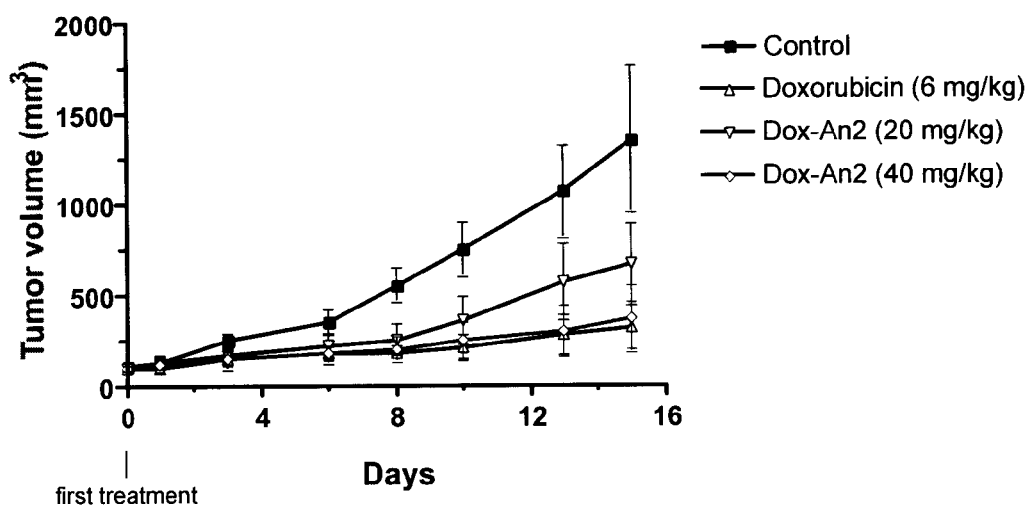
FIG. 1 shows inhibition of subcutaneous U87 (s.c. U87) xenograft tumor growth using the doxorubicin-An2(3:1) ("Doxorubicin-An2(3:1)") conjugate.

The invention features compounds, or any pharmaceutically acceptable salt thereof, that include an amino acid sequence substantially identical to an amino acid sequence selected from the amino acid sequences described herein (e.g., SEQ ID NOS:1-105 and 107-116), or a functional derivative thereof, where said amino acid sequence includes a covalent bond from an amino acid of the amino acid sequence to an anti-cancer agent (e.g., podophyllotoxin derivatives, doxorubicin, or doxorubicin derivatives). Exemplary podophyllotoxin derivatives include, for example, a compound having a structure according to Formula (I):

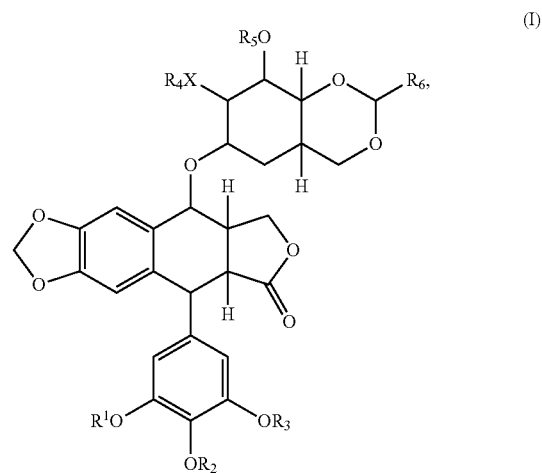

(I)

or a stereoisomer or pharmaceutically acceptable salt thereof, where each $R_1$, $R_2$, and $R_3$ is selected, independently, from H, optionally substituted $C_{1-6}$ alkyl, $C(O)R_8$ (e.g., $C(O)CH_2N(CH_3)_2$), $P(O)(OR_9)(OR_{10})$, $S(O)_2(OR_9)$, or a hydrolyzable linker Y that includes a covalent bond to an amino acid of the polypeptide;

X is O or $NR_7$;

each $R_4$, $R_5$, and $R_7$ is selected, independently, from H, optionally substituted $C_{1-6}$ alkyl, $C(O)R_8$, or a hydrolyzable linker Y that includes a covalent bond to an amino acid of the polypeptide;

$R_6$ is H, optionally substituted $C_{1-6}$ alkyl, optionally substituted aryl, optionally substituted heteroaryl, $R_8$ is selected from optionally substituted $C_{1-6}$ alkyl (e.g., $CH_2N(CH_3)_2$) or optionally substituted aryl;

each $R_9$ and $R_{10}$ is selected, independently, from H, optionally substituted $C_{1-6}$ alkyl, or optionally substituted aryl; and n is 2, 3, or 4; and where one of $R_1$, $R_2$, $R_3$, $R_4$, $R_5$, and $R_7$ is Y. In some embodiments, no more than one of $R_1$, $R_2$, $R_3$, $R_4$, $R_5$, and $R_7$ is Y. In some embodiments, Y is —C(O)(CH$_2$)$_n$C(O)—. In some embodiments, each $R_2$ is H or $C(O)CH_2N(CH_3)_2$. In certain embodiments, the polypeptide may have at least 35%, 40%, 50%, 60%, 70%, 80%, 90%, 95%, 99%, or even 100% identity to a polypeptide described herein. The polypeptide may have one or more (e.g., 2, 3, 4, 5, 6, 7, 8, 9, 10, 11, 12, 13, 14, or 15) substitutions relative to one of the sequences described herein. In certain embodiments, the amino acid sequence is covalently bonded to additional podophyllotoxin derivatives (e.g., a compound of Formula (I)) through a second, third, fourth, fifth, or even sixth amino acid of said amino acid sequence and at any position of the amino acid sequence.

Exemplary compounds of the invention include, but are not limited to, those having a polypeptide sequence according to (SEQ ID NO:97). In some embodiments, the compounds have the following structure:

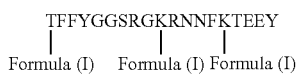

wherein each (—(Formula (I)) represents a covalent bond between the indicated amino acid and a compound of Formula (I). In certain embodiments, the compounds of Formula (I) have the following structure:

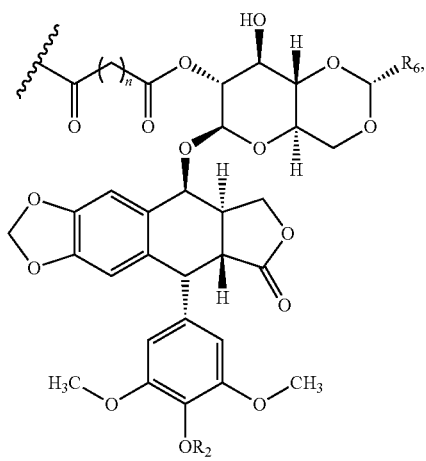

where n is 1, 2, or 3, $R_6$ is $CH_3$ or 2-thienyl, and $R_2$ is H, —OP(O)(OH)$_2$, or —C(O)CH$_2$N(CH$_3$)$_2$, or any pharmaceutically acceptable salts thereof. In some embodiments, n is 3, $R_6$ is $CH_3$, and $R_2$ is H. In other embodiments, n is 3, $R_6$ is $CH_3$, and $R_2$ is —C(O)CH$_2$N(CH$_3$)$_2$.

Other embodiments are described in greater detail below.

Podophyllotoxin Derivatives

Podophyllotoxin derivatives include compounds such as those described by Formula (I), e.g., etoposide, teniposide, and derivatives thereof, or a pharmaceutically acceptable salt thereof. Podophyllotoxin derivatives are exemplary therapeutic agents and can be covalently bonded to an amino acid in any of the polypeptides described herein (e.g., Angiopep-2). These compounds can have, for example, antineoplastic activity, inhibit the activity of topoisomerase II, or have antiviral activity.

Etoposide and Etoposide Derivatives

Etoposide (also known as Toposar, Vepesid, or VP16) is a podophyllotoxin derivative having the following structure

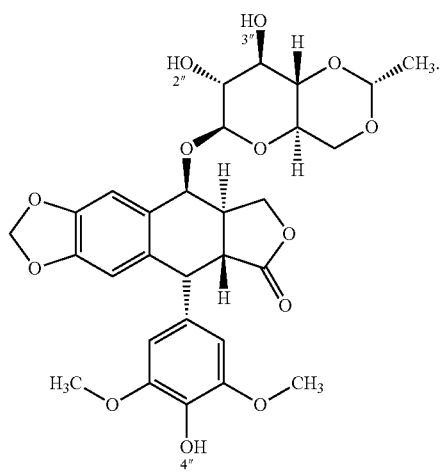

The chemical structure of etoposide can be varied to afford etoposide derivatives. An exemplary derivative of etoposide is etoposide phosphate (ETOPOPHOS®), where the phenolic —OH is replaced with —OP(O)(OH)$_2$, or any pharmaceutically acceptable salt thereof (e.g., —OP(O)(ONa)$_2$). Etoposide phosphate has improved water solubility compared to etoposide.

Other etoposide derivatives include those where the phenolic —OH is replaced with an acyloxy group (e.g., —OC(O)R$_8$, as described herein) such as the following compound:

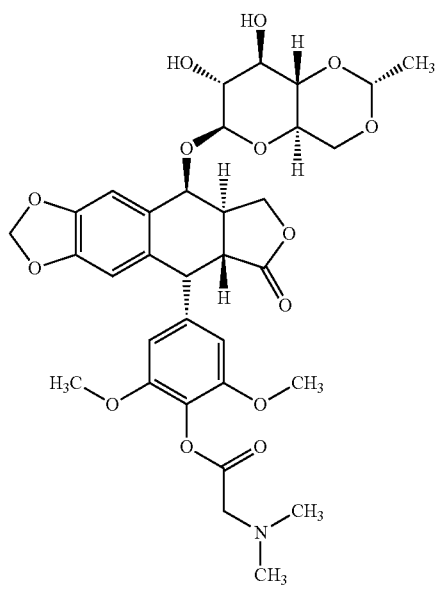

("etoposide 4'-dimethylglycine" or "etoposide$_{DMG}$").

These acylated etoposide derivatives can also show improved water solubility relative to etoposide when covalently attached to any of the polypeptides described herein.

Etoposide, etoposide phosphate, etoposide$_{DMG}$, or derivatives thereof, can be covalently attached to an amino acid in a polypeptide by attaching a hydrolyzable covalent linker Y to, for example, the 2" hydroxyl or the 3" hydroxyl of the molecule. Exemplary linkers may be derived, for example, from dicarboxylic acids such as succinic, glutaric, and butaric acids, or any anhydrides thereof. Additionally, a covalent linker can be attached to etoposide, or derivatives thereof, at the phenol —OH group.

Etoposide derivatives can be described generally by the following formula:

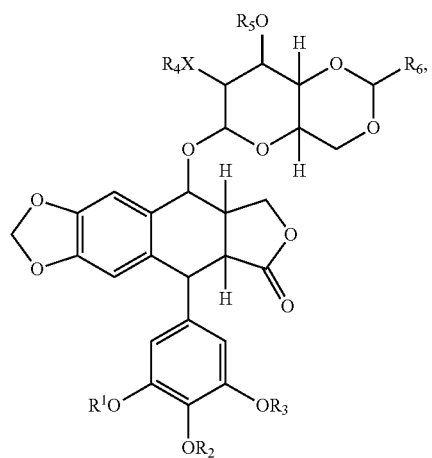

(I-A)

or any stereoisomer thereof, wherein each $R_1$, $R_2$, and $R_3$ is selected, independently, from H, optionally substituted $C_{1-6}$ alkyl, $C(O)R_8$, $P(O)(OR_9)(OR_{10})$, or $S(O)_2(OR_9)$;

X is O or $NR_7$;

each $R_4$, $R_5$, and $R_7$ is selected, independently, from H, optionally substituted $C_{1-6}$ alkyl, or $C(O)R_8$;

$R_6$ is H, optionally substituted $C_{1-6}$ alkyl, optionally substituted aryl, optionally substituted heteroaryl, $R_8$ is selected from optionally substituted $C_{1-6}$ alkyl or optionally substituted aryl; and each $R_9$ and $R_{10}$ is selected, independently, from H, optionally substituted $C_{1-6}$ alkyl, or optionally substituted aryl.

When the compounds of the invention includes an etoposide derivative according to Formula (I), one of $R_1$-$R_6$ includes a hydrolyzable linker Y as described herein. In some embodiments, Y is —C(O)(CH$_2$)$_n$C(O)— and n is 2, 3, or 4. In exemplary, non-limiting embodiments where $R_2$ is C(O)$R_8$, $R_8$ can be $C_{1-6}$ alkyl including an amino substituent and having optional additional substituents. In some embodiments C(O)$R_8$ is a C-linked α-amino acid. The C-linked α-amino acid can be a natural or an unnatural amino acid.

Other exemplary podophyllotoxin derivatives of Formula (I) that can be covalently attached to any of the polypeptides described herein include teniposide and NK611 (Scheme 3).

Scheme 3

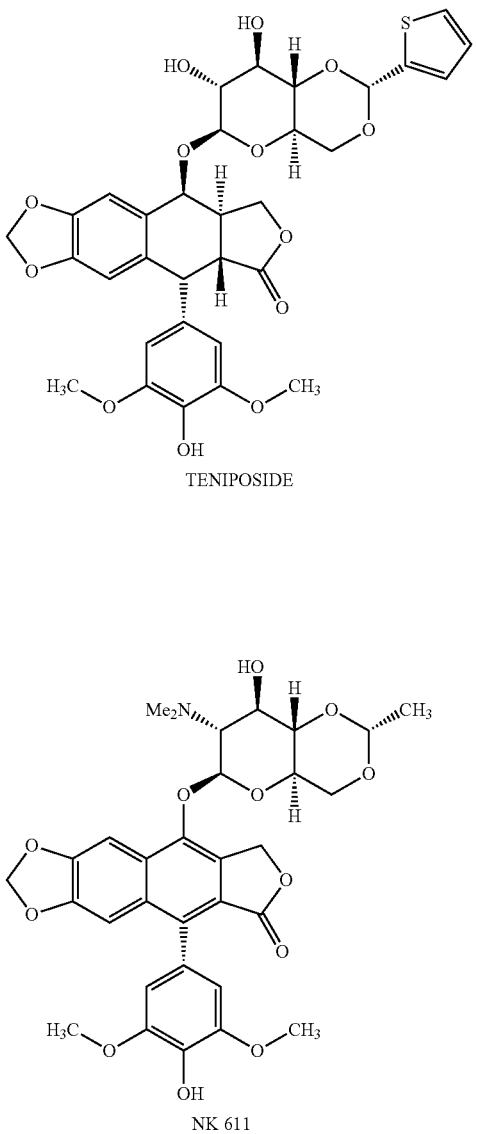

TENIPOSIDE

NK 611

Additional Podophyllotoxin Derivatives

Still other podophyllotoxin derivatives suitable for use in the invention are described in U.S. Pat. Nos. 4,567,253; 4,609,644; 4,900,814; 4,958,010; 5,489,698; 5,536,847; 5,571,914; 6,051,721; 6,107,284; 6,475,486; 6,610,299; 6,878,746; 6,894,075; 7,087,641; 7,176,236; 7,241,595; 7,342,114; and 7,378,419; and in U.S. Patent Publication Nos. 20030064482, 20030162722, 20040044058, 20060148728, and 20070249651, each of which is hereby incorporated by reference.

For example, the etoposide derivatives described in U.S. Pat. No. 7,176,236 can be covalently bonded to an amino acid in any of the polypeptides described herein (e.g., Angiopep-2). Accordingly, in one embodiment, the compounds of the invention include a structure according to Formula (I)

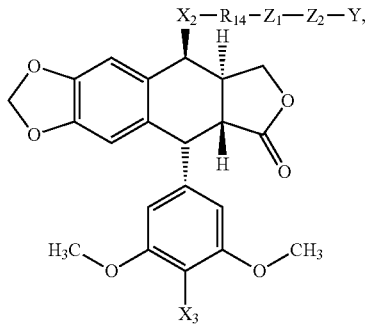

(I-B)

wherein $R_2$ and Y are as described for Formula (I);

$X_2$ is —O—, —S—, —NH—, —CO—, —CH=N—, or —CH$_2$NH—;

$X_3$ is $OR_2$ or $N(R_2)_2$;

$Z_1$ is a covalent bond, —NHCO—, —CONH—, —OCO—, or —COO—;

$Z_2$ is a covalent —(CH$_2$)$_o$R$_{15}$, or —(CH$_2$)$_o$ is incorporated into $Z_2$ as a 5-8 membered ring;

$R_{14}$ is a covalent bond or optionally substituted alkyl, alkenyl, or phenyl; and $R_{15}$ is substituted alkyl, substituted alkenyl, or substituted aryl, wherein the substituted group includes at least one amino group.

In some embodiments, $X_3$ is —OH, —OC(O)CH$_2$NH$_2$, —OC(O)CH$_2$NHCH$_3$, or —OC(O)CH$_2$N(CH$_3$)$_2$. In other embodiments, X is —NH—.

In some embodiments, —R$_{14}$—Z$_1$—Z$_2$— is -(p-C$_6$H$_4$—R$_{16}$)—, where R$_{16}$ is —NO$_2$, —F, —CONHCH$_2$CH$_2$C$_6$H$_5$, or —CONHCH$_2$CH$_2$(p-C$_6$H$_4$OH).

In any compounds of Formulas (I) or (I-A), the group $OR_2$ may be —OC(O)R$_8$.

In some embodiments, the compound of Formula (I), or a pharmaceutically acceptable salt thereof, that is used can allow for improved physicochemical (e.g., solubility properties). For example, when increased solubility is desired, the compound of Formula (I) is preferably Etoposide$_{DMG}$.

Doxorubicin Derivatives

In some embodiments, the anti-cancer agent is doxorubicin (hydroxydaunorubicin or Adriamycin®) or a doxorubicin derivative such as epirubicin (Ellence® or Pharmorubicin®), or a pharmaceutically acceptable salt thereof. The structures of these exemplary compounds are shown in Scheme 4. Doxorubicin and doxorubicin derivatives can be covalently attached to an amino acid in any of the polypeptides described herein through a hydrolyzable covalent linker Y, as defined herein, covalently bonded to, for example, the 14-hydroxyl group.

Scheme 4

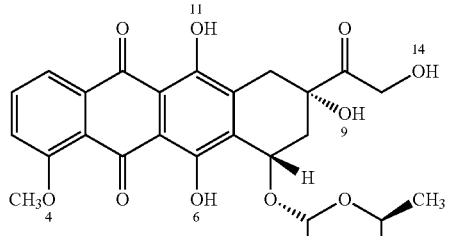

doxorubicin

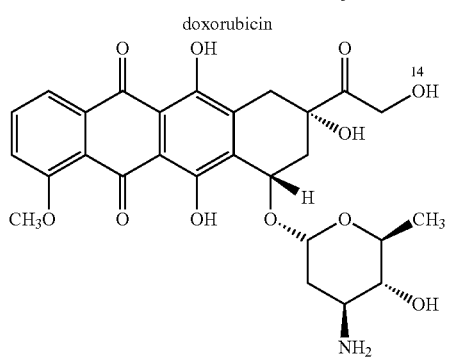

epirubicin

Doxorubicin derivatives can be described generally by the following Formula (II):

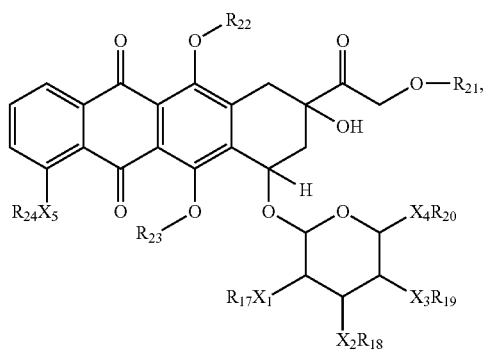

(II)

wherein each $X_1$, $X_2$, $X_3$, $X_4$, and $X_5$ is selected, independently, from a covalent bond, O, or NR$_{25}$;

each $R_{17}$, $R_{18}$, $R_{19}$, $R_{20}$, $R_{20}$, $R_{21}$, $R_{22}$, $R_{23}$, $R_{24}$, and $R_{25}$, is selected, independently, from H, optionally substituted C$_{1-6}$ alkyl, optionally substituted C$_{2-6}$ alkenyl, optionally substituted C$_{2-6}$ alkynyl, optionally substituted cycloalkyl, optionally substituted heterocyclyl, or is a hydrolyzable linker Y as defined herein.

When a compound of Formula (II) is attached to any of the polypeptides described herein, one of R$_{17}$, R$_{18}$, R$_{19}$, R$_{20}$, R$_{20}$, R$_{21}$, R$_{22}$, R$_{23}$, R$_{24}$, and R$_{25}$ is Y. In certain embodiments, R$_{21}$ is Y. Compounds of Formula (II) include compounds having a structure according to Formula (II-A)

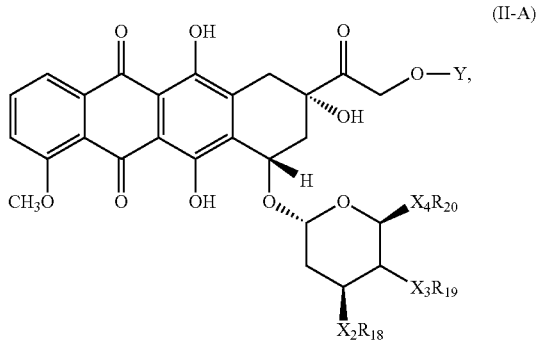

(II-A)

wherein
Y is a hydrolyzable linker as described herein; $X_2R_{18}$ is H or $NH_2$; $X_3R_{19}$ is H or OH; and $X_4R_{20}$ is H or optionally substituted $C_{1-3}$ alkyl. In some embodiments, the hydrolyzable linker Y is —C(O)(CH$_2$)$_n$C(O)— and n is 2, 3, or 4. In certain embodiments, the compound of Formula (II) is:

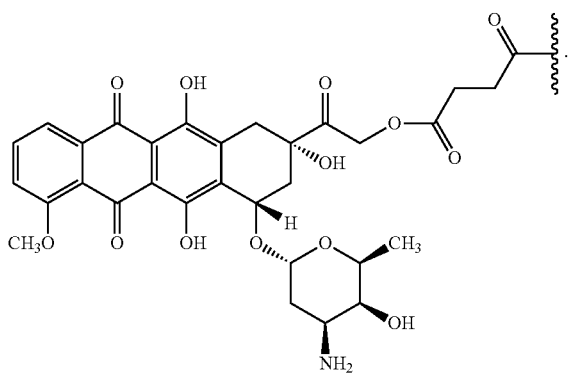

Other doxorubicin derivatives can be found in U.S. Pat. Nos. 4,098,884, 4,301,277, 4,314,054, 4,464,529, 4,585,859, 4,672,057, 4,684,629, 4,826,964, 5,200,513, 5,304,687, 5,594,158, 5,625,043, and 5,874,412, each of which is hereby incorporated by reference.

In some embodiments, the compound of Formula (II), or a pharmaceutically acceptable salt thereof, that is used can allow for improved physicochemical (e.g., solubility properties). For example, when increased solubility is desired, the compound of Formula (II) is preferably the hydrochloride salt of doxorubicin.

In addition to Angiopep-2, podophyllotoxin derivatives such as etoposide, etoposide phosphate, etoposide$_{DMG}$, teniposide, NK611, and other compounds of Formulas (I) and (I-A), or doxorubicin, epirubicin, and other doxorubicin derivatives (e.g., compounds of Formula (II)) can also be conjugated to any of the polypeptides described herein (e.g., Angiopep-4b, Angiopep-5, Angiopep-6, or Angiopep-7). Hydrolysable linkers, such as linkers that include ester groups, can be used to covalently bind the anticancer agent (e.g., podophyllotoxin derivatives or doxorubicin derivatives) to a polypeptide (e.g., Example 1 described herein). Etoposide, etoposide phosphate, etoposide$_{DMG}$, other podophyllotoxin derivatives thereof, doxorubicin, epirubicin, and other doxorubicin derivatives have multiple strategic positions (e.g., the 2" and 3" hydroxyls of etoposide, etoposide phosphate, and etoposide$_{DMG}$, and the 14 hydroxyl of doxorubicin and epirubicin). For example, a difunctional group (e.g., a reagent derived from succinic acid, glutaric acid, glutaric anhydride, or butaric acid, or any anhydrides thereof) can be attached to etoposide at the 2" hydroxyl or to doxorubicin at the 14 hydroxyl. These exemplary intermediates can then be activated with a peptide-coupling reagent such as BTTU and treated with a polypeptide. Other peptide coupling agents include carbodiimides (e.g., dicyclohexylcarbodiimide (DCC), diisopropylcarbodiimide (DIC), and 1-Ethyl-3-(3-dimethylaminopropyl)carbodiimide hydrochloride) (EDC-HCl)), triazoles (e.g., 1-hydroxy-benzotriazole (HOBt) and 1-hydroxy-7-aza-benzotriazole (HOAt)), related benzotriazole peptide coupling agents such as O-Benzotriazole-N,N,N',N'-tetramethyl-uronium-hexafluoro-phosphate (HBTU), 2-(6-Chloro-1H-benzotriazole-1-yl)-1,1,3,3-tetramethylaminium hexafluorophosphate (HCTU), 2-(1H-9-Azobenzotriazole-1-yl)-1,1,3,3-tetramethylaminium hexafluorophosphate (HATU), Benzotriazole-1-yl-oxy-tris-(dimethylamino)-phosphonium hexafluorophosphate (BOP reagent), and benzotriazol-1-yl-oxytripyrrolidinophosphonium hexafluorophosphate (PyBOP), and 3-(Diethoxyphosphoryloxy)-1,2,3-benzotriazin-4(3H)-one (DEPBT). The conjugate can then be purified. Each intermediate or product of this synthetic procedure is purified and validated using different approaches such as HPLC, thin liquid chromatography, NMR ($^{13}$C or $^1$H exchange), melting point, mass spectrometry. The final conjugate is analyzed by mass spectrometry and SDS-polyacrylamide gel electrophoresis. This allows the determination of the number of molecules (e.g., of etoposide, etoposide phosphate, etoposide$_{DMG}$, doxorubicin, or epirubicin) conjugated to each vector.

Hydrolyzable Linkers

When a compound of Formula (I) is covalently attached by a hydrolyzable linker Y to an amino acid in a polypeptide, the linker can be located at $R_1$, $R_2$, $R_3$, $R_4$, $R_5$, or $R_7$. Similarly, when a compound of Formula (II) is covalently attached by a hydrolyzable linker Y to an amino acid in a polypeptide, the linker can be located at any of $R_{17}$, $R_{18}$, $R_{19}$, $R_{20}$, $R_{20}$, $R_{21}$, $R_{22}$, $R_{23}$, $R_{24}$, and $R_{25}$. Exemplary, non-limiting hydrolyzable linkers may be prepared from dicarboxylic acids, dicarbonates, carboxylic anhydrides, diisocyanates, or diphosphonic acids. A compound that includes a compound of Formula (I) or (II) that is covalently attached to an amino acid in any of the amino acid sequences described herein may also be described by the following formula

D-G-X-G'-A  (III), where each G and G' is a group selected, independently, from —C(O)—, —C(O)O—, —OC(O)—, —S(O)$_2$O—, —OS(O)$_2$—, —S(O)$_2$NH—, —NHS(O)$_2$—, and —OP(O)(OR$_{11}$)O—;

G is covalently bonded to D, where D is a podophyllotoxin derivative (e.g., a compound of Formula (I)) or doxorubicin or a doxorubicin derivative (e.g., a compound of Formula (II));

G' is covalently bonded to A, where A is an amino acid in an amino acid sequence described herein (e.g., the amino acid sequences described in Table 1, or functional derivatives thereof); and X is -(optionally substituted aryl)-, —(CR$_{12}$R$_{13}$)$_n$—, —O{(CR$_{12}$R$_{13}$)$_2$O}$_n$—, —{(CR$_{12}$R$_{13}$)$_2$O(CR$_{12}$R$_{13}$)$_2$}$_n$—, or —(CR$_{12}$R$_{13}$)$_o$Y(CR$_{12}$R$_{13}$)$_p$—, where each n, o, and p is, independently, an integer between 1-10;

$R_{11}$ is H or lower $C_{1-6}$ alkyl;

$R_{12}$ and $R_{13}$ are each selected, independently, from H, OH, or lower $C_{1-6}$ alkyl; and Y is O, NH, N (lower $C_{1-6}$ alkyl), or -optionally substituted aryl.

Each n, o, and p may be, independently, 1, 2, 3, 4, 5, 6, 7, 8, 9, or 10.

In some embodiments, the G-X-G' moiety in Formula (III) is selected from —C(O)CH$_2$C(O)—, —C(O)(CH$_2$)$_2$C(O)—, —C(O)(CH$_2$)$_3$C(O)—, —C(O)(CH$_2$)$_4$C(O)—, —C(O)(CH$_2$)$_5$C(O)—, —C(O)(CH$_2$)$_6$C(O)—, —C(O)(OCH$_2$CH$_2$)OC(O)—, —C(O)(OCH$_2$CH$_2$)$_2$OC(O)—, —C(O)(OCH$_2$CH$_2$)$_3$OC(O)—, and —C(O)(OCH$_2$CH$_2$)$_4$OC(O)—.

Polypeptides

Exemplary amino acid sequences useful in the compounds of the invention include, but are not limited to, the amino acid sequences described in Table 1.

In addition to the amino acid sequences described in Table 1, the invention also features fragments of these amino acid sequences (e.g., a functional fragment). In certain embodiments, the fragments are capable of entering or accumulating in a particular cell type (e.g., ovary, liver, lung, kidney, spleen, or muscle) or capable of crossing the BBB. Truncations of the polypeptide may be 1, 2, 3, 4, 5, 6, 7, 8, 9, 10, 11, 12, or more amino acids from either the N-terminus of the polypeptide, the C-terminus of the polypeptide, or a combination thereof. Other fragments include sequences where internal portions of the polypeptide are deleted.

Additional polypeptides of the invention may be identified by using one of the assays or methods described in U.S. Patent Application Publication No. 2006/0189515, which is hereby incorporated by reference, or by any method known in the art. For example, a candidate vector may be produced by conventional polypeptide synthesis and conjugated with, for example, a compound of Formulas (I) or (II), and administered to a laboratory animal. A biologically active vector may be identified, for example, based on its efficacy to increase survival of an animal injected with tumor cells and treated with the conjugate as compared to a control which has not been treated with a conjugate (e.g., treated with the unconjugated agent).

In another example, a biologically active polypeptide of the invention may be identified based on its location in the parenchyma in an in situ cerebral perfusion assay. In vitro BBB assays, such as the model developed by CELLIAL™ Technologies, may be used to identify such vectors.

Assays to determine accumulation in other tissues may be performed as well and exemplary assays are described herein. Labeled polypeptides of the invention can be administered to an animal, and accumulation in different organs can be measured. For example, a polypeptide conjugated to a detectable label (e.g., a near-IR fluorescence spectroscopy label such as Cy5.5) allows live in vivo visualization. Such a polypeptide can be administered to an animal, and the presence of the polypeptide in an organ can be detected, thus allowing determination of the rate and amount of accumulation of the polypeptide in the desired organ. In other embodiments, the polypeptide of the invention can be labeled with a radioactive isotope (e.g., $^{125}$I). The polypeptide is then administered to an animal. After a period of time, the animal is sacrificed, and the animal's organs are extracted. The amount of radioisotope in each organ can then measured using any means known in the art. By comparing the amount of a labeled candidate polypeptide in a particular organ without amount of labeled control, the ability of the candidate polypeptide the rate or amount of accumulation of a candidate polypeptide in a particular tissue can be ascertained. Appropriate negative controls include any polypeptide known not be transported into a particular cell type.

For example, the amine groups of Angiopep-1 (SEQ ID NO:67) and Angiopep-2 (SEQ ID NO:97) can be used as sites for conjugation of agents. To study the role of amine groups in conjugation and their impact in the overall transport capacity of these vectors, other vectors have been developed based on the Angiopep-1 and Angiopep-2 sequence. These vectors variable reactive amine groups and variable overall charge. These polypeptides are shown in Table 2.

TABLE 2

| Vectors with variable amine group targets | | | | |
|---|---|---|---|---|
| Polypeptide Name | Polypeptide Sequences | Reactive amines (positions) | Charge | SEQ ID No. |
| Angiopep-3* | Ac$^1$-TFFYGGSRGKRNNFKTEEY | 2 (10, 15) | +1 | 107 |
| Angiopep-4b | RFFYGGSRGKRNNFKTEEY | 3 (1, 10, 15) | +3 | 108 |
| Angiopep-4a | Ac$^1$-RFFYGGSRGKRNNFKTEEY | 2 (10, 15) | +2 | 109 |
| Angiopep-5 | Ac$^1$-RFFYGGSRGKRNNFRTEEY | 1 (10) | +2 | 110 |
| Angiopep-6 | TFFYGGSRGKRNNFRTEEY | 2 (1, 10) | +2 | 111 |
| Angiopep-7 | TFFYGGSRGRRNNFRTEEY | 1 (1) | +2 | 112 |

*Angiopep-3 is an acetylated form of Angiopep-2.
$^1$Ac represents acetylation.

Modified Polypeptides

The invention can also include polypeptides having a modification of an amino acid sequence described herein (e.g., polypeptide having a sequence described in any one of SEQ ID NOS:1-105 and 107-116 such as AngioPep-3, -4a, -4b, -5, -6, or -7) and in which the polypeptide includes an amino acid that is covalently bonded to a compound of Formulas (I) or (II). In certain embodiments, the modification does not destroy significantly a desired biological activity. In some embodiments, the modification may cause a reduction in biological activity (e.g., by at least 5%, 10%, 20%, 25%, 35%, 50%, 60%, 70%, 75%, 80%, 90%, or 95%). In other embodiments, the modification has no effect on the biological activity or may increase (e.g., by at least 5%, 10%, 25%, 50%, 100%, 200%, 500%, or 1000%) the biological activity of the original polypeptide. The modified polypeptide may have or may optimize one or more of the characteristics of a polypeptide of the invention which, in some instance might be needed or desirable. Such characteristics include in vivo stability, bioavailability, toxicity, immunological activity, or immunological identity.

Polypeptides of the invention may include amino acids or sequences modified either by natural processes, such as post-translational processing, or by chemical modification techniques known in the art. Modifications may occur anywhere in a polypeptide including the polypeptide backbone, the amino acid side-chains and the amino- or carboxy-terminus. The same type of modification may be present in the same or varying degrees at several sites in a given polypeptide, and a polypeptide may contain more than one type of modification. Polypeptides may be branched as a result of ubiquitination, and they may be cyclic, with or without branching. Cyclic, branched, and branched cyclic polypeptides may result from posttranslational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to flavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide of the invention may further include an amino acid insertion, deletion, or substitution, either conservative or non-conservative (e.g., D-amino acids, desamino acids) in the polypeptide sequence (e.g., where such changes do not substantially alter the biological activity of the polypeptide).

For example, in some embodiments, the amino acid sequence (e.g., SEQ ID NOS 1-105 or 107-116) is modified by inserting one or more additional cysteine residues at the N-terminal of the peptide, the C-terminal of the peptide, or both. The addition of one or more cysteine residues to the amino or carboxy terminus of any of the amino acid sequences described herein can facilitate conjugation of these polypeptides to nucleic acids (e.g., siRNA molecules) or lipid vectors by, e.g., disulfide bonding. For example, Angiopep-1 (SEQ ID NO:67), Angiopep-2 (SEQ ID NO:97), or Angiopep-7 (SEQ ID NO:112) can be modified to include a single cysteine residue at the amino-terminus (SEQ ID NOS: 71, 113, and 115, respectively) or a single cysteine residue a the carboxy-terminus (SEQ ID NOS: 72, 114, and 116, respectively).

Substitutions may be conservative (i.e., wherein a residue is replaced by another of the same general type or group) or non-conservative (i.e., wherein a residue is replaced by an amino acid of another type). In addition, a non-naturally occurring amino acid may be substituted for a naturally occurring amino acid (i.e., non-naturally occurring conservative amino acid substitution or a non-naturally occurring non-conservative amino acid substitution).

Polypeptides made synthetically may include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogues may be generated by substitutional mutagenesis and retain the biological activity of the original polypeptide. Examples of substitutions identified as "conservative substitutions" are shown in Table 3. If such substitutions result in a change not desired, then other type of substitutions, denominated "exemplary substitutions" in Table 3, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe), (2) neutral hydrophilic: Cysteine (Cys), Serine (Ser), Threonine (Thr)

(3) acidic/negatively charged: Aspartic acid (Asp), Glutamic acid (Glu)

(4) basic: Asparagine (Asn), Glutamine (Gln), Histidine (His), Lysine (Lys), Arginine (Arg)

(5) residues that influence chain orientation: Glycine (Gly), Proline (Pro);

(6) aromatic: Tryptophan (Trp), Tyrosine (Tyr), Phenylalanine (Phe), Histidine (His), (7) polar: Ser, Thr, Asn, Gln (8) basic positively charged: Arg, Lys, His, and;

(9) charged: Asp, Glu, Arg, Lys, His

Other conservative amino acid substitutions are listed in Table 3.

TABLE 3

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Additional Polypeptide Analogues

The compounds of the invention may include polypeptide analogs of aprotinin known in the art where the analogs include an amino acid that is covalently bonded to a podophyllotoxin derivative (e.g., a compound of Formula (I)) or to doxorubicin or a doxorubicin derivative (e.g., a compound of Formula (II)). For example, U.S. Pat. No. 5,807,980 describes Bovine Pancreatic Trypsin Inhibitor (aprotinin)-derived inhibitors as well as a method for their preparation and therapeutic use, including the polypeptide of SEQ ID NO:102. These polypeptides have been used for the treatment of a condition characterized by an abnormal appearance or amount of tissue factor and/or factor VIIIa such as abnormal thrombosis. U.S. Pat. No. 5,780,265 describes serine protease inhibitors capable of inhibiting plasma kallikrein, including SEQ ID NO:103. U.S. Pat. No. 5,118,668 describes Bovine Pancreatic Trypsin Inhibitor variants, including SEQ ID NO:105. The aprotinin amino acid sequence (SEQ ID NO:98), the Angiopep-1 amino acid sequence (SEQ ID NO:67), and SEQ ID NO:104, as well as some sequences of biologically active analogs may be found in International Application Publication No. WO 2004/060403.

An exemplary nucleotide sequence encoding an aprotinin analogue is illustrated in SEQ ID NO:106 (atgagaccag atttctgcct cgagccgccg tacactgggc cctgcaaagc tcgtatcatc cgttacttct acaatgcaaa ggcaggcctg tgtcagacct tcgtatacgg cggctgcaga gctaagcgta acaacttcaa atccgcggaa gactgcatgc gtacttgcgg tggtgcttag; Genbank accession No. X04666). This sequence encodes a lysine at position 16 instead of a valine, as found in SEQ ID NO:98. A mutation in the nucleotide sequence of SEQ ID NO:106 may be introduced by methods known in the art to change the produce the polypeptide of SEQ ID NO:98 having a valine in position 16. Additional mutations or fragments may be obtained using any technique known in the art.

Other examples of aprotinin analogs may be found by performing a protein BLAST (Genebank: www.ncbi.nlm.nih.gov/BLAST/) using the synthetic aprotinin sequence (or portion thereof) disclosed in International Application No. PCT/CA2004/000011. Exemplary aprotinin analogs are found under accession Nos. CAA37967 (GI:58005) and 1405218C (GI:3604747).

Preparation of Polypeptide Derivatives and Peptidomimetics

In addition to polypeptides consisting only of naturally occurring amino acids, peptidomimetics or polypeptide analogs are also encompassed by the present invention. Polypeptide analogs are commonly used in the pharmaceutical industry as non-polypeptide drugs with properties analogous to those of the template polypeptide. The non-polypeptide compounds are termed "polypeptide mimetics" or peptidomimetics (Fauchere et al., *Infect. Immun.* 54:283-287, 1986; Evans et al., *J. Med. Chem.* 30:1229-1239, 1987). Polypeptide mimetics that are structurally related to therapeutically useful polypeptides may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —CH$_2$NH—, —CH$_2$S—, —CH$_2$—CH$_2$—, —CH=CH— (cis and trans), —CH$_2$SO—, —CH(OH)CH$_2$—, —COCH$_2$— etc., by methods well known in the art (Spatola, *Peptide Backbone Modifications, Vega Data*, 1(3):267, 1983); Spatola et al. (*Life Sci.* 38:1243-1249, 1986); Hudson et al. (*Int. J. Pept. Res.* 14:177-185, 1979); and Weinstein. B., 1983, Chemistry and Biochemistry, of Amino Acids, Peptides and Proteins, Weinstein eds, Marcel Dekker, New York). Such polypeptide mimetics may have significant advantages over naturally-occurring polypeptides including more economical production, greater chemical stability, enhanced pharmacological properties (e.g., half-life, absorption, potency, efficiency), reduced antigenicity and others.

While the polypeptides of the invention may be effective in entering particular cell types (e.g., those described herein), their effectiveness may be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the polypeptide and require a free N-terminus (Powell et al., *Pharm. Res.* 10:1268-1273, 1993). In light of this, it is often advantageous to use modified versions of polypeptides. The modified polypeptides retain the structural characteristics of the original L-amino acid polypeptides that confer biological activity with regard to IGF-1, but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable polypeptides. Thus, a polypeptide derivative or peptidomimetic of the present invention may be all L, all D or mixed D, L polypeptide. The presence of an N-terminal or C-terminal D-amino acid increases the in vivo stability of a polypeptide because peptidases cannot utilize a D-amino acid as a substrate (Powell et al., *Pharm. Res.* 10:1268-1273, 1993). Reverse-D polypeptides are polypeptides containing D-amino acids, arranged in a reverse sequence relative to a polypeptide containing L-amino acids. Thus, the C-terminal residue of an L-amino acid polypeptide becomes N-terminal for the D-amino acid polypeptide, and so forth. Reverse D-polypeptides retain the same tertiary conformation and therefore the same activity, as the L-amino acid polypeptides, but are more stable to enzymatic degradation in vitro and in vivo, and thus have greater therapeutic efficacy than the original polypeptide (Brady and Dodson, *Nature* 368:692-693, 1994; Jameson et al., *Nature* 368:744-746, 1994). In addition to reverse-D-polypeptides, constrained polypeptides comprising a consensus sequence or a substantially identical consensus sequence variation may be generated by methods well known in the art (Rizo and Gierasch, *Ann. Rev. Biochem.* 61:387-418, 1992). For example, constrained polypeptides may be generated by adding cysteine residues capable of forming disulfide bridges and, thereby, resulting in a cyclic polypeptide. Cyclic polypeptides have no free N- or C-termini. Accordingly, they are not susceptible to proteolysis by exopeptidases, although they are, of course, susceptible to endopeptidases, which do not cleave at peptide termini. The amino acid sequences of the polypeptides with N-terminal or C-terminal D-amino acids and of the cyclic polypeptides are usually identical to the sequences of the polypeptides to which they correspond, except for the presence of N-terminal or C-terminal D-amino acid residue, or their circular structure, respectively.

A cyclic derivative containing an intramolecular disulfide bond may be prepared by conventional solid phase synthesis while incorporating suitable S-protected cysteine or homocysteine residues at the positions selected for cyclization such as the amino and carboxy termini (Sah et al., *J. Pharm. Pharmacol.* 48:197, 1996). Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure or (2) by removal of the polypeptide from the support along with complete side chain de-protection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S-alkyl bonds can be prepared by conventional solid phase chemistry while incorporating an amino acid residue with a suitable amino-protected side chain, and a suitable S-protected cysteine or homocysteine residue at the position selected for cyclization.

Another effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al., *Pharm. Res.* 10:1268-1273, 1993). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified polypeptides consisting of polypeptides bearing an N-terminal acetyl group and/or a C-terminal amide group.

Also included by the present invention are other types of polypeptide derivatives containing additional chemical moieties not normally part of the polypeptide, provided that the derivative retains the desired functional activity of the polypeptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives.

Longer polypeptide sequences which result from the addition of additional amino acid residues to the polypeptides of the invention are also encompassed in the present invention. Such longer polypeptide sequences would be expected to have the same biological activity (e.g., entering particular cell types) as the polypeptides described above. While polypeptides having a substantial number of additional amino acids are not excluded, it is recognized that some large polypeptides may assume a configuration that masks the effective sequence, thereby preventing binding to a target (e.g., a member of the LRP receptor family such as LRP or LRP2). These derivatives could act as competitive antagonists. Thus, while the present invention encompasses polypeptides or derivatives of the polypeptides described herein having an extension, desirably the extension does not destroy the cell targeting activity of the polypeptide or derivative.

Other derivatives included in the present invention are dual polypeptides consisting of two of the same, or two different polypeptides of the present invention covalently linked to one another either directly or through a spacer, such as by a short stretch of alanine residues or by a putative site for proteolysis (e.g., by cathepsin, see e.g., U.S. Pat. No. 5,126,249 and European Patent No. 495 049). Multimers of the polypeptides of the present invention consist of polymer of molecules formed from the same or different polypeptides or derivatives thereof.

The present invention also features polypeptide derivatives that are chimeric or fusion proteins containing a polypeptide described herein, or fragment thereof, linked at its amino- or carboxy-terminal end, or both, to an amino acid sequence of a different protein. Such a chimeric or fusion protein may be produced by recombinant expression of a nucleic acid encoding the protein. For example, a chimeric or fusion protein may contain at least 6 amino acids of a polypeptide of the present invention and desirably has a functional activity equivalent or greater than a polypeptide of the invention.

Polypeptide derivatives of the present invention can be made by altering the amino acid sequences by substitution, addition, or deletion or an amino acid residue to provide a functionally equivalent molecule, or functionally enhanced or diminished molecule, as desired. The derivative of the present invention include, but are not limited to, those containing, as primary amino acid sequence, all or part of the amino acid sequence of the polypeptides described herein (e.g., any one of SEQ ID NOS:1-105 and 107-112) including altered sequences containing substitutions of functionally equivalent amino acid residues. For example, one or more amino acid residues within the sequence can be substituted by another amino acid of a similar polarity that acts as a functional equivalent, resulting in a silent alteration. Substitution for an amino acid within the sequence may be selected from other members of the class to which the amino acid belongs. For example, the positively charged (basic) amino acids include, arginine, lysine and histidine. The nonpolar (hydrophobic) amino acids include, leucine, isoleucine, alanine, phenylalanine, valine, proline, tryptophan and methionine. The uncharged polar amino acids include serine, threonine, cysteine, tyrosine, asparagine and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions.

Assays to Identify Peptidomimetics

As described above, non-peptidyl compounds generated to replicate the backbone geometry and pharmacophore display (peptidomimetics) of the polypeptides identified by the methods of the present invention often possess attributes of greater metabolic stability, higher potency, longer duration of action and better bioavailability.

The peptidomimetics compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, *Anticancer Drug Des.* 12:145, 1997). Examples of methods for the synthesis of molecular libraries can be found in the art, for example, in: DeWitt et al. (*Proc. Natl. Acad. Sci. USA* 90:6909, 1993); Erb et al. (*Proc. Natl. Acad. Set USA* 91:11422, 1994); Zuckermann et al., *J. Med. Chem.* 37:2678, 1994); Cho et al. (*Science* 261:1303, 1993); Carell et al. (*Angew. Chem., Int. Ed. Engl.* 33:2059, 1994 and ibid 2061); and in Gallop et al. (*Med. Chem.* 37:1233, 1994). Libraries of compounds may be presented in solution (e.g., Houghten, *Biotechniques* 13:412-421, 1992) or on beads (Lam, *Nature* 354:82-84, 1991), chips (Fodor, *Nature* 364:555-556, 1993), bacteria or spores (U.S. Pat. No. 5,223,409), plasmids (Cull et al., *Proc. Natl. Acad. Sci. USA* 89:1865-1869, 1992) or on phage (Scott and Smith, *Science* 249:386-390, 1990), or luciferase, and the enzymatic label detected by determination of conversion of an appropriate substrate to product.

Once a polypeptide of the present invention is identified, it may be isolated and purified by any number of standard methods including, but not limited to, differential solubility (e.g., precipitation), centrifugation, chromatography (e.g., affinity, ion exchange, size exclusion, and the like) or by any other standard techniques used for the purification of polypeptides, peptidomimetics or proteins. The functional properties of an identified polypeptide of interest may be evaluated using any functional assay known in the art. Desirably, assays for evaluating downstream receptor function in intracellular signaling are used (e.g., cell proliferation).

For example, the peptidomimetics compounds of the present invention may be obtained using the following three-phase process: (1) scanning the polypeptides of the present invention to identify regions of secondary structure necessary for targeting the particular cell types described herein; (2) using conformationally constrained dipeptide surrogates to refine the backbone geometry and provide organic platforms corresponding to these surrogates; and (3) using the best organic platforms to display organic pharmacophores in libraries of candidates designed to mimic the desired activity of the native polypeptide. In more detail the three phases are as follows. In phase 1, the lead candidate polypeptides are scanned and their structure abridged to identify the requirements for their activity. A series of polypeptide analogs of the original are synthesized. In phase 2, the best polypeptide analogs are investigated using the conformationally constrained dipeptide surrogates. Indolizidin-2-one, indolizidin-9-one and quinolizidinone amino acids ($I^2$aa, $I^9$aa and Qaa respectively) are used as platforms for studying backbone geometry of the best polypeptide candidates. These and related platforms (reviewed in Halab et al., *Biopolymers* 55:101-122, 2000; and Hanessian et al. *Tetrahedron* 53:12789-12854, 1997) may be introduced at specific regions of the polypeptide to orient the pharmacophores in different directions. Biological evaluation of these analogs identifies improved lead polypeptides that mimic the geometric requirements for activity. In phase 3, the platforms from the most active lead polypeptides are used to display organic surrogates of the pharmacophores responsible for activity of the native polypeptide. The pharmacophores and scaffolds are combined in a parallel synthesis format. Derivation of polypeptides and the above phases can be accomplished by other means using methods known in the art.

Structure function relationships determined from the polypeptides, polypeptide derivatives, peptidomimetics or other small molecules of the present invention may be used to refine and prepare analogous molecular structures having similar or better properties. Accordingly, the compounds of the present invention also include molecules that share the structure, polarity, charge characteristics and side chain properties of the polypeptides described herein.

In summary, based on the disclosure herein, those skilled in the art can develop polypeptides and peptidomimetics screening assays which are useful for identifying compounds for targeting an agent to particular cell types (e.g., those described herein). The assays of this invention may be developed for low-throughput, high-throughput, or ultra-high throughput screening formats. Assays of the present invention include assays that are amenable to automation.

Polypeptide Conjugates Covalently Bonded to Additional Agents

The compounds described herein, or functional derivatives thereof, in addition to including an amino acid sequence that is covalently bonded through an amino acid to a podophyllotoxin derivative (e.g., a compound having a structure according to Formula (I)) or to doxorubicin or a doxorubicin derivative (e.g., a compound of Formula (II)), may also include a covalent bond to another agent (e.g., another therapeutic agent, a diagnostic agent, or to a label). In certain embodiments, the amino acid sequence is also linked to or labeled with a detectable label, such as a radioimaging agent, for diagnosis of a disease or condition. Examples of these agents include a radioimaging agent-antibody-vector conjugate, where the antibody binds to a disease or condition-specific antigen (e.g., for diagnosis or therapy). Other binding molecules are also contemplated by the invention. In other cases, the compound of the invention, or a functional derivative thereof, is linked to another therapeutic agent, to treat a disease or condition, or may be linked to or labeled with mixtures thereof. The disease or condition may be treated by administering a vector-agent conjugate to an individual under conditions which allow transport of the agent across the BBB or into a particular cell type. Each polypeptide may include at least 1, 2, 3, 4, 5, 6, or 7 additional agents. In other embodiments, each agent has at least 1, 2, 3, 4, 5, 6 7, 10, 15, 20, or more polypeptides attached thereto. The conjugates of the invention may be able to promote accumulation (e.g., due to increased uptake or reduced removal) of the agent in a particular cell type or tissue such as the brain, ovary, liver, lung, kidney, spleen or muscle of a subject.

An agent (e.g., a podophyllotoxin derivative such as a compound of Formula (I) or doxorubicin or a doxorubicin derivative (e.g., a compound of Formula (II)), another therapeutic agent, a diagnostic agent, or a label) that has a covalent bond to an amino acid in any of the amino acid sequences described herein (e.g., those listed in Table 1, or functional derivatives thereof) may be releasable from the vector after transport into a particular cell type or across the BBB. The agent can be released, for example, by enzymatic cleavage or other breakage of a chemical bond between the vector and the agent. The released agent may then function in its intended capacity in the absence of the vector.

Other methods and cross-linkers can be used to conjoin the polypeptides and RNAi agents of the invention. For example, a 5' or 3' thiol-containing siRNA sense strand can be linked by a disulfide bond to a cysteine residue placed at either the amino or carboxy terminus of the polypeptide. Muratovska et al. (*FEBS Letters* 558:63-68, 2004) and Turner et al. (*Blood Cells, Molecules, and Diseases* 38:1-7, 2007) provide exemplary chemical bonding methods for conjugating polypeptides to RNA molecules and are hereby incorporated by reference.

Therapeutic Agents

A therapeutic agent may be any biologically active agent. For example, a therapeutic may be a drug, a medicine, an agent emitting radiation, a cellular toxin (for example, a chemotherapeutic agent), a biologically active fragment thereof, or a mixture thereof to treat a disease (e.g., to killing cancer cells) or it may be an agent to treat a disease or condition in an individual.

Podophyllotoxin derivatives (e.g., the compounds of Formula (I)) and doxorubicin and doxorubicin derivatives (e.g., compounds of Formula (II)) are exemplary useful classes of therapeutic agents. A therapeutic agent may be a synthetic product or a product of fungal, bacterial or other microorganism (e.g., mycoplasma or virus), animal, such as reptile, or plant origin. A therapeutic agent and/or biologically active fragment thereof may be an enzymatically active agent and/or fragment thereof, or may act by inhibiting or blocking an important and/or essential cellular pathway or by competing with an important and/or essential naturally occurring cellular component. Other therapeutic agents include antibodies and antibody fragments.

Any anticancer agent known in the art may be part of a conjugate of the invention. Podophyllotoxin derivatives (e.g., the compounds of Formula (I)) and doxorubicin and doxorubicin derivatives (e.g., compounds of Formula (II)) can be anticancer agents. Additional anticancer agents may also be conjugated to the compounds of the invention as described herein. Cancers of the brain may be treated with a conjugate containing a vector that is efficiently transported across the BBB (e.g., AngioPep-2, AngioPep-3, AngioPep-4a, AngioPep-4b, AngioPep-5, or AngioPep-6). Ovary, liver, lung, kidney, or spleen cancers may be treated with an anticancer agent conjugated to a vector that is transported efficiently into the appropriate cell type (e.g., AngioPep-7).

Conjugate Activities

Compounds, or a pharmaceutically acceptable salt thereof, that include an amino acid sequence, where the amino acid sequence is covalently bonded through an amino acid to a podophyllotoxin derivative (e.g., a compound having a structure according to Formula (I)) or to doxorubicin or doxorubicin derivatives (e.g., compounds of Formula (II)) can achieve desirable properties, such as altered pharmacokinetics or altered tissue distribution (e.g., increased delivery to particular tissues or cell types such as ovary, liver, brain, lung, spleen, or kidney) relative to the unconjugated biologically active agent. Accordingly, the compounds of the invention can be used as vectors. Polypeptides such as AngioPep-3, AngioPep-4a, AngioPep-4b, AngioPep-5, and AngioPep-6 efficiently transport agents across the BBB. Like AngioPep-2, these polypeptides may also be capable of targeting agents to other cell types or tissues (e.g., ovary, liver, lung, kidney, spleen, or muscle). The AngioPep-7 polypeptide, which is not efficiently transported across the BBB, is transported to particular tissues (e.g., ovary, liver, lung, kidney, spleen, or muscle). This activity may be useful where transport across the BBB is not desired. For example, the use of a compound of the invention can increase the concentration of the therapeutic agent in the target tissue by anywhere from 10%-20,000% relative to that observed with the unconjugated biologically active agent (for example, etoposide, etoposide phosphate, etoposide$_{DMG}$, teniposide, doxorubicin, or epirubicin).

Because the compounds of the invention can transport agents to specific tissues, conjugated agents may result in lower toxicity (e.g., fewer side effects), higher efficacy (e.g., because the agent is concentrated into a target tissue due to increased uptake or decreased efflux from the tissue or because the agent has greater stability when conjugated), or a combination thereof. Such activities are described below and in International Publication No. WO 2007/009229, hereby incorporated by reference.

In some cases, conjugation of an agent to a vector allows the agent to escape the action of P-glycoprotein (P-gp), an efflux pump capable of expelling certain agents from a cell. By decreasing the ability of P-gp to expel an agent from a cell, the potency of that agent in a cell can be increased. These conjugates can thus actively inhibit cancer cell proliferation. Moreover, results obtained for in vivo tumor growth indicate that the vectors of the invention may target the receptor LRP. Also, conjugation may modify the pharmacokinetics or biodistribution of the unconjugated agent.

Taken together, conjugates can be used against primary tumors including ovary, breast, lung, and skin cancers as well as metastasis originating from primary tumors.

Methods of Treatment

The invention also features methods of treatment using the compounds of the invention, or pharmaceutical compositions thereof, described herein. The compounds of the invention (e.g., compounds that include an amino acid sequence that is covalently bonded through an amino acid to a podophyllotoxin derivative such as a compound of Formula (I) or to doxorubicin or doxorubicin derivatives (e.g., compounds of Formula (II)) that are efficiently transported across the BBB (e.g., AngioPep-2, AngioPep-3, AngioPep-4a, AngioPep-4b, AngioPep-5, and AngioPep-6) may be used to treat any brain or central nervous system disease. Exemplary neurological diseases include, but are not limited to, brain cancers such as a brain tumor, a spinal cord tumor (e.g., chordoma), and a brain metastasis Brain tumors may be primary metastatic brain tumors. Brain tumors that originate in the brain are primary brain tumors. Brain tumors caused by the spread of cancer elsewhere in the body (e.g., lung, breast, melanoma, colon, kidney, and other cancers) are metastatic brain tumors. Exemplary categories of tumors, as described by their location in the brain, include brain stem tumors, cerebellopontine angle tumors (e.g., acoustic nerve tumors), cerebral hemisphere tumors, frontal lobe tumors, parietal lobe tumors, pineal region tumors, occipital lobe tumors, temporal lobe tumors, subcortical tumors, meningeal brain tumors, midline tumors (e.g., craniopharyngioma, optic nerve glioma, and tumors of the thalamus and sellar areas), posterior fossa tumors (e.g., tumors of the fourth ventricle, andcerebellar tumors).

Exemplary brain tumors include acoustic neuroma (neurilemmoma, schwannoma, neurinoma), adenoma, astrocytoma (e.g., juvenile pilocytic astrocytomas, subependymal giant cell astrocytomas, gemistocytic astrocytoma, anaplastic astrocytoma, malignant astrocytoma, glioblastoma multiforme, and gliosarcoma), brain stem glioma which may be anastrocytoma, anaplastic astrocytoma, glioblastoma multiforme, or a mixed tumor, choroid plexus papilloma, cns lymphoma, ependymoma (e.g., anaplastic ependymoma), gangliocytoma, ganglioglioma, glioma, glioblastoma multiforme, medulloblastoma (mdl), anaplastic (malignant) meningioma, mixed glioma, neurofibromatosis (von Recklinghausen's Disease), oligodendroglioma, and optic nerve glioma (e.g., pilocytic astrocytoma).

Conjugates can also be efficiently transported to the liver, ovary, lung, kidney, spleen or muscle and therefore may also be used, in conjunction with an appropriate therapeutic agent, to treat a disease associated with these tissues (e.g., a cancer). Because AngioPep-7 is not efficiently transported to the brain, but is transported efficiently to tissues and cells such as liver, lung, kidney, spleen and muscle, compounds of the invention that include AngioPep-7 may be especially well suited as a vector treatment of diseases associated with these tissues when targeting the agent to the brain is not desired. Exemplary diseases of the liver include hepatocellular carcinoma (hepatoma) and liver cancer. Exemplary lung diseases include lung cancers such as small cell carcinoma (e.g., oat cell cancer), mixed small cell/large cell carcinoma, combined small cell carcinoma, and metastatic tumors. Metastatic tumors can originate from cancer of any tissue, including breast cancer (e.g., metastatic breast carcinoma), colon cancer, prostate cancer (e.g., metastatic prostate carcinoma), sarcoma, bladder cancer, neuroblastoma, and Wilms' tumor (nephroblastoma). Spleen diseases include cancers such as lymphoma, non-Hodgkin's lymphoma, and certain T-cell lymphomas.

Additional exemplary cancers that may be treated using a conjugate or composition of the invention include breast cancer, cancers of the head and neck including various lymphomas such as mantle cell lymphoma, adenoma, squamous cell carcinoma, laryngeal carcinoma, cancers of the retina, cancers of the esophagus, multiple myeloma, ovarian cancer (e.g., ovarian germ-cell tumors and ovarian carcinoma), uterine cancer, melanoma, colorectal cancer, bladder cancer, prostate cancer, lung cancer (including small cell lung carcinoma and non-small cell lung carcinoma), pancreatic cancer, cervical cancer, head and neck cancer, skin cancers, nasopharyngeal carcinoma, liposarcoma, epithelial carcinoma, renal cell carcinoma, gallbladder adenocarcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease.

As described herein, brain cancers that can be treated with the compounds or the compositions of the invention that are transported efficiently across the BBB include astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, and teratoma. Other exemplary cancers that may be treated with the compounds or compositions of the invention include mycosis fungoides (also known as Alibert-Bazin syndrome or granuloma fungoides), Hodgkin's disease (Hodgkin's lymphoma), acute myelogenous leukemia, acute lymphocytic leukemia, chronic myelogenous leukemia, Kaposi's sarcoma related to acquired immune deficiency syndrome (AIDS), AIDS-related non-Hodgkin's lymphoma, gestational trophoblastic tumors, Ewing's sarcoma, rhabdomyosarcoma, refractory advanced breast cancer, testicular cancer (e.g., malignant tumor of testis, refractory testicular neoplasm, and testicular germ cell tumor carcinoma), refractory advanced malignant neoplasms, diffuse large B-cell lymphoma, osteosarcoma, Burkitt's lymphoma, adult acute lymphocytic leukemia, Burkitt's leukemia, mediastinal neoplasms, lymphoblastic lymphoma, large cell anaplastic lymphoma, plasma cell neoplasm.

A compound or composition of the invention may be administered by any means known in the art; e.g., orally, intraarterially, intranasally, intraperitoneally, intravenously, intramuscularly, subcutaneously, transdermally or per os to the subject. The agent may be, for example, an anti-angiogenic compound.

Combination Therapies

The compounds of the invention may be administered concurrently with other therapeutic agents or other therapeutic regimes. In some embodiments, the additional therapeutic agent or agents may also have a covalent bond to the polypeptides, or derivatives thereof, described herein (e.g., the polypeptides of Table 1 and derivatives thereof). In other embodiments, the additional therapeutic agent or agents are not covalently bound to the polypeptides described herein. Exemplary therapeutic regimes and therapeutic agents that can be used in combination therapy with the compounds of the invention include, but are not limited to: radiation therapy, chemotherapy, high dose chemotherapy, stem cell transplant (e.g., autologous stem cell transplant), bone marrow transplant, surgery, surgery to remove tumors, hyperthermia treatment, cisplatin, irinotecan, irinotecan hydrochloride, carboplatin, chlorambucil (Leukeran®), tositumomab (Bexxar®), rituximab (Rituxan® and MabThere), bleomycin, vincristine, vinblastine, cyclophosphamide, procarbazine, mitoxantrone, prednisone, prednisolone, gemcitabine (Gemzar®), paclitaxel (Taxol®), ifosfamide, methotrexate, doxorubicin, (Adriamycin®), dexamethasone, cyclosporin, Rad-001 (Certican), cytarabine (Ara-C), daunorubicin, fludarabine, idarubicin, vorinostat (SAHA), niacinamide, AZD2171, mitotane, Gemtuzumab ozogamicin (Mylotarg®), mitoxantrone, clofarabine, asparaginase, mercaptopurine, granulocyte colony-stimulating factor (G-CSF or GCSF), vindesine, thioguanine, VM26, VP16, dacarbazine, dactinomycin, temozolomide, thiotepa, epirubicin hydrochloride, carmustine, filgrastim, docetaxel, gefitinib, or pharmaceutically acceptable salts thereof, or any combination thereof.

The second therapeutic agents used in the methods described herein can also be a polypeptide that includes or that consists of the sequence of Angiopep-2 (SEQ ID NO:97), preferably where the Angiopep-2 is conjugated to an anticancer agent (e.g., paclitaxel). An exemplary therapeutic agent that can be used in combination with any of the compounds described herein is ANG1005, which has the following structure:

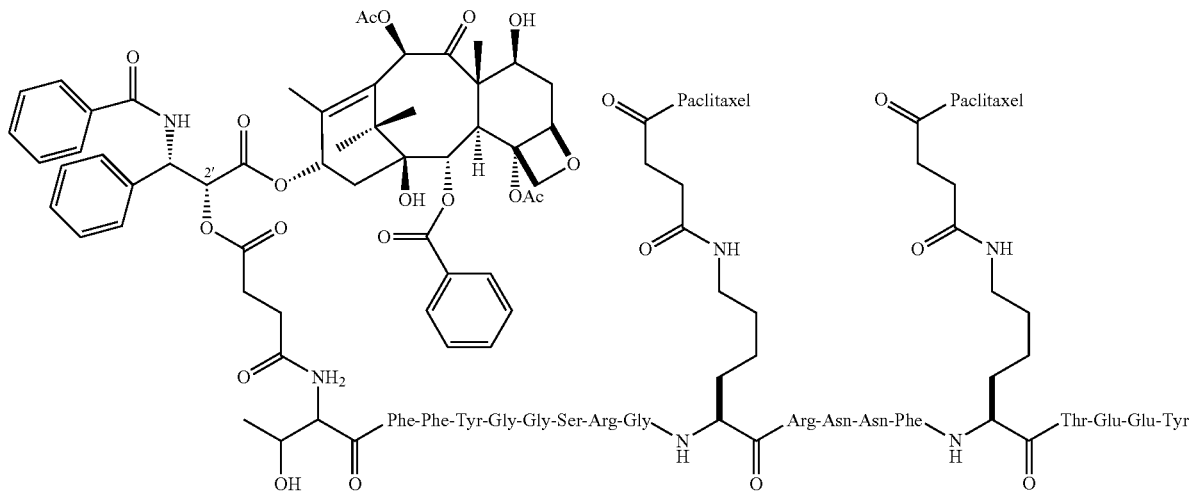

ANG1005:
TxlAn2 (3:1) conjugate

Still other exemplary second therapeutic agents are described in U.S. Pat. No. 7,557,182, herein incorporated by reference.

Pharmaceutical Compositions

Pharmaceutical compositions of the invention include a compound of the invention as described herein, in association with a pharmaceutically acceptable carrier. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially, and intratumorally.

Pharmaceutically acceptable carriers further include 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Other formulations include poly-oxyethylene esters of a fatty acid (e.g., 12-hydroxystearic acid) such as Solutol® HS15. Thus, in some embodiments, a pharmaceutical composition may comprise a) a conjugate described herein, b) Solutol® HS15 and c) an aqueous solution or buffer (e.g., Ringer/Hepes solution at a pH of 5 to 7). The concentration of Solutol® HS15 in the formulation may be at least 5%, 10%, 15%, 20%, 25%, 30%, 35%, 40%, 45%, 50%, or 60% (e.g., 30%) or within any range between any two of these numbers. The concentration of conjugate may be determined based upon the dose required for efficiently treating a subject, or the amount of the ester required for solubility of the conjugate being administered. The use of Solutol in a formulation for administration of a Taxol conjugate is described, for example, in International Publication No. WO 2007/009229, hereby incorporated by reference.

Parenteral Compositions

The pharmaceutical composition may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

The administration of a parenteral composition or formulation that includes a compound of the invention may be administered to a patient over a time period that is, for example, 10, 15, 20, 25, 30, 35, 40, 45, 50, 55, 60, 65, 70, 75, 80, 85, 90, 95, 100, 105, 110, 115, or 120 minutes or, for example, over 0.5, 1.0, 1.5, 2.0, 2.5, 3.0, 3.5, 4.0, 4.5, or 5.0 hours.

Controlled Release Parenteral Compositions

Controlled release parenteral compositions may be in form of aqueous suspensions, microspheres, microcapsules, magnetic microspheres, oil solutions, oil suspensions, or emulsions. The composition may also be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine), poly(lactic acid), polyglycolic acid, and mixtures thereof. Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters)) or combinations thereof.

Solid Dosage Forms for Oral Use

Formulations for oral use include tablets containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the agent in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in *Encyclopedia of Pharmaceutical Technology*, supra.

The compositions of the invention may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

Dosage Regimens

The dosage of any compound, conjugate, or composition described herein or identified using the methods described herein depends on several factors, including: the administration method, the disease (e.g., cancer) to be treated, the severity of the disease, whether the cancer is to be treated or prevented, and the age, weight, and health of the subject to be treated.

With respect to the treatment methods of the invention, it is not intended that the administration of a vector, conjugate, or composition to a subject be limited to a particular mode of administration, dosage, or frequency of dosing; the invention contemplates all modes of administration. The conjugate, or composition may be administered to the subject in a single dose or in multiple doses. For example, a compound described herein or identified using screening methods of the invention may conjugate be administered, for example, once a week for, e.g., 2, 3, 4, 5, 6, 7, 8, 10, 15, 20, or more weeks. A compound of the invention may also be administered, for example, daily for 1, 2, 3, 4, 5, 6, or 7 days or for 1, 2, 3, 4, 5, 6, 7, 8, 10, 15, 20, or more weeks.

Time periods during which the compound of the invention are administered may be followed or preceded by time periods during which the compound is not administered. For example, following administration of the compound as described herein, the compound of the invention is not administered to the patient for 1, 2, 3, 4, 5, 6, or 7 days or for 1, 2, 3, 4, 5, 6, 7, 8, 10, 15, 20, or more weeks. In some embodiments, the patient can receive other therapeutic agents during said time period. These cycles of chemotherapy that include a period of time during which the compound of the invention is administered to a patient that is followed by a period of time during which the compound of the invention is not administered to said patient can be repeated as medically necessary (for example, 1, 2, 3, 4, 5, 6, 7, 8, 9, 10, 11, 12, 13, 14, 15, 16, 17, 18, 19, or 20 times).

It is to be understood that, for any particular subject, specific dosage regimes should be adjusted over time according to the individual need and the professional judgment of the person administering or supervising the administration of the vector, conjugate, or composition. For example, the dosage of a conjugate can be increased if the lower dose does not provide sufficient activity in the treatment of a disease or condition described herein (e.g., cancer). Conversely, the dosage of the compound can be decreased if the disease (e.g., cancer) is reduced or eliminated.

While the attending physician ultimately will decide the appropriate amount and dosage regimen, a therapeutically effective amount of a compound, vector, conjugate, or composition described herein, may be, for example, in the range of 0.0035 µg to 20 µg/kg body weight/day or 0.010 µg to 140 µg/kg body weight/week. Desirably a therapeutically effective amount is in the range of 0.025 µg to 10 µg/kg, for example, at least 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 µg/kg body weight administered daily, every other day, or twice a week. In addition, a therapeutically effective amount may be in the range of 0.05 µg to 20 µg/kg, for example, at least 0.05, 0.7, 0.15, 0.2, 1.0, 2.0, 3.0, 4.0, 5.0, 6.0, 7.0, 8.0, 10.0, 12.0, 14.0, 16.0, or 18.0 μg/kg body weight administered weekly, every other week, or once a month. Furthermore, a therapeutically effective amount of a compound may be, for example, in the range of 0.100 mg/m$^2$ to 2000 mg/m$^2$ administered every other day, once weekly, or every other week. In a desirable embodiment, the therapeutically effective amount is in the range of 1 mg/m$^2$ to 1000 mg/m$^2$, for example, at least 100, 150, 400, or 800 mg/m$^2$ of the compound administered daily, every other day, twice weekly, weekly, or every other week.

For example, the compounds of the invention (e.g., Compound (1)) can be used to administer podophyllotoxin derivatives (e.g., a compound of Formula (I) such as etoposide, etoposide phosphate, etoposide$_{DMG}$, and teniposide) or to administer doxorubicin or doxorubicin derivatives (e.g., Compound (2) or a compound of the invention that includes a compound of Formula (II))) to a patient using any of the methods of administration, dosage amounts, and dosage schedules described herein. Because the compounds of the invention can include covalent bonds to, for example, 1, 2, 3, 4, or 5 molecules of a podophyllotoxin derivative such as those of Formula (I) (e.g., etoposide, etoposide phosphate, etoposide$_{DMG}$, and teniposide) or of Formula (II) (e.g., doxorubicin or epirubicin), this stoichiometry can be used to calculate and to adjust the dosage amount to be administered ("equivalent dose"). For example, the Etoposide:Angiopep-2 (3:1) conjugate ("Etop-An2(3:1)") has a molecular weight of 4354 g/mol, with the etoposide content accounting for 40% of the molecular weight. Similarly, the Doxorubicin:Angiopep-2 (3:1) conjugate has a molecular weight of 4178 g/mol, with the doxorubicin accounting for 40% of the molecular weight. Using this information, the amount of a compound of the invention that is included in a composition for administration (e.g., parenteral or oral) may be calculated in order to administer 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, or 500 mgs/m$^2$/day of a podophyllotoxin derivative (e.g., etoposide, etoposide phosphate, etoposide$_{DMG}$, or etoposide) to a patient. This dosage can be administered to a patient daily for 2, 3, 4, 5, 6, or 7 days. The administration period can be followed by 1, 2, 3, 4, 5, 6, or 7 days or by 2, 3, 4, 5, 6, 7, or 8 weeks of rest without administration of a compound of the invention, with the cycle of administration periods/rest periods repeated for, e.g., 1, 2, 3, 4, 5, 6, 7, 8, 9, or 10 additional times.

The compounds of the invention (e.g., Compounds (1) and (2), or a pharmaceutically acceptable salt thereof) can show improved physicochemical and pharmaceutical properties relative to the respective unconjugated therapeutic agent (e.g., etoposide, etoposide 4-dimethylglycine, or doxorubicin). For example, increased targeting of exemplary cell types, tissues, or organs as described herein (e.g., brain, ovary, liver, lung, kidney, spleen, or muscle) allows for subtherapeutic doses of the compound (e.g., Compounds (1) or (2)) to be administered to a patient. Compounds of the invention can also exhibit reduced toxicity relative to the respective unconjugated therapeutic agent and thus allow for supertherapeutic doses of the compound to be administered to a patient. For example, unconjugated doxorubicin is typically administered in dose schedules that range from 60-75 mg/m$^2$ when administered alone as a single intravenous injection or from 40-50 mg/m$^2$ when administered in combination with another chemotherapeutic agent. Typical dose schedules for unconjugated etoposide or etoposide phosphate can range from 1-5 mg/m$^2$/day, 1-50 mg/m$^2$/day, 35-50 mg/m$^2$/day, or 50-100 mg/m$^2$/day. Improved targeting of cells types, tissues, or organs by the compounds of the invention (e.g., Compounds (1) or (2)) can allow for reduced doses of the therapeutic agent relative to those used for the corresponding unconjugated therapeutic agent ("subtherapeutic doses," i.e., an effective dose that is, for example, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 2000, 3000, 4000, or 5000 times less than the minimum effective dose of the corresponding unconjugated therapeutic agent). Reduced toxicity that can be associated with the compounds of the invention (e.g., Compounds (1) or (2)) can allow for increased doses to be safely administered to a patient relative to those used for the corresponding unconjugated therapeutic agent ("supertherapeutic doses," i.e., an effective dose that is, for example, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 2000, 3000, 4000, or 5000 times more than the maximum allowed dose of the unconjugated therapeutic agent). Similarly, improved physicochemical properties can also affect the doses administered to a patient. For example, improved solubility can allow for the administration of subtherapeutic doses. These improved physicochemical pharmaceutical characteristics can allow for the safe administration of the compounds of the invention (e.g., Compounds (1) or (2)) to, for example, pediatric or geriatric patient populations.

The following examples are intended to illustrate, rather than limit the invention.

EXAMPLES

Example 1

Synthesis of a 3:1 Etoposide:Angiopep-2 Conjugate

Synthesis of the compounds of the invention can be accomplished by the combination of a podophyllotoxin derivative (e.g., a compound of Formula (I) such as etoposide, etoposide phosphate, etoposide$_{DMG}$, or teniposide), a difunctional hydrolyzable linking group (e.g., a dicarboxylic acid or a diisocyanate), and any amino acid sequence described herein, or a functional derivative thereof. Variation of the equivalents of the derivatized podophyllotoxin intermediate (e.g., 2"-glutaryl etoposide) relative to the polypeptide can allow the synthesis of polypeptide conjugates with different stoichiometries (for example, "Etop-An2(1:1)" or "Eto-An2(1:1)", where one molecule of etoposide is bound to the Angiopep-2 polypeptide).

Scheme 5 shows the synthesis of a compound that includes an Angiopep-2 polypeptide covalently bonded to three etoposide molecules ("Etop-An2(3:1)" or ("Eto-An2(3:1)").

Scheme 5

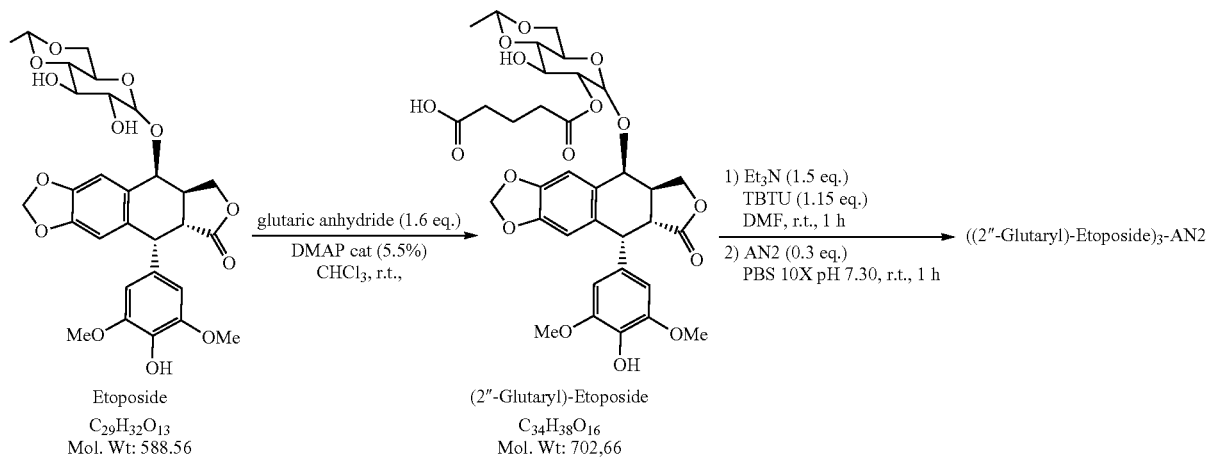

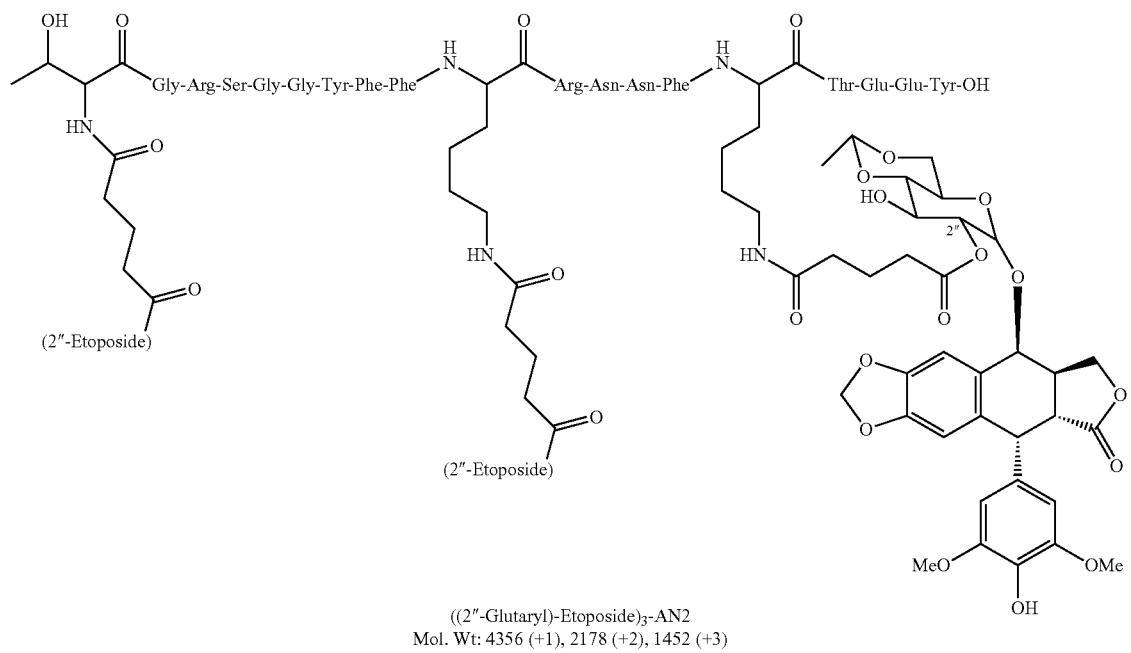

((2″-Glutaryl)-Etoposide)₃-AN2
Mol. Wt: 4356 (+1), 2178 (+2), 1452 (+3)

(2″-Glutaryl)-Etoposide.

To a solution of Etoposide (10 g, 17 mmol) in CHCl₃ (120 mL) were added anhydride glutaric (3.13 g, 27.4 mmol) and DMAP (115 mg, 0.942 mmol). After 72 hours at room temperature, the mixture was evaporated and purified by reverse phase chromatography using a polystyrene/DVB column (15 to 35% acetonitrile (ACN) in H₂O, no trifluoroacetic acid (TFA)). HPLC of the crude product showed a mixture of regioisomers 2″-Glutaryl Etoposide (2″-glu-Etop) and 3″-Glutaryl Etoposide (3″-glu-Etop) in a 2:1 ratio. After evaporation and lyophilisation, (2″-Glutaryl)-Etoposide was obtained as a white powder (4.1 g, 34%). The regioisomeric (3″-glutaryl)-etoposide was also isolated as a white solid (2.4 g, 20%). The purifies of 2″-glu-Etop and 3″-glu-Etop were determined by RP-HPLC. Using a MetaChem Taxsil-3 column and gradient elution (1 mL/min; 10% to 65% (0.05% TFA in H₂O):(0.05% TFA in ACN) over 15 minutes), 2″-glu-Etop has a retention time of 9.00 minutes and 3″-glu-Etop has a retention time of 9.42 minutes. The purity of 2″-glu-Etop (retention time=9.00 minutes) was >98% (99.4%) and the purity of 3″-glu-Etop was >98% (99.6%).

((2″-Glutaryl)-Etop)₃-(Angiopep2) (Etop-An2(3:1)).

To a solution of (2″-Glutaryl)-Etoposide (2.83 g, 4.025 mmol) in anhydrous DMF (400 mL) were added triethylamine (Et₃N; 0.84 mL, 6.037 mmol) and N,N,N′,N′-Tetramethyl-O-(benzotriazol-1-yl)uronium tetrafluoroborate (TBTU; 1.32 g, 4.628 mmol). The reaction mixture was stirred at room temperature for 1 hour (pH=9.3). A solution of AN2 (Angiopep-2, 75% in content, 3.68 g, 1.207 mmol) in PBS 10× buffer (pH 7.3; 200 mL) was prepared by adjusting pH with 10N NaOH (to pH 7.3). After cooling with dry iced bath, the previously activated acid was added (4×100 mL) to Angiopep-2, and the pH of the mixture was adjusted to 7.2 by addition of 10N NaOH. After 1 hour at room temperature, the reaction was filtered to eliminate phosphate salts and evaporated to obtain 35 mL of the crude mixture. HPLC of the crude product showed a mixture of (3:1)- and (2:1) conjugates in a 3:1 ratio. The residue was purified by reverse phase chromatography using a polystyrene/DVB column (15 to 37.5% ACN in H$_2$O). After purification, 0.1% acetic acid was added to the combined fractions in order to increase the solubility. Evaporation and lyophilisation of the mixture afforded the Etop-An2(3:1) product as a white solid (596 mg, 12%). Using a MetaChem Taxsil-3 column and gradient elution (1 mL/min; 10% to 65% (0.05% TFA in H$_2$O):(0.05% TFA in ACN) over 15 minutes), the isolated product was found to have a retention time of 9.36 minutes and to be >95% (97.3%) pure. m/z (ESI-TOF): 2178 (+2), 1452 (+3).

Example 2

Synthesis of a 3:1 Etoposide$_{DMG}$:Angiopep-2 Conjugate

The procedure described in Example 1 can be used to prepare compounds that include peptides conjugated to other podophyllotoxin derivatives. For example, Etoposide$_{DMG}$ can be used to prepare the conjugate shown in Scheme 7 ("Etop$_{DMG}$-An2 (3:1)") using the synthetic procedure shown in Scheme 6.

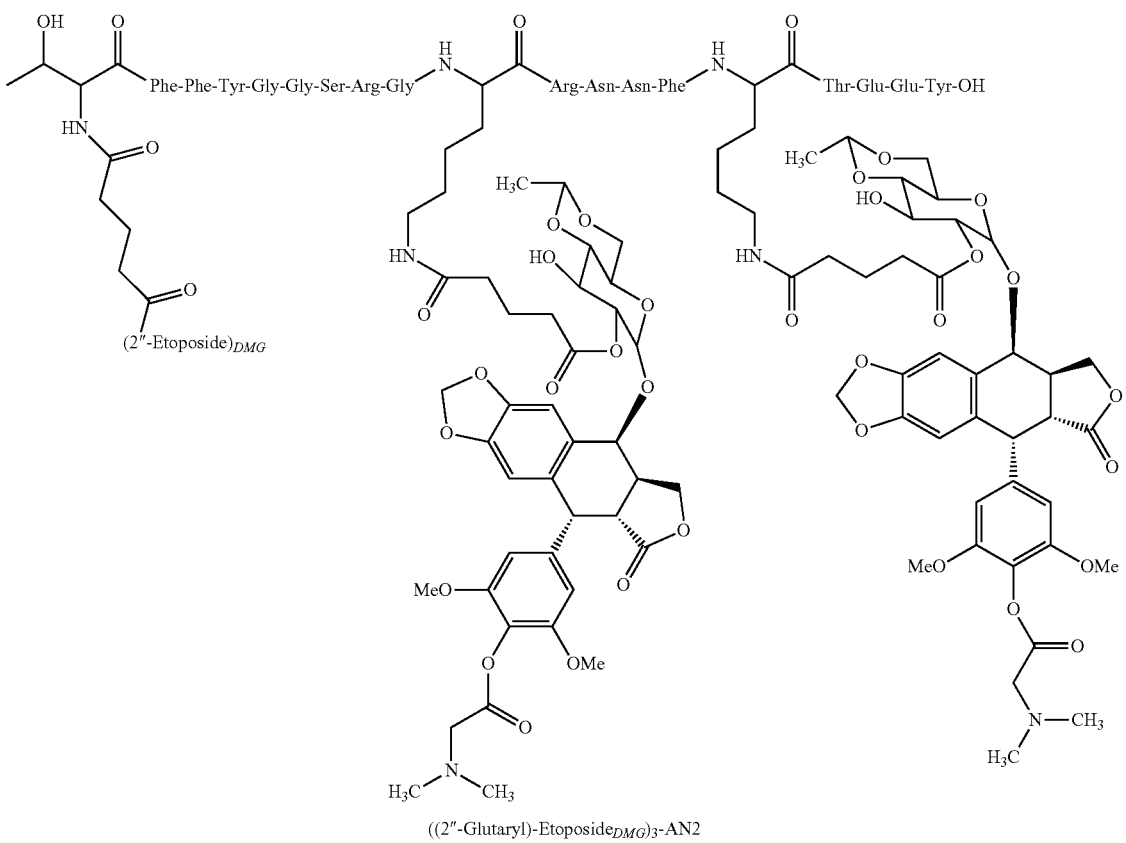

Scheme 6

((2″-Glutaryl)-Etoposide$_{DMG}$)$_3$-AN2

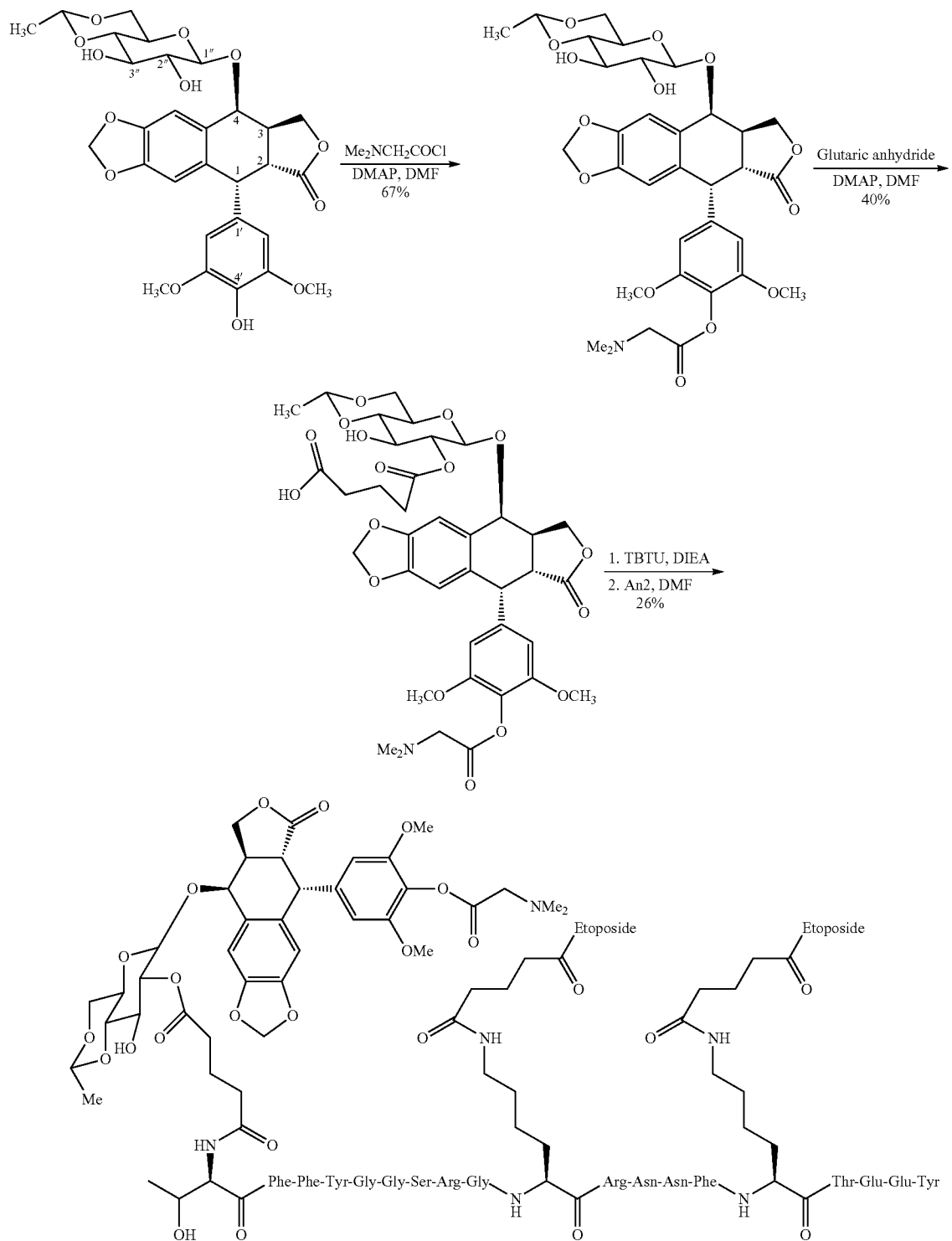

Etoposide 4'-Dimethylglycine:

A mixture of etoposide (235 mg, 0.4 mmol) and DMAP (73 mg, 0.6 mmol) in DMF (4 mL) was stirred at room temperature for 20 minutes, and then N,N-dimethylacetyl chloride (96 mg, 0.52 mmol) was added in one pot with stirring. After 30 minutes, the reaction was complete according to HPLC. Formic acid (1M in DMF, 0.5 mL) was added, and the solvent was concentrated to 1 mL. The resulting solution was loaded onto an AKTA RPC column for purification (gradient 10% to 30% MeCN in $H_2O$ with 0.1% Formic acid). After lyophilization, etoposide 4'-dimethylglycine ("Etoposide$_{DMG}$" or "Etop$_{DMG}$"; 180 mg, 67%) was obtained as a colorless powder. $^1$H NMR (CD$_3$OD) δ 7.01 (1H, s), 6.56 (1H, s), 6.39 (2H, s), 5.98 (2H, d, J=2.9 Hz), 5.05 (1H, d, J=3.4 Hz), 4.77 (1H, q, J=4.9 Hz), 4.68 (1H, d, J=5.4 Hz), 4.66 (1H, d, J=7.8 Hz), 4.46 (2H, s), 4.45 (1H, dd, J=10.3, 8.8 Hz), 4.31 (1H, t, J=8.0 Hz), 4.17 (1H, dd, J=10.3, 4.9 Hz), 3.68 (6H, s), 3.56 (1H, q, J=10 Hz), 3.54 (1H, t, J=9.3 Hz), 3.52 (1H, dd, J=14.2, 5.6 Hz), 3.32 (1H, m), 3.26 (1H, dd, J=9.1, 4.1 Hz), 3.24 (1H, dd, J=9.2, 5.4 Hz), 3.02 (6H, s), 2.96 (1H, m), 1.33 (3H, d, J=4.9 Hz). $^{13}$C NMR (DMSO) δ 175.26, 168.68, 151.35, 148.49, 147.01, 139.39, 132.74, 129.6, 127.28, 110.65, 110.45, 108.02, 102.19, 102.02, 99.25, 80.78, 75.06, 73.39, 72.41, 68.43, 68.01, 66.44, 59.73, 56.63, 56.47, 45.03, 43.86, 37.89, 20.99; HRMS (MicroTOF) calcd. for C$_{33}$H$_{39}$NO$_{14}$ 673.2371. found 274.2534 (M+1).

Etoposide 4'-Dimethylglycine 2"-Glutaric acid:

A mixture of etoposide 4'-dimethylglycine (655 mg, 0.97 mmol) and DMAP (18 mg, 0.15 mmol) in chloroform (11 mL) was cooled to 0° C. DMF (3 mL) and N,N-diisopropylethylamine (DIEA; 0.25 mL, 1.46 mmol) were added consecutively, followed by glutaric anhydride (222 mg, 1.94 mmol). The reaction mixture was stirred at room temperature, monitored by HPLC. After 2 days, the solvent was concentrated to 3 mL. The resulting solution was loaded to an AKTA RPC column for purification (gradient elution, 10% to 30% MeCN in H$_2$O), and Etoposide 4'-Dimethylglycine 2"-Glutaric acid (305 mg, 40%) was obtained as a white powder after lyophilization. $^1$H NMR (CD$_3$OD) δ 7.0 (1H, s), 6.53 (1H, s), 6.39 (2H, s), 5.99 (2H, d, J=4.6 Hz), 4.97 (1H, q, J=7.9 Hz), 4.78 (1H, q, J=4.75 Hz), 4.74 (1H, d, J=7.9 Hz), 4.68 (1H, d, J=5.6 Hz), 4.45 (2H, s), 4.41 (1H, dd, J=9.6, 8.8 Hz), 4.29 (1H, t. J=8.2 Hz), 4.15 (1H, dd, J=10.0, 4.5 Hz), 3.78 (1H, t, J=9.4 Hz), 3.69 (6H, s), 3.61 (1H, t, J=10.2 Hz), 3.42 (1H, td, J=9.6, 5.2 Hz), 3.33 (1H, dd, J=8.7, 8.2 Hz), 3.3 (1H, dd, J=13.4, 5.3 Hz), 3.02 (6H, s), 2.93 (1H, m), 2.26 (1H, m), 2.16 (2H, m), 2.02 (1H, m), 1.64 (2H, m), 1.32 (3H, d, J=4.9 Hz). $^{13}$C NMR (DMSO) δ 175.96, 175.33, 172.46, 163.74, 151.14, 148.96, 147.43, 139.53, 131.90, 129.83, 126.42, 110.20, 109.18, 107.40, 101.91, 100.65, 99.63, 80.39, 74.55, 73.95, 71.55, 71.29, 68.43, 67.82, 66.46, 56.43, 55.35, 43.90, 43.15, 40.82, 38.0, 32.86, 32.59, 19.93, 19.39. HRMS (MicroTOF) calcd. for C$_{38}$H$_{45}$NO$_{17}$ 787.2687. found 788.2432 (M+1).

(Etoposide-4'-Dimethylglycine-2"-Glutaric)$_3$-Angiopep-2 Conjugate ("Etop-4'-DMGly-2"-Glu)$_3$-An2" or "Etop$_{DMG}$-An2(3:1)"):

DIEA (0.17 mL, 0.98 mmol) was added dropwise to a mixture of Etoposide 4'-Dimethylglycine 2"-Glutaric acid (330 mg, 0.42 mmol) and TBTU (145 mg, 0.46 mmol) in DMF (24 mL). The mixture was stirred at room temperature for 50 minutes. A solution of Angpep-2 (422 mg, 0.14 mmol) in DMSO (1.5 mL) and DMF (9 mL) was then added, followed by DIEA (0.084 mL, 0.48 mmol). The mixture was stirred at room temperature for 20 minutes. An aliquot (10 mL) was taken for HPLC analysis, and it showed the reaction was complete. After stirring for another 10 minutes, the reaction solution was concentrated to 3 mL and purified using AKTA RPC column (gradient elution, 10% to 25% MeCN in H$_2$O with 0.05% formic acid). (Etop-4'-DMGly-2"-Glu)$_3$-An2 (172 mg, 26%) was yielded as a colorless powder after lyophilization. MS (MicroTOF), m/z, 2305.9327 (2+), 1537.6443 (3+), 1153.7463 (4+), 922.7970 (5+).

Example 3

Synthesis of a 3:1 Doxorubicin:Angiopep-2 Conjugate ("(DoxSu)$_3$-An2")

A 3:1 doxorubicin:angiopep-2 conjugate be prepared according to the synthetic scheme shown in Scheme 8 and described herein.

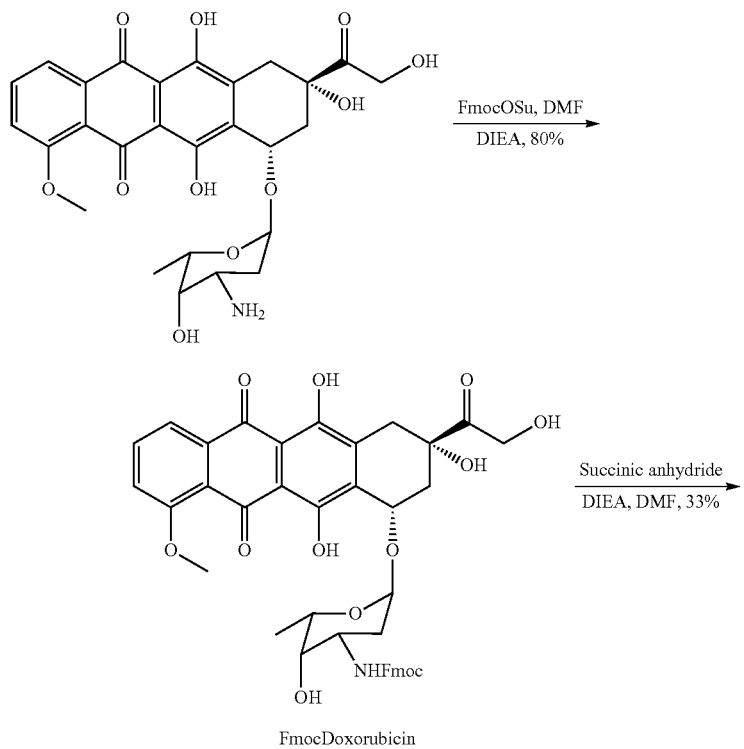

Scheme 8

FmocDoxorubicin

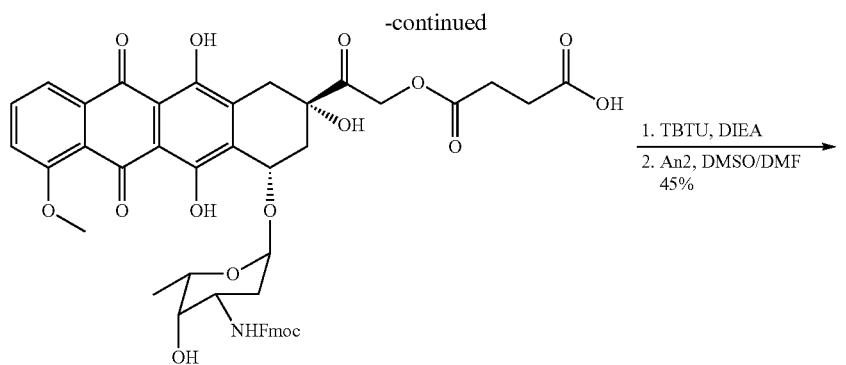

FmocDoxSuOH

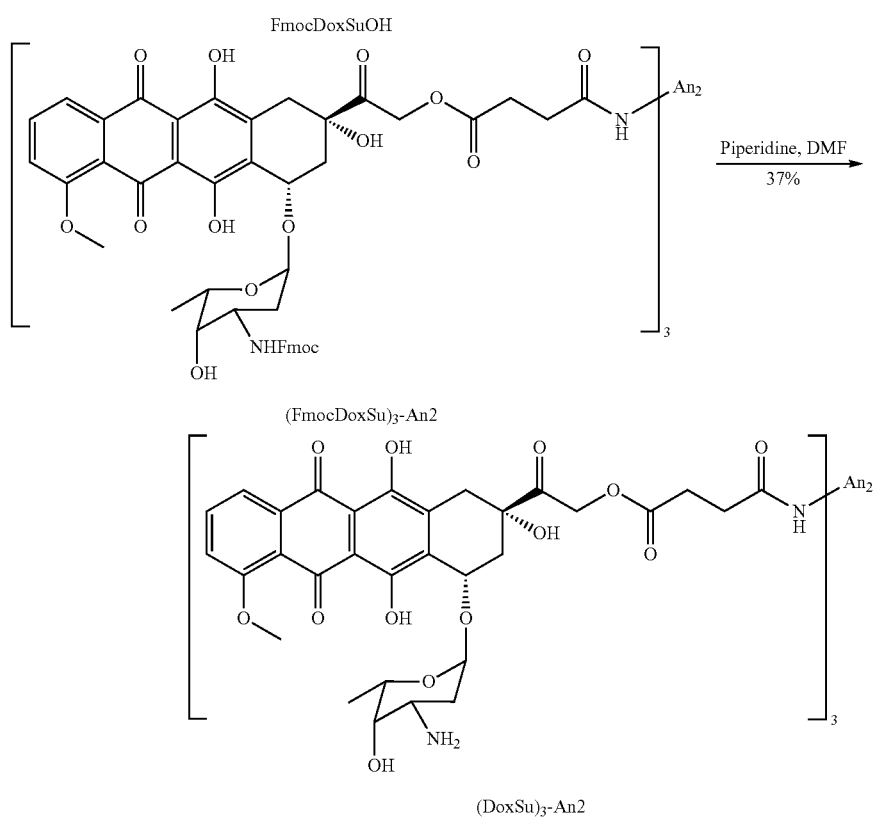

(FmocDoxSu)₃-An2

(DoxSu)₃-An2

FmocDoxorubicin:

DIEA (1.5 mL, 8.63 mmol) was added dropwise to a solution of doxorubicin (2.0 g, 3.45 mmol) and 9-fluorenylmethyl N-succinimidyl carbonate (FmocOSu; 2.32 g, 6.9 mmol) in DMF (35 mL) with stirring. The mixture was stirred at room temperature for 3 hours and concentrated. The resulting residue was triturated with 0.1% TFA in H₂O (3×20 mL), washed with Et₂O (8×20 mL). The resulting red solid was collected and dried over vacuum to give FmocDoxorubicin as a red powder (2.1 g, 80% yield). HPLC purity, 98%. MS (ESI, MicroTOF), 788. 2411 (M+Na).

FmocDoxSuOH:

DIEA (0.17 mL, 1.0 mmol) was added dropwise to a solution of FmocDoxorubicin (0.28 g, 0.366 mmol) and succinic anhydride (0.11 g, 1.1 mmol) in DMF (20 mL) under stirring. The mixture was stirred at room temperature and monitored by HPLC. After two days, the solvent was removed and the resulting residue was purified using a Biotage column (silica gel, 2% to 9% MeOH in DCM) to give FmocDoxSuOH as a red powder (100 mg, 33% yield). HPLC purity: 95%. MS (ESI, MicroTOF), 888. 2577 (M+Na).

(FmocDoxSu)₃-An2:

DIEA (0.25 mL, 1.44 mmol) was added dropwise to a solution of FmocDoxSuOH (599 mg, 0.692 mmol) and TBTU (231 mg, 0.72 mmol) in DMF (21 mL) under stirring. The mixture was stirred at room temperature for 50 minutes and then a solution of Angpep-2 (671 mg, 0.229 mmol) in DMSO (2 mL) and DMF (12 mL) was added. The mixture was stirred at room temperature for 20 minutes, at which time HPLC showed the reaction was complete. After stirring for another 10 minutes, the solvent was removed and the residue was purified using a Biotage C18 column (40% to 80% MeCN in water and 0.05% TFA) to give (FmocDoxSu)₃An-2 as a red powder (500 mg, 45% yield). HPLC purity, 95%. MS (ESI, MicroTOF), m/z 2423.4239 (2+), 1615.6190 (3+).

(DoxSu)₃-An2:

Piperidine (20% in DMF, 1.5 mL) was added to a solution of (FmocDoxSu)₃An-2 (260 mg, 0.053 mmol) in DMSO (1 mL) and DMF (12 mL). The solution became blue. After stirring for 10 minutes, the solution was cooled to 0° C. and treated with formic acid (0.5 M in DMF, 6 mL) to get a clear red solution. The solvent was removed using vacuum pump, and the resulting residue was triturated with $Et_2O$ (3×10 ml) and AcOEt (3×10 ml). The resulting red solid was purified using AKTA RPC 30 column (10% to 40% MeCN in water and 0.15% formic acid) to give $(DoxSu)_3An-2$ as a red powder (82 mg, 37% yield). HPLC purity: 95%. MS (ESI, MicroTOF), m/z 2089.9674 (2+), 1393.2419 (3+), 1045.4395 (4+).

Example 3

Effect of Etoposide, Etoposide-Angiopep Conjugates, Doxorubicin, and Doxorubicin-Angiopep Conjugates on Cell Proliferation For the in vitro cell proliferation assay, between 2.5 and 5×10⁴ of U87 or SK-HEP-1 cells were seeded in a 24 well tissue culture microplate in a final volume of 1 mL of medium with 10% serum and incubated for 24 hours at 37° C. and 5% $CO_2$. The medium was then replaced with serum-free medium and incubated overnight. The next morning the agent was freshly dissolved in dimethyl sulfoxide (DMSO) and the medium was replaced with complete medium containing the agent at different concentrations in triplicate. The final concentration of DMSO was 0.1%. The control used was a microplate well with cells and without agent. The cells were incubated for 48 to 72 hrs at 37° C. and 5% $CO_2$. After the incubation, the medium was changed and replaced with 1 mL of complete medium containing [$^3H$]-thymidine (1 pCi/assay). The plate was incubated at 37° C. and 5% $CO_2$ for 4 hrs. The medium as removed, and the cells were washed with PBS at 37° C. The cells were fixed with a mix of ethanol:acetic acid (3:1), washed with water, and precipitated 3 times with 10% of ice-cold TCA (trichloroacetic acid). Finally 500 μL of PCA (perchloric acid) were added to the wells and the microplates were heated for 30 min at 65° C. and 30 min at 75° C. The contents of each well were then transferred to a scintillation vial with 10 mL of scintillation cocktail and the activity was measured in CPM (count per minute) on a liquid scintillation counter Tri-Carb from Packard. The results of the cell proliferation assay using unconjugated etoposide, Etop-An2(1:1), and Etop-An2(3:1) are shown in Table 4. Table 5 shows the results obtained for $Etop_{DMG}$-An2(3:1), unconjugated etoposide$_{DMG}$, the doxorubicin/Angiopep-2(3:1) conjugate ("Doxorubicin-An2 (3:1)"), and unconjugated doxorubicin.

In addition to the in vitro studies, the inhibition of cell proliferation has been studied in xenograft tumor models and these results are shown in FIG. 1. U87 glioblastoma cells (2.5×106) were subcutaneously implanted in the right flank of nude mice. Treatments started on day 15 after implantation (corresponding to day 0 on the graph shown in FIG. 1) when tumor volume reached about 150-200 mm³. The mice were treated once a week for three weeks by i.v. bolus injection with doxorubicin (6 mg/kg) and doxorubicin-An2 conjugate (20 and 40 mg/kg). The doxorubicin-An2 conjugate was diluted in acidified D5W (5% dextrose in water) at 5 mg/ml.

TABLE 4

| Drug | $IC_{50}$ (nM) | | |
|---|---|---|---|
| | 24 hours | 48 hours | 72 hours |
| | U-87 Cells | | |
| Etoposide | 160 | 221 | 145 |
| Eto-An2 (1:1) | 1313 | 722 | 550 |
| Eto-An2 (3:1) | 453 | 151 | 164 |
| (Etoposide equiv.) | (1359) | (453) | (492) |
| | SK-HEP-1 | | |
| Etoposide | 116 | 56 | 50 |
| Eto-An2 (1:1) | 679 | 245 | 153 |
| Eto-An2 (3:1) | 160 | 59 | 52 |
| (Etoposide equiv.) | (480) | (168) | (156) |

TABLE 5

| Drug | $IC_{50}$ (nM) Glioblastoma (U87) | Hepatocarcinoma (SK-Hep-1) | Lung Carcinoma (NCI-H460) |
|---|---|---|---|
| $Etop_{DMG}$ | 145 | 62 | 90 |
| $Etop_{DMG}$-An2(3:1) | 330 | 48 | 148 |
| Doxorubicin | 18 | 10 | 11 |
| Doxorubicin-An2 (3:1) | 6.0 | 4.6 | 7.3 |

Example 3

In Situ Brain Perfusion Studies

The procedures described in U.S. Patent Publication 20060189515, herein incorporated by reference, were used for the in situ brain perfusion studies. These procedures are further described herein.

Example 3a

Etop-An2(3:1)

The brain uptake of the compounds of the invention (e.g., Etop-An2(3:1), $Etop_{DMG}$-An2(3:1), and Doxorubicin-An2 (3:1)) relative to the corresponding unconjugated drugs were measured using in situ brain perfusion techniques described herein and in Dagenais et al., *J. Cereb. Blood Flow Metab.* 20(2):381-386 (2000). The uptake of [$^{125}I$]-polypeptides to the luminal side of mouse brain capillaries was measured using the in situ brain perfusion method adapted in our laboratory for the study of agent uptake in the mouse brain.

Polypeptides were iodinated with standard procedures using iodo-beads from Sigma. Briefly polypeptides were diluted in 0.1 M phosphate buffer, pH 6.5 (PB). Two iodo-beads were used for each protein. These beads were washed twice with 3 mL of PB on a Whatman filter and re-suspended in 60 of PB. $^{125}I$ (1 mCi) from Amersham-Pharmacia biotech was added to the bead suspension for 5 min at room temperature. Each iodination was initiated by the addition of the polypeptide (100 μg). After an incubation of 10 min at room temperature, the free iodine was removed by HPLC.

Briefly, the right common carotid of ketamine/xylazine (140/8 mg/kg i.p.) anesthetized mice was exposed and ligated at the level of the bifurcation of the common carotid, rostral to the occipital artery. The common carotid was then catheterized rostrally with polyethylene tubing filled with heparin (25 U/mL) and mounted on a 26-gauge needle. The syringe containing the perfusion fluid ([$^{125}$I]-polypeptides or [$^{14}$C]-inulin in Krebs/bicarbonate buffer at a pH7.4 gassed with 95% $O_2$ and 5% $CO_2$) was placed in an infusion pump (Harvard pump PHD 2000; Harvard Apparatus) and connected to the catheter. Prior to the perfusion, the contralateral blood flow contribution was eliminated by severing heart ventricles. The brain was perfused for the indicated times at a flow rate of 1.15 mL/min. After 14.5 min of perfusion, the brain was further perfused for 60 seconds with Krebs buffer to wash the excess of [$^{125}$I]-proteins. Mice were then decapitated to terminate perfusion and the right hemisphere was isolated on ice before being subjected to capillary depletion. Aliquots of homogenates, supernatants, pellets and perfusates were taken to measure their contents in [$^{125}$I]-conjugates by TCA precipitation and to evaluate the apparent volume of distribution.

Figure 2A:
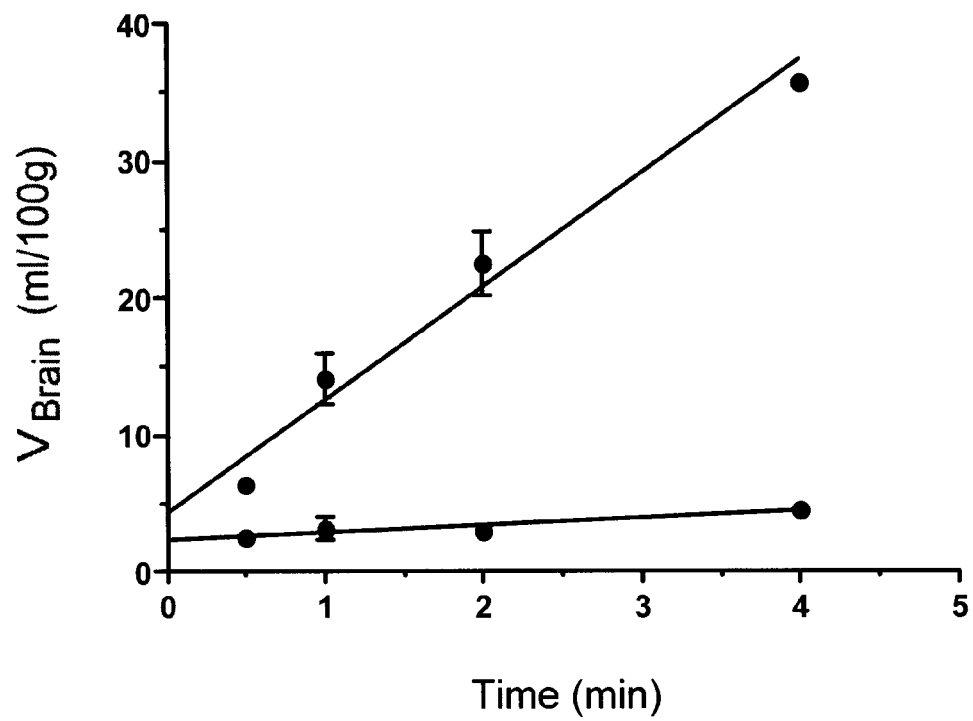
FIG. 2A shows the brain uptake of the 3:1 Etoposide: Angiopep-2 conjugate ("Etop-An2(3:1)") measured by in situ brain perfusion.
Figure 2B:
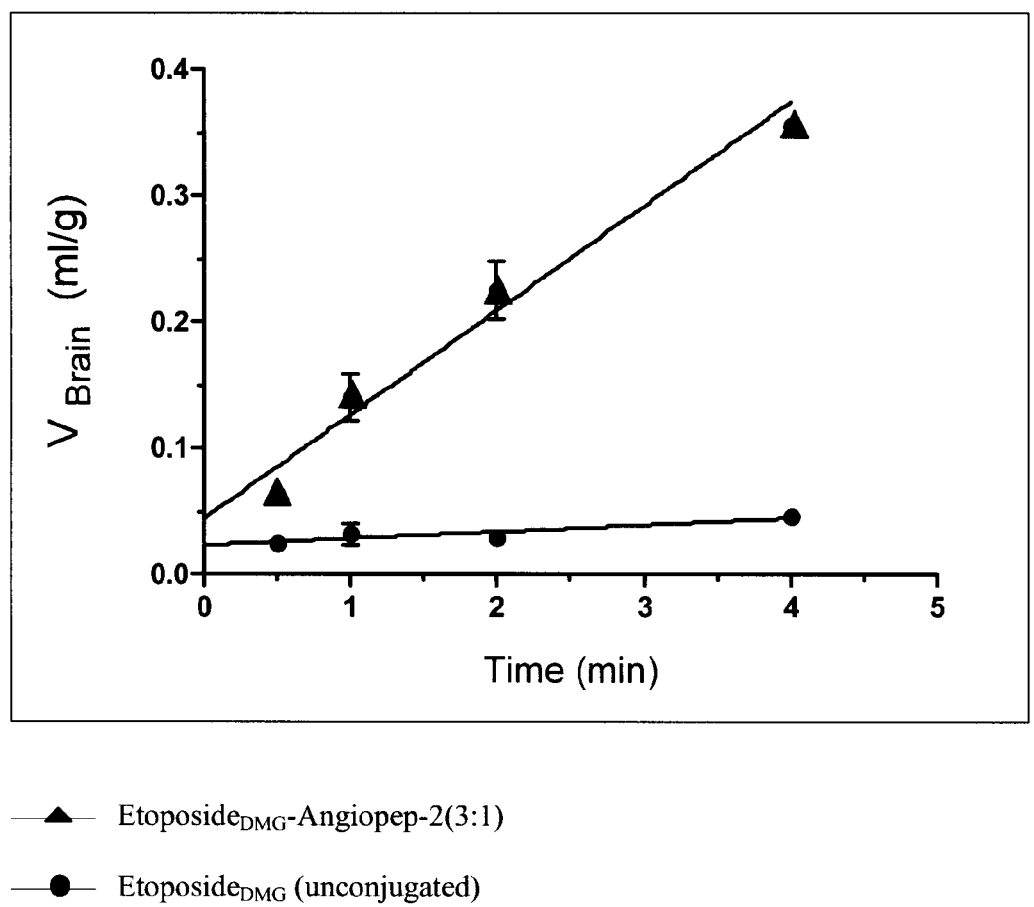
FIG. 2B shows the brain uptake of the 3:1 etoposide 4′-dimethylglycine:Angiopep-2 conjugate ("Etop$_{DMG}$-An2(3:1)") measured by in situ brain perfusion.
Figure 2C:
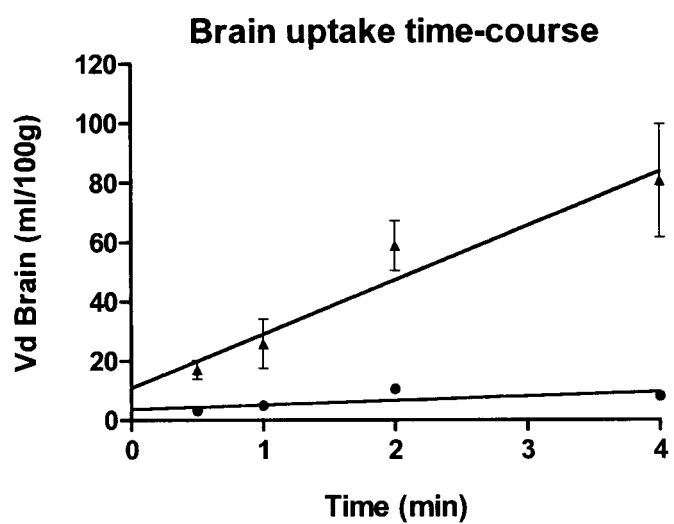
FIG. 2C shows the brain uptake of the Doxorubicin-An2 (3:1) measured by in situ brain perfusion.
Figure 3:
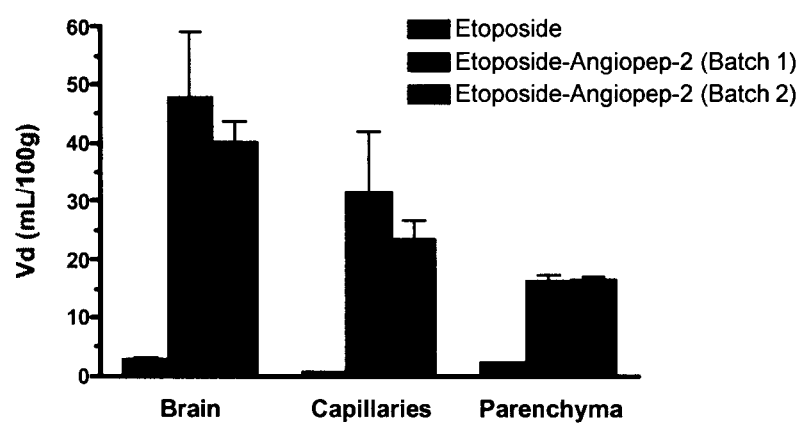
FIG. 3 shows the in situ perfusion of Etop-An2(3:1).
Figure 4A:
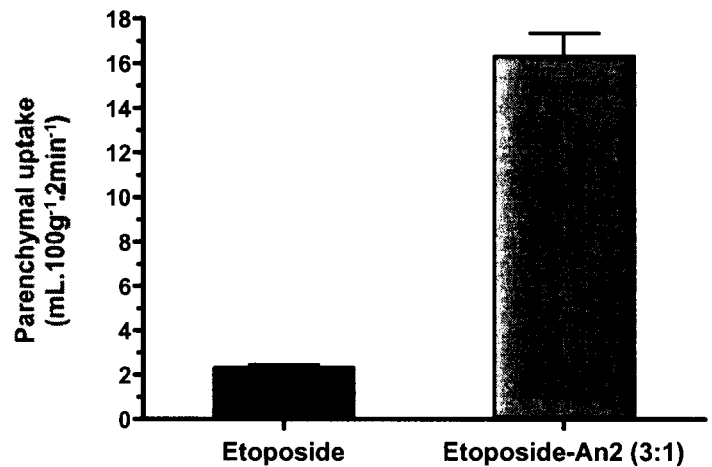
FIG. 4A shows the parenchymal uptake of unconjugated etoposide compared to Etop-An2(3:1).
Figure 4B:
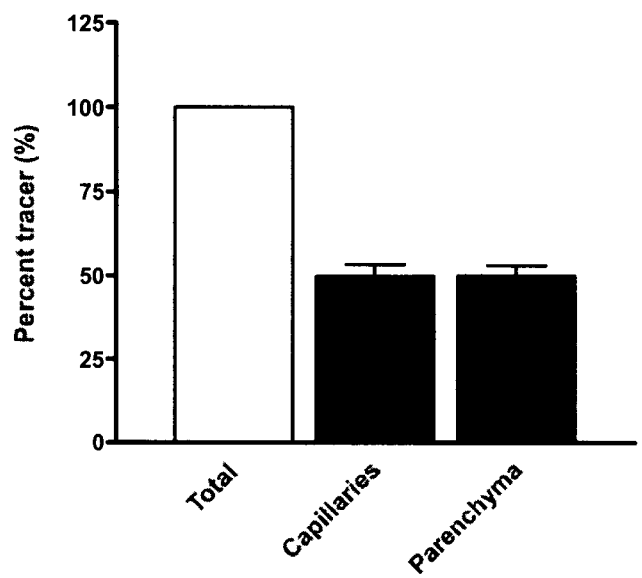
FIG. 4B shows the brain repartition of Etop-An2(3:1) following brain capillary depletion.
Figure 5:
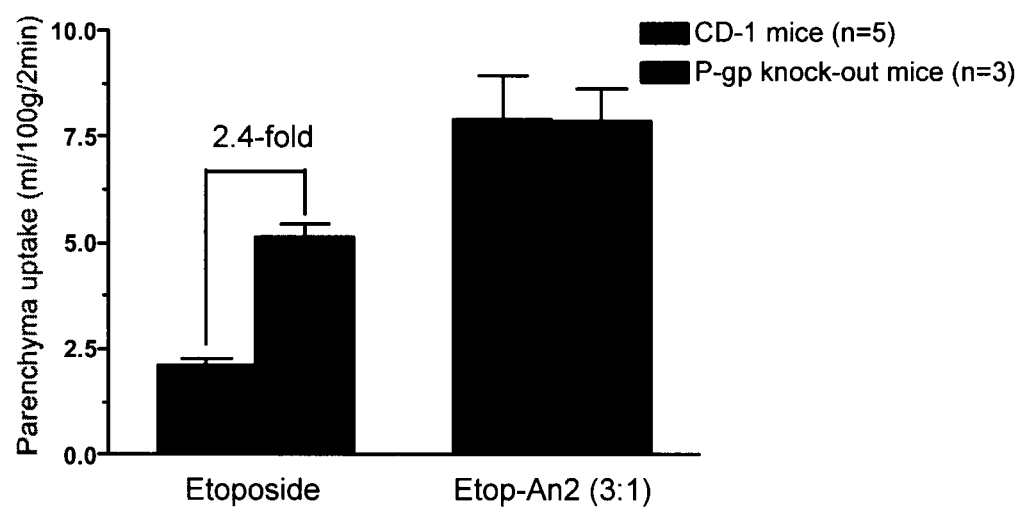
FIG. 5 shows the in situ brain perfusion of Etop-An2(3:1) compared to unconjugated etoposide in CD-1 versus P-gp knock-out mice.
Figure 6:
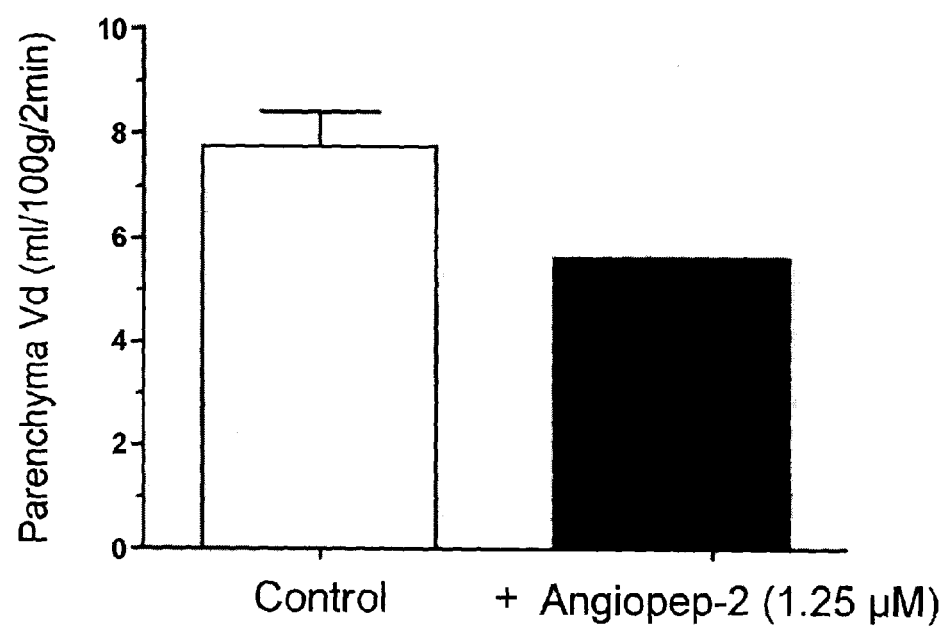
FIG. 6 shows the inhibition of brain uptake of Etop-An2 (3:1) by Angiopep-2.

The results of these experiments are illustrated in FIGS. 2A-D and 3. In FIG. 2A, in situ brain perfusion shows that the Vd is higher for Etop-An2(3:1) than for the unconjugated etoposide (i.e., the observed slope for Etop-An2(3:1) is greater than that observed for unconjugated etoposide). Similar trends are observed for Etop$_{DMG}$-An2(3:1) (FIG. 2B) relative to unconjugated Etoposide$_{DMG}$ and for doxorubicin-An2(3:1) relative to unconjugated doxorubicin (FIG. 2C). As can be see from FIG. 2C, the ratio of the $K_{in}$ for Doxorubicin-An2(3:1):unconjugated doxorubicin is 15. This procedure also distinguishes between compounds remaining in the brain vascular compartment from those having crossed the abluminal endothelial membrane to enter the brain parenchyma. FIG. 3 shows the in situ perfusion of Etop-An2(3:1). In each grouping in this graph, the left bar represents unconjugated etoposide, the middle bar represents Etop$_{DMG}$-An2(3:1) (Batch 1), and the right bar represents Etop$_{DMG}$-An2(3:1) (Batch 2). The brain repartition of Etop-An2(3:1) following brain capillary depletion is illustrated in FIGS. 4A and 4B. Moreover, in contrast to etoposide the brain uptake of Etop-An2(3:1) is similar in wild-type and P-gp knock-out mice, indicating that Etop-An2(3:1) is not a P-gp substrate (FIG. 5). In this figure, the left bar of each groups shows the results obtained using CD-1 mice and the right bar shows the results obtained using P-gp knockout mice. The brain uptake of Etop-An2(3:1) can be inhibited by the coadministration of an unconjugated polypeptide. FIG. 6 shows that the co-perfusion of [$^{125}$I]-Etop-An2(3:1) with a two-fold excess of unconjugated Angiopep-2 reduces the parenchyma Vd by 27%.

Example 3b

Etop$_{DMG}$-An2 (3:1) and Doxorubicin-An2(3:1)

Figure 7:
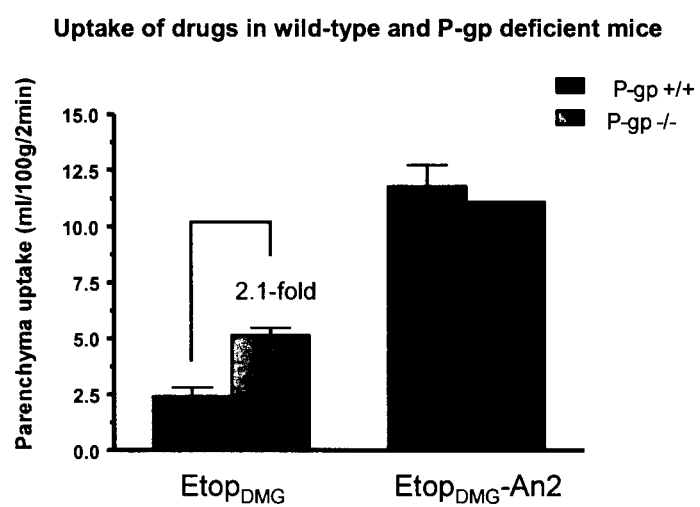
FIG. 7 shows the in situ brain perfusion of Etop$_{DMG}$-An2 compared to unconjugated Etop$_{DMG}$ in CD-1 versus P-gp knock-out mice.

The brain uptake of Etop$_{DMG}$-An2 (3:1) relative to the unconjugated Etop$_{DMG}$ was measured using the methods described for Example 3a, and these results are shown in Table 6 and in FIG. 7. Table 6 also includes the corresponding data for Doxorubicin-An2(3:1) and doxorubicin. In contrast to unconjugated Etop$_{DMG}$, the brain uptake of doxorubicin-An2(3:1) is similar in wild-type and P-gp knock-out mice, indicating that doxorubicin-An2(3:1) is not a P-gp substrate.

TABLE 6

| Drug | Brain $K_{in}$ (ml/s/g) |
| --- | --- |
| Etop$_{DMG}$-An2 | $1.4 \times 10^{-3}$ |
| Etop$_{DMG}$ | $9.0 \times 10^{-5}$ |
| Doxorubicin-An2(3:1) | $3.7 \times 10^{-3}$ |
| Doxorubicin | $2.8 \times 10^{-4}$ |

Example 4

Plasma kinetics of the 3:1 etoposide-Angiopep-2 conjugate

Figure 8:
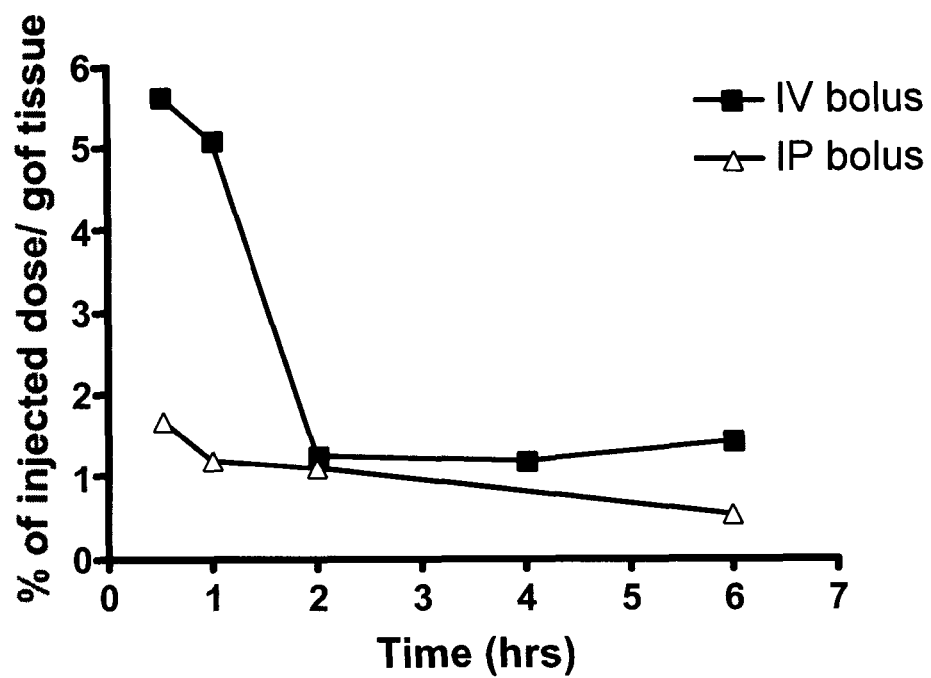
FIG. 8 shows data on the data on plasma kinetics of Etop-An2(3:1).

FIG. 8 describes the plasma kinetics of Etop-An2(3:1) following administration as a bolus. Radiolabeled ($^{125}$I) Etop-An2 (20 mg/kg) was injected in bolus by intravenous (i.v.) or intraperitoneal (i.p.) routes in CD-1 mice weighing about 25-30 g. The injection solution was composed of 12.5% dimethylsulfoxide (DMSO), 12.5% anhydrous ethanol 25% polyethylene glycol 400 (PEG400) and 50% NaCl/Glycine buffer. At several time intervals (0.5, 1, 2, and 6 hours) the blood was collected by cardiac puncture and animals were sacrificed. After blood centrifugation, the plasma radioactivity was measured in a gamma counter (Wizard 1470 Automatic Gamma Counter). The radioactivity was interpreted as % of injected dose per gram of plasma. Results were plotted using GraphPad prism software and the area under the curve (AUC) for each injection mode was calculated. The bioavailability of intraperitoneal Etop-An2 conjugate was then estimated by dividing the AUC after i.p. injection by the AUC after i.v. injection. The estimated bioavailability following i.p. administration is calculated as 46%. Pharmacokinetic parameters of Etop-An2(3:1) following IV bolus administration in mice are shown in Table 7. Literature data for unconjugated etoposide shows a $T_{1/2\alpha}$=0.13 hour (Reddy et al., *Journal of drug targeting*, 13(10): 543-553 (2005)).

TABLE 7

| Molecule | Dose (mg/kg) | $T_{max}$ (min) | $C_{max}$ (µg/mL) | $T_{1/2\alpha}$ (hr) | $AUC_{0-\infty}$ (hr°µg/mL) | Elim. Rate Const. (hr$^{-1}$) |
| --- | --- | --- | --- | --- | --- | --- |
| Etop-An2 (3:1) | 20 | 5 | 46 | 0.43 | 82 | 1.6 |

Example 5

Tissue distribution of 3:1 etoposide$_{DMG}$-Angiopep-2 conjugate and 3:1 etoposide-Angiopep-2 conjugate The effect of conjugation of an agent to a vector on distribution of the agent or the pharmacokinetics of a polypeptide that is conjugated to an agent was evaluated by administering a labeled polypeptide or conjugate to an animal and measuring distribution of the polypeptide or conjugate to organs (e.g., using $^3$H or $^{125}$I labeled conjugates) to mice. Similar experiments can be performed with compounds that include any of polypeptides described herein (e.g., the polypeptides described in Table 1 such as AngioPep-3, AngioPep-4a, AngioPep-4b, AngioPep-5, AngioPep-6, and AngioPep-7, or analogs thereof). Here, the unconjugated anticancer agent and the conjugates were injected intravenously to mice as a bolus. Tissues were collected at different times (0.25, 0.5, 1, and 4 hrs) and homogenized. To quantify the amount of $^3$H-labeled conjugate, tissue homogenates were digested with tissue solubilizer, and 10 mL of liquid scintillator was added to samples. The amount of the $^{125}$I labeled conjugate, in the different tissues is measured after TCA precipitation. Radioactivity associated with the tissues is quantified. The area under the curve (AUC 0-4) is estimated using the Prism software and is plotted for the different tissues.

Figure 9:
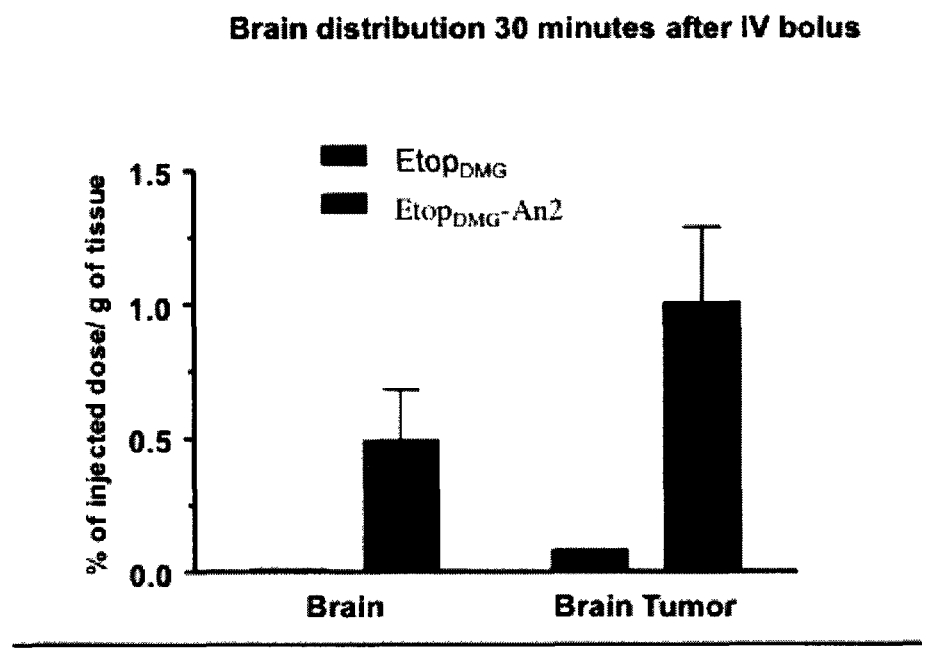
FIG. 9 shows the brain distribution of Etop$_{DMG}$-An2 following IV bolus administration in mice.
Figure 10:
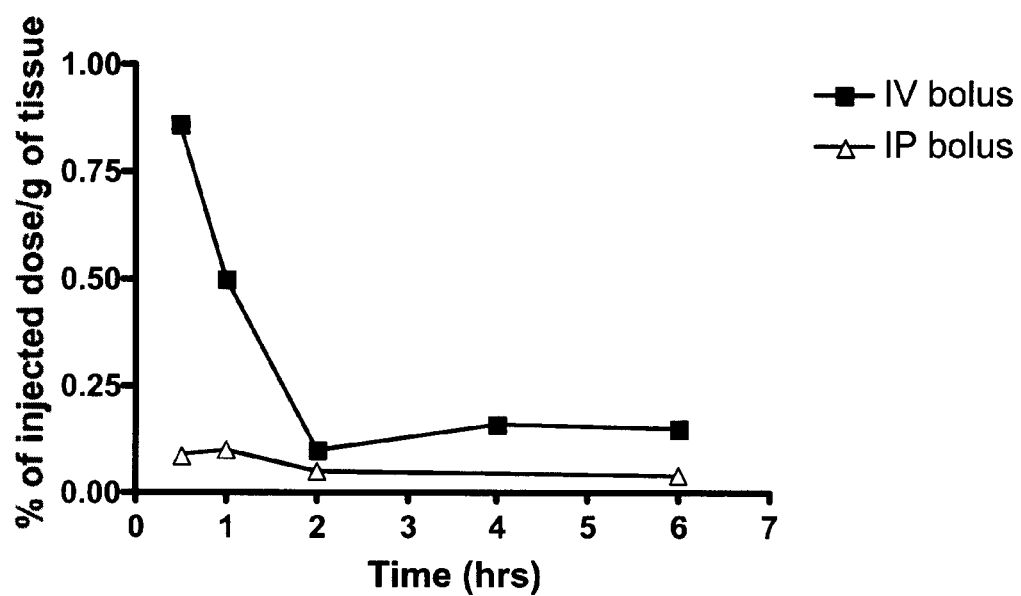
FIG. 10 shows the brain distribution of Etop-An2(3:1).
Figure 11:
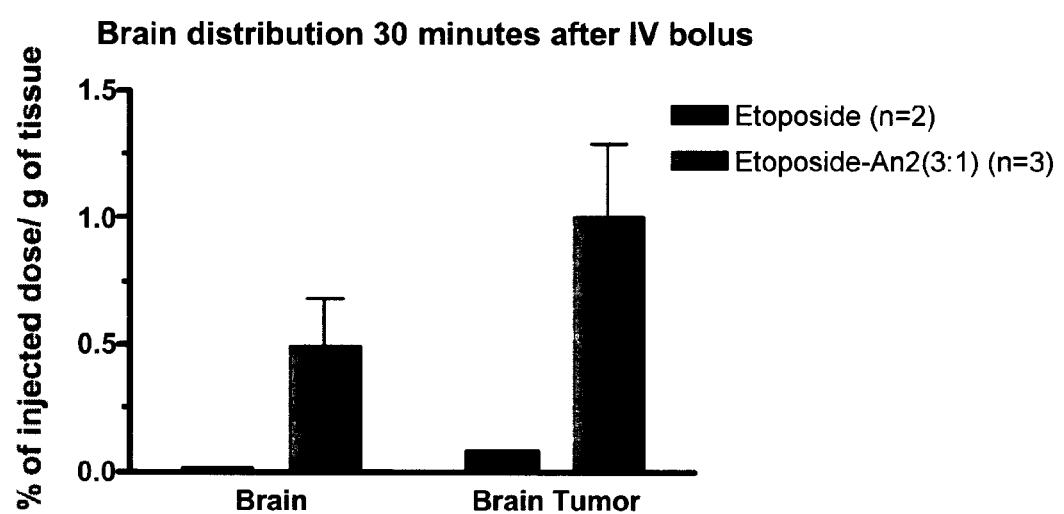
FIG. 11 shows the brain distribution of Etop-An2(3:1) compared to unconjugated etoposide thirty minutes after IV bolus administration.
Figure 12:
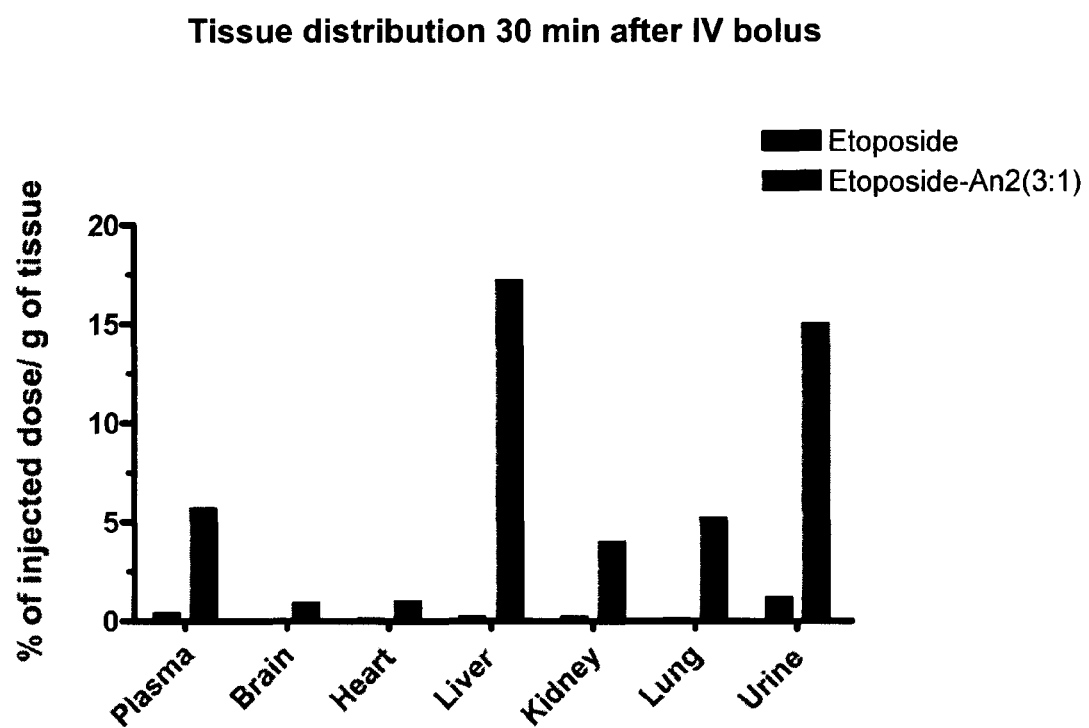
FIG. 12 shows the tissue distribution of Etop-An2(3:1) compared to unconjugated etoposide thirty minutes after IV bolus administration.

FIG. 9 shows the brain distribution of Etop$_{DMG}$-An2 following IV bolus administration in mice. In this figure, the left bar of each grouping shows results obtained with unconjugated etoposide and the right bar shows results obtained with Etop-An2(3:1). FIG. 10 shows the brain distribution of Etop-An2(3:1) following IV or IP bolus administration in mice. FIG. 11 compares the brain distribution of Etop-An2(3:1) versus unconjugated etoposide thirty minutes after IV bolus administration to mice. FIG. 12 shows the tissue distribution of Etop-An2(3:1) compared to unconjugated etoposide. In this figure, the left bar of each grouping shows results obtained with unconjugated etoposide and the right bar shows results obtained with Etop-An2(3:1); use of the Etop-An2(3:1) leads to increased concentration in the tissues studied.

Example 6

Anti-Tumor Effect of Doxorubicin-An2(3:1) Conjugate in a Mouse Model of Human Brain Tumor All animals used in these studies were handled and maintained in accordance to the Guidelines of the Canadian Council on Animal Care (CCAC). Animal protocols were approved by the Institutional Animal Care and Use Committee of Université du Québec à Montréal.

The intracerebral human brain tumor model was established by stereotactic inoculation of $5 \times 10^5$ U87 cells in nude mice brain. Female athymic nude mice (Crl:Nu/Nu-nuBR; 20-25 g, 4-6 weeks old; Charles River Canada, St-Constant, QC) were used for tumor models and were maintained in a pathogen-free environment. One hour before surgery, mice received a subcutaneous injection of buprenorphine (0.1 mg $kg^{-1}$). For tumor cell inoculation, mice were anesthetized by i.p. injection of ketamine/xylazine (120/10 mg $kg^{-1}$) and placed in a stereotactic apparatus (Kopf; Tujunga, Calif.). A burr hole was drilled 1.5 mm anterior and 2.5 mm lateral to the bregma. The cell suspension in 5 µL of serum free cell culture medium was injected over a 5 minute period using a Hamilton syringe at a depth of 3.5 mm.

Drug treatment started 3 days post-inoculation (Table 8). The therapeutic compound (e.g., doxorubicin or doxorubicin-An2(3:1) conjugate) was given intravenously by bolus tail-vein injection (once per week). Drug solutions were prepared in dextrose 5% water (D5W). Injection solutions were freshly prepared before each administration. Clinical signs of disease progression and body weights were monitored everyday. When mice reached terminal endpoints (20% of decrease in body weight), they were sacrificed by carbon dioxide asphyxiation.

TABLE 8

| Compound | Dose (mg/kg) | Administration | Survival (days) | | |
|---|---|---|---|---|---|
| | | | Median | | Mean |
| | | | Trial 1 | Trial 2 | Trial 1 |
| Control | 0 | i.v. | 18 | 22 | 18.5 |
| Doxorubicin | 6 | i.v. (1× per week) | 21 | 23 | 20.6 |
| (DoxSu)$_3$-An2 | 40 | i.v. (1× per week) | 22 | 28 | 21.1 |
| (DoxSu)$_3$-An2 + Angiopep2 + paclitaxel conjugate | 60 + 40 | i.p. (2× per week) + i.v. (1× per week) | 22 | — | 22.4 |

Figure 13A:
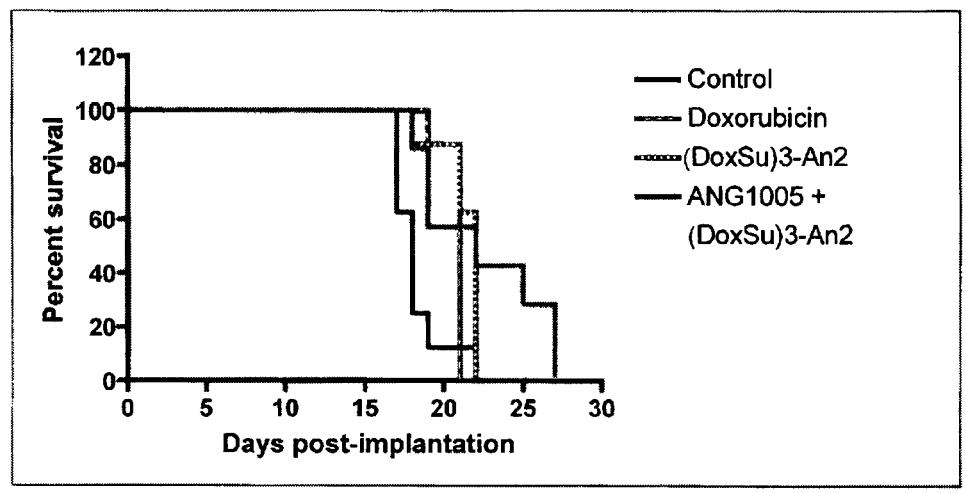
FIG. 13A and FIG. 13B each show the in vivo effect of (DoxSu)$_3$-An2 in mice that have been intracranially injected with U87 glioblastoma cells.
Figure 13B:
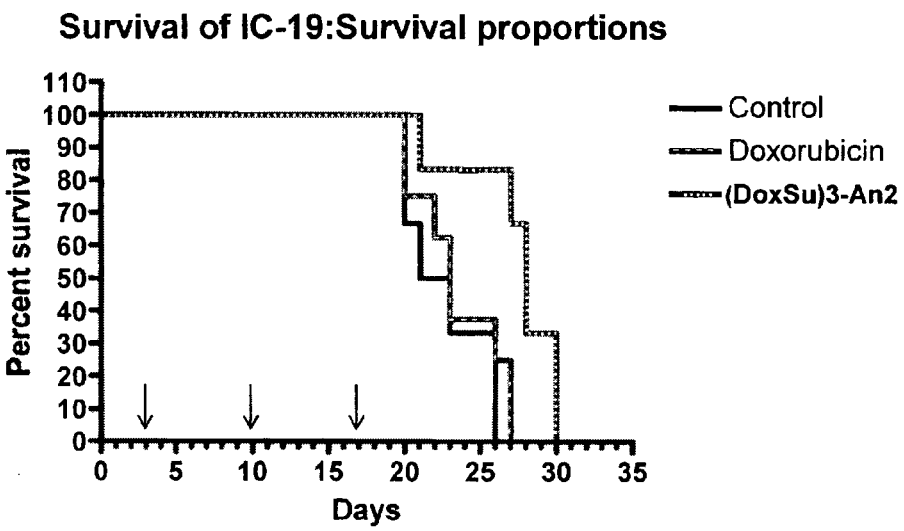

Each of FIGS. 13A and 13B show the efficacy of the (DoxSu)$_3$-An2 conjugate when administered alone or in combination with a paclitaxel-Angiopep2 conjugate. FIG. 13A shows results obtained in one trial and FIG. 13B shows results obtained in a second set of experiments. Statistical analysis of the data obtained from Trial 2 (FIG. 13B) showed that the observed 27% improvement was statistically significant (p<0.007).

Other Embodiments

The content of each publication, patent, and patent application mentioned in the present application is incorporated by reference. Although the invention has been described in details herein and illustrated in the accompanying drawings, it is to be understood that the invention is not limited to the embodiments described herein and that various changes and modifications may be effected without departing from the scope or spirit of the invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound having the structure:

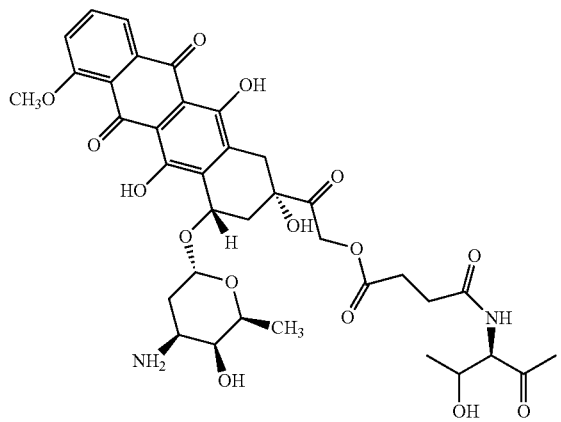

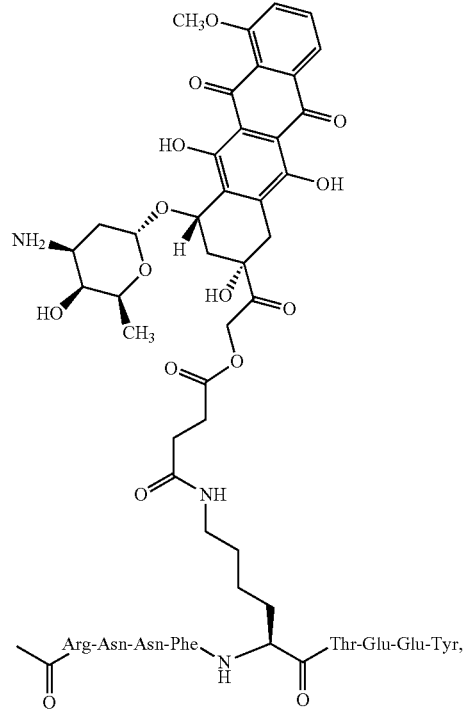

or a pharmaceutically acceptable salt thereof.

2. A pharmaceutical composition comprising the compound of claim 1 and a pharmaceutically acceptable carrier.

3. A method of treating a cancer, said method comprising administering to a patient a therapeutically effective amount of a compound of claim 1.

4. The method of claim 3, further comprising the administration of a second therapeutic agent.

5. The method of claim 3, wherein said second therapeutic agent is a polypeptide comprising the sequence of Angiopep-2 (SEQ ID NO:97), and wherein said Angiopep-2 is conjugated to an anticancer agent.

6. The method of claim 5, wherein said anticancer agent is paclitaxel.

7. The method of claim 6, wherein said second therapeutic agent is ANG1005, which has the following structure

131 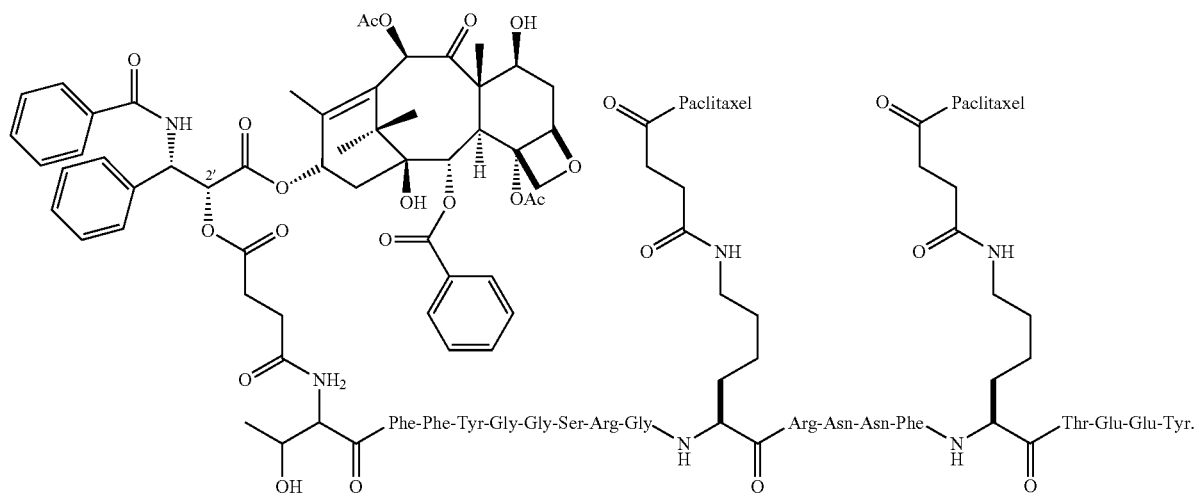 132 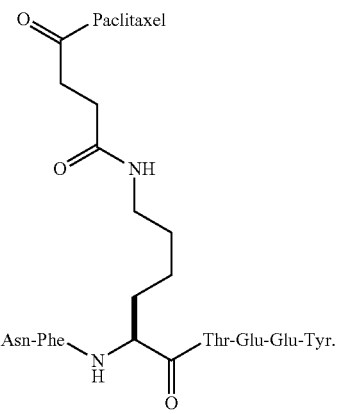
* * * * *